United States Patent
Ono et al.

(10) Patent No.: US 12,329,452 B2
(45) Date of Patent: Jun. 17, 2025

(54) OPHTHALMIC APPARATUS, METHOD FOR CONTROLLING OPHTHALMIC APPARATUS, AND COMPUTER-READABLE MEDIUM

(71) Applicant: CANON KABUSHIKI KAISHA, Tokyo (JP)

(72) Inventors: Mitsuhiro Ono, Tokyo (JP); Ritsuya Tomita, Kanagawa (JP)

(73) Assignee: Canon Kabushiki Kaisha, Tokyo (JP)

(*) Notice: Subject to any disclaimer, the term of this patent is extended or adjusted under 35 U.S.C. 154(b) by 600 days.

(21) Appl. No.: 17/588,367

(22) Filed: Jan. 31, 2022

(65) Prior Publication Data

US 2022/0151483 A1  May 19, 2022

Related U.S. Application Data

(63) Continuation of application No. PCT/JP2020/029310, filed on Jul. 30, 2020.

(30) Foreign Application Priority Data

| Aug. 9, 2019 | (JP) | 2019-147940 |
| Dec. 25, 2019 | (JP) | 2019-234950 |
| Mar. 17, 2020 | (JP) | 2020-046233 |

(51) Int. Cl.
*A61B 3/00* (2006.01)
*A61B 3/10* (2006.01)
(Continued)

(52) U.S. Cl.
CPC .......... *A61B 3/0083* (2013.01); *A61B 3/0025* (2013.01); *A61B 3/0058* (2013.01);
(Continued)

(58) Field of Classification Search
CPC ... A61B 3/0083; A61B 3/0025; A61B 3/0058; A61B 3/102; A61B 3/103; A61B 3/12;
(Continued)

(56) References Cited

U.S. PATENT DOCUMENTS

| 9,232,890 B2 | 1/2016 | Ono |
| 9,706,920 B2 * | 7/2017 | Okada .................... A61B 3/152 |

(Continued)

FOREIGN PATENT DOCUMENTS

| JP | 2010-162424 A | 7/2010 |
| JP | 2018-130206 A | 8/2018 |
| WO | 2019/100169 A1 | 5/2019 |

OTHER PUBLICATIONS

English translation of JP2018130206 (Year: 2018).*
(Continued)

*Primary Examiner* — Thomas K Pham
*Assistant Examiner* — Kuei-Jen L Edenfield
(74) *Attorney, Agent, or Firm* — Venable LLP

(57) ABSTRACT

An ophthalmic apparatus is provided that includes: an optical head unit; an information obtaining unit that, using a learned model obtained by learning information of a position relating to at least one of an eye to be examined and an optical head unit, obtains information of a position relating to at least one of an eye to be examined and the optical head unit from an image relating to an eye to be examined that is obtained using the optical head unit; and a drive controlling unit that controls driving of at least one of a supporter that supports a face of a subject and the optical head unit; in which, based on the obtained information of the position, the drive controlling unit controls the driving to cause at least one of the eye to be examined and the optical head unit to move to the position.

18 Claims, 15 Drawing Sheets

(51) Int. Cl.
*A61B 3/103* (2006.01)
*A61B 3/12* (2006.01)
*A61B 3/14* (2006.01)
*G06F 18/214* (2023.01)
*G06T 7/00* (2017.01)
*G06T 11/00* (2006.01)

(52) U.S. Cl.
CPC .............. *A61B 3/102* (2013.01); *A61B 3/103* (2013.01); *A61B 3/12* (2013.01); *A61B 3/14* (2013.01); *G06F 18/214* (2023.01); *G06T 7/0014* (2013.01); *G06T 11/00* (2013.01); *G06T 2207/20081* (2013.01); *G06T 2207/30041* (2013.01)

(58) Field of Classification Search
CPC ....... A61B 3/14; A61B 5/7267; A61B 5/0066; A61B 3/1025; A61B 3/152; A61B 3/00; A61B 3/10; A61B 5/00; A61B 3/15; G06F 18/214; G06T 7/0014; G06T 7/30; G06T 7/70; G06T 11/00; G06T 2207/10016; G06T 2207/10101; G06T 2207/20081; G06T 2207/30041; G06T 7/00; H04N 7/183; H04N 7/18; G06V 10/82; G06V 2201/03

USPC .................. 359/205–207, 211–215, 219–221
See application file for complete search history.

(56) References Cited

U.S. PATENT DOCUMENTS 9,743,830 B2 * 8/2017 Satake ................... A61B 3/102
2012/0249769 A1 * 10/2012 Naba ....................... A61B 3/10
348/78
2020/0323480 A1 10/2020 Shaked et al.

OTHER PUBLICATIONS

Feb. 17, 2022 International Preliminary Report on Patentability in International Patent Application No. PCT/JP2020/029310 (w/ English translation).
International Search Report and Written Opinion for International Patent Application No. PCT/JP2020/029310.
Stein DM et al., "A new quality assessment parameter for optical coherence tomography", British Journal of Ophthalmology, vol. 90, 2006, pp. 186-190.
U.S. Appl. No. 17/546,084; filed Dec. 9, 2021.
Jan. 9, 2024 Japanese Official Action in Japanese Patent Appln. No. 2022-194733.

* cited by examiner

OPHTHALMIC APPARATUS, METHOD FOR CONTROLLING OPHTHALMIC APPARATUS, AND COMPUTER-READABLE MEDIUM

CROSS-REFERENCE TO RELATED APPLICATIONS

This application is a Continuation of International Patent Application No. PCT/JP2020/029310, filed Jul. 30, 2020, which claims the benefits of Japanese Patent Application No. 2019-147940, filed Aug. 9, 2019, Japanese Patent Application No. 2019-234950, filed Dec. 25, 2019, and Japanese Patent Application No. 2020-046233, filed Mar. 17, 2020, all of which are hereby incorporated by reference herein in their entirety.

BACKGROUND OF THE INVENTION

Field of the Invention

The present invention relates to an ophthalmic apparatus, a method for controlling an ophthalmic apparatus, and a computer-readable medium.

Description of the Related Art

In recent years, an apparatus (OCT apparatus) which uses optical coherence tomography (OCT) to acquire a tomographic image by utilizing interference of low-coherence light has been put into practical use. The OCT apparatus can acquire a tomographic image with a resolution as high as that of the wavelength of light incident on the object to be examined. Therefore, a tomographic image of the object to be examined can be obtained with a high resolution.

The OCT apparatus is particularly useful as an ophthalmic apparatus for obtaining a tomographic image of the retina that is located in the fundus. In addition, as other ophthalmic apparatuses, a fundus camera (an apparatus for imaging a two-dimensional image of the fundus), a scanning laser ophthalmoscope (SLO), and a refractometer (eye refractive power measuring apparatus) and the like are also useful apparatuses. Further, apparatuses having a combination of the functions of these apparatuses are also useful apparatuses.

In such kind of ophthalmic apparatuses, it is important that an imaging unit (principally, a measurement optical system) of the apparatus for imaging the eye to be examined is accurately aligned with the eye to be examined. Japanese Patent Application Laid-Open No. 2010-162424 discloses an ophthalmic apparatus that projects an alignment index onto the cornea of the eye to be examined, divides and images reflected light from the cornea with an imaging device, detects the relative positions of the apparatus and the eye to be examined based on the position of a divided alignment index image, and performs alignment.

Here, in the case of an eye to be examined in which there is partial opacity due to a cataract or the like, in some cases the measuring light flux is scattered by the opacity and a tomogram cannot be brightly imaged. With regard to such kind of eye to be examined, it is known that in some cases a tomogram can be brightly imaged by shifting the optical axis on the measuring light side. However, with respect to an eye to be examined in which there is opacity, there is the problem that various adjustment operations relating to the apparatus such as shifting the optical axis of measuring light so that a tomogram or the like can be brightly imaged, or aligning the apparatus with the eye to be examined are difficult to perform unless the operator is familiar with these adjustment operations.

SUMMARY OF THE INVENTION

In view of the above problem, an object of one embodiment of the present invention is to provide an ophthalmic apparatus, a method for controlling an ophthalmic apparatus, and a computer-readable medium that, when performing imaging of an image relating to the fundus of an eye to be examined, can reduce the complexity of various adjustment operations relating to the apparatus, such as an operation to adjust an alignment position.

An ophthalmic apparatus according to one embodiment of the present invention includes: an optical head unit including an optical system arranged to irradiate an eye to be examined with light and detect return light from the eye to be examined; an information obtaining unit configured to, using a learned model obtained by learning positional information relating to at least one of an eye to be examined and an optical head unit, to obtain information of a position relating to at least one of an eye to be examined and the optical head unit from an image relating to an eye to be examined that is obtained using the optical head unit; and a drive controlling unit configured to control driving of at least one of a supporter that supports a face of a subject and the optical head unit; wherein, based on the obtained information of the position, the drive controlling unit controls the driving of the at least one of the supporter and the optical head unit to cause at least one of an eye to be examined and the optical head unit to move to the position.

Further features of the present invention will become apparent from the following description of exemplary embodiments with reference to the attached drawings.

DESCRIPTION OF THE EMBODIMENTS

Figure 1:
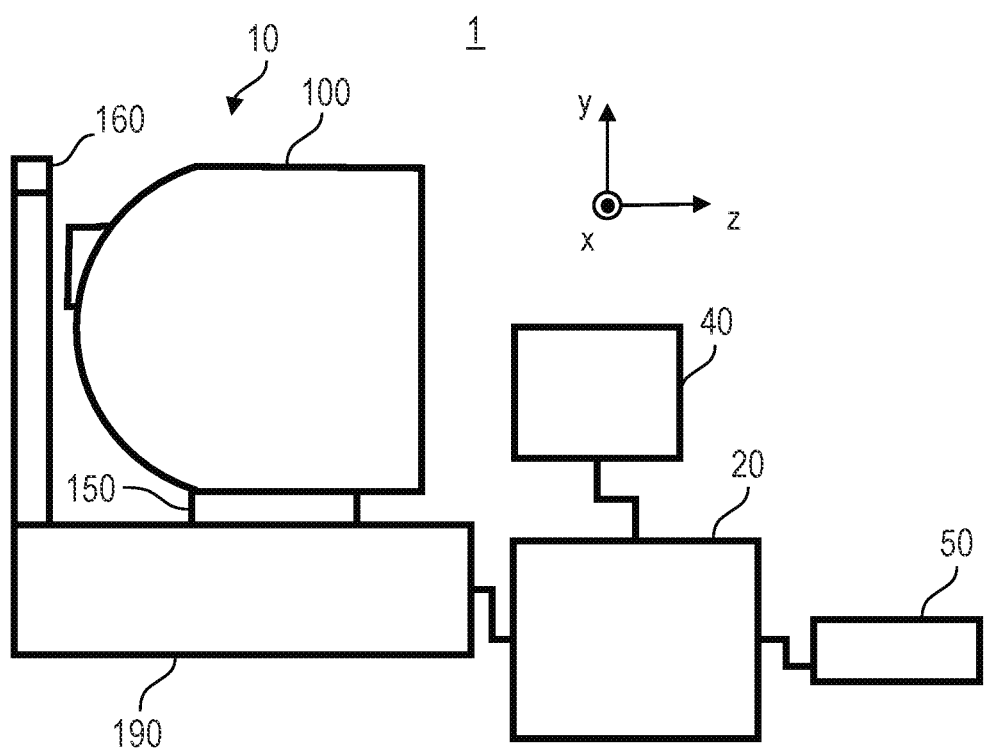
FIG. 1 is a view illustrating a schematic configuration example of an OCT apparatus according to Embodiment 1.

Exemplary embodiments of the present invention will now be described in detail in accordance with the accompanying drawings.

However, the dimensions, materials, shapes and relative positions of the components described in the following embodiments are not determinate, and can be changed according to a configuration of an apparatus to which the present invention is applied or to various conditions. Further, identical or functionally similar elements are denoted by the same reference numerals in different drawings.

Note that, in the following, the phrase "image relating to the fundus" refers to an image includes information pertaining to a fundus, such as a tomographic image and a three-dimensional tomographic image which are cross-sectional images of a fundus, and a fundus front image is a two-dimensional image of a fundus, an image including a ring image, and an en-face image, an OCTA front image and an OCTA tomographic image that are described later. Further, in the following, the phrase "image of the anterior ocular segment" refers to an image such as a two-dimensional front image of the anterior ocular segment (anterior ocular segment image) and a transillumination image that is an image of a pupil region illuminated by reflected light from the fundus when an eye to be examined is irradiated with light. The phrase "image relating to the eye to be examined" refers to an image that includes the image relating to the fundus and the image of the anterior ocular segment described above.

Further, the term "machine learning model" refers to a learning model that learned according to a machine learning algorithm. Specific examples of algorithms for machine learning include the nearest-neighbor method, the naive Bayes method, the decision tree, and the support vector machine. Further, deep learning (deep structured learning) which utilizes a neural network to generate, by itself, feature values and combining weighting factors for learning may also be mentioned. Algorithms that can be utilized among the aforementioned algorithms can be appropriately used and applied to the embodiments and modifications that are described hereunder. Further, the term "teaching data" refers to training data that is constituted by pairs of input data and output data (ground truth). Furthermore, the term "correct answer data" refers to a ground truth of training data (teaching data).

Note that, the term "learned model" refers to a model which is obtained by performing training (has performed learning), with respect to a machine learning model that is in accordance with any machine learning algorithm, using appropriate training data in advance. However, although the learned model is a model obtained using appropriate training data in advance, the learned model is not a model that does not perform further learning, and is a model that can also perform incremental learning. Incremental learning can also be performed after the apparatus is installed at the usage destination.

Embodiment 1

Hereunder, an ophthalmic imaging apparatus as one example of an ophthalmic apparatus according to Embodiment 1 of the present invention is described while referring to FIG. 1 to FIG. 9, FIG. 11A to FIG. 11C, and FIG. 12. The ophthalmic imaging apparatus according to the present embodiment is an ophthalmic imaging apparatus that images the fundus of an eye to be examined, and in particular relates to an apparatus used for obtaining a fundus front image and a tomographic image which are two-dimensional images of the fundus of an eye to be examined. In the present embodiment, an optical coherence tomography apparatus (OCT apparatus) that performs alignment of the apparatus with respect to an eye to be examined based on an anterior ocular segment image using a learned model is described as an example of an ophthalmic imaging apparatus.

(Schematic Configuration of Apparatus)

A schematic configuration of the OCT apparatus according to the present embodiment will be described using FIG. 1. FIG. 1 is a side view of a schematic configuration example of an OCT apparatus 1. An imaging unit 10, a controlling unit 20, a display unit 40 and an input unit 50 are provided in the OCT apparatus 1. An optical head unit 100, a stage unit 150, a base unit 190 that has a built-in spectrometer which is described later, and a face receiving unit 160 (supporter) are provided in the imaging unit 10.

The optical head unit 100 includes a measurement optical system for irradiating an eye to be examined with light and detecting return light from the eye to be examined, and imaging an anterior ocular segment image, a fundus front image and a tomographic image. The stage unit 150 is a moving unit which is capable of moving the optical head unit 100 in the XYZ directions in the drawing by using a motor (not illustrated). The face receiving unit 160 is a chin rest that can facilitate the fixation of an eye of a subject (eye to be examined) by fixing the chin and forehead of the subject.

The controlling unit 20 is connected to the imaging unit 10, the display unit 40 and the input unit 50, and can control these units. The controlling unit 20, for example, can control movement of the stage unit 150 to perform alignment of the optical head unit 100 with respect to the eye to be examined. Further, the controlling unit 20 can also perform generation of an anterior ocular segment image, a fundus front image, a tomographic image or the like based on data obtained by the imaging unit 10. Whilst the controlling unit 20 can be constituted using a common computer including a processor and a memory, the controlling unit 20 may also be constituted as a dedicated computer of the OCT apparatus 1. Note that, the controlling unit 20 may be a built-in (internal) computer of the imaging unit 10, and not just a computer that is a separate body (external computer) to which the imaging unit 10 is communicably connected. Further, the controlling unit 20 may be, for example, a personal computer, and a desktop PC, a notebook PC, or a tablet PC (portable information terminal) may be used. At such time, a communication connection between these units or the like may be a connection by wired communication or may be a connection by wireless communication.

The display unit 40 is constituted by an arbitrary monitor, and displays various information such as subject information, various images, a mouse cursor in accordance with operation of the input unit 50, and the like in accordance with control of the controlling unit 20. The input unit 50 is an input device that provides instructions to the controlling unit 20, and specifically includes a keyboard and a mouse. Note that, the display unit 40 may be a touch-panel type display, and in such case, the display unit 40 also serves as the input unit 50.

Note that, although in the present embodiment, the imaging unit 10, the controlling unit 20, the display unit 40 and the input unit 50 are each constituted as a separate unit, some or all of these units may be configured as an integrated body. Further, another imaging apparatus or storage device or the like that is not illustrated in the drawing may be connected to the controlling unit 20.

(Configuration of Measurement Optical System and Spectrometer)

Figure 2:
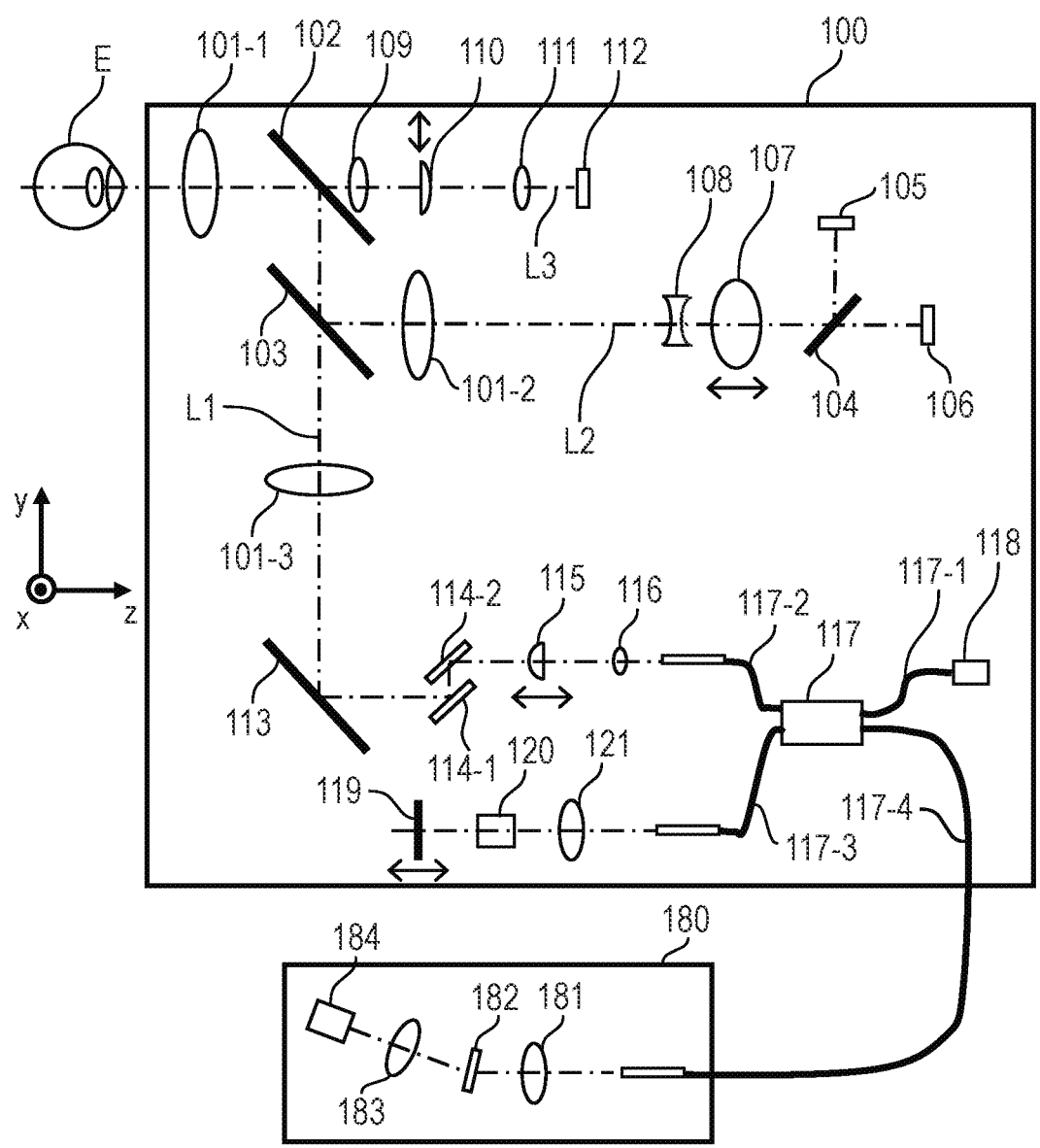
FIG. 2 is a view illustrating an example of the optical configuration of an imaging unit according to Embodiment 1.

Next, with reference to FIG. 2, a configuration example of the measurement optical system and the spectrometer of the present embodiment will be described. FIG. 2 illustrates one example of the optical configuration of the imaging unit 10. First, the internal configuration of the optical head unit 100 will be described.

In the optical head unit 100, an objective lens 101-1 is disposed facing an eye to be examined E, and a first dichroic mirror 102 as a first optical path splitting unit is arranged on the optical axis thereof. The optical path from the objective lens 101-1 is branched by the first dichroic mirror 102 according to the respective wavelength bands of the light rays into a measurement optical path L1 of an OCT optical system and an optical path L2 for fundus observation and a fixation lamp, and an optical path L3 for observation of the anterior ocular segment. Further, a second dichroic mirror 103 is arranged in the reflecting direction of the first dichroic mirror 102. The optical path in the reflecting direction of the first dichroic mirror 102 is branched by the second dichroic mirror 103 according to the respective wavelength bands of the light rays into the measurement optical path L1 of the OCT optical system and the optical path L2 for fundus observation and the fixation lamp.

Note that, in the configuration according to the present embodiment, the optical path L3 for observation of the anterior ocular segment is arranged in the transmitting direction of the first dichroic mirror 102, and an optical path that arrives at the measurement optical path L1 of the OCT optical system and the optical path L2 for fundus observation and the fixation lamp is arranged in the reflecting direction of the first dichroic mirror 102. Further, the measurement optical path L1 of the OCT optical system is arranged in the transmitting direction of the second dichroic mirror 103, and the optical path L2 for fundus observation and the fixation lamp is arranged in the reflecting direction of the second dichroic mirror 103. However, the optical paths provided in the transmitting direction and reflecting direction of each dichroic mirror may be the opposite of the optical paths in the configuration according to the present embodiment.

The optical path L2 for fundus observation and an internal fixation lamp is also branched by a third dichroic mirror 104 that is a third optical path splitting unit according to the respective wavelength bands of the light rays into an optical path to a CCD 105 for fundus observation and an optical path to a fixation lamp 106.

In the optical path L2 for fundus observation and the internal fixation lamp, lenses 101-2, 108 and 107, and the third dichroic mirror 104 are arranged in that order from the second dichroic mirror 103. Further, the fixation lamp 106 is arranged in the transmitting direction of the third dichroic mirror 104, and the CCD 105 for fundus observation is arranged in the reflecting direction. Note that, the CCD 105 may be arranged in the transmitting direction of the third dichroic mirror 104, and the fixation lamp 106 may be arranged in the reflecting direction.

The lens 107 is a focusing lens, and is used for focus adjustment relating to the optical path L2 for fundus observation and the fixation lamp. The lens 107 can be driven in the optical axis directions indicated by arrows in the drawing by an unshown motor or the like controlled by the controlling unit 20.

The CCD 105 has sensitivity to a wavelength of illumination light for fundus observation (not illustrated), specifically, a wavelength in the vicinity of 780 nm. On the other hand, the fixation lamp 106 generates visible light to prompt the subject to fix their line of sight. The controlling unit 20 can generate a fundus front image that is a two-dimensional image of the fundus of the eye to be examined E based on a signal that is output from the CCD 105.

A lens 109, a prism lens 110, a lens 111, and an infrared CCD 112 for observation of the anterior ocular segment are provided in that order from the first dichroic mirror 102 on the optical path L3 for observation of the anterior ocular segment. The prism lens 110 is one example of a dividing unit having an image splitting prism that divides a light flux of an anterior ocular segment image into a plurality of light fluxes at a position conjugate with the anterior ocular segment of the eye to be examined E. Here, the prism lens 110 has an image splitting prism function on a first surface from the eye to be examined side, and has a lens function on the second surface. Note that, the prism lens 110 is provided so as to be insertable onto and retractable from the optical path L3 for observation of the anterior ocular segment from above as indicated by arrows in the drawing.

The lens 111 is one example of a relay optical system that relays an anterior ocular segment image. The infrared CCD 112 images an anterior ocular segment image which was formed by the lens 111 as an image-forming unit. The infrared CCD 112 has sensitivity to a wavelength of illumination light for observation of the anterior ocular segment (not illustrated), specifically, a wavelength in the vicinity of 970 nm. The controlling unit 20 can generate an anterior ocular segment image that is a two-dimensional front image of the anterior ocular segment of the eye to be examined E based on a signal that is output from the infrared CCD 112.

Optical members constituting an OCT optical system are arranged on the measurement optical path L1 of the OCT optical system, and the measurement optical path L1 of the OCT optical system has a configuration for imaging a tomogram of the fundus of the eye to be examined E. More specifically, the OCT optical system is used for obtaining interference signals for generating a tomographic image.

A lens 101-3, a mirror 113, an X-scanner 114-1 and a Y-scanner 114-2 for scanning light over the fundus of the eye to be examined E, and lenses 115 and 116 are arranged in that order from the second dichroic mirror 103 on the measurement optical path L1.

The X-scanner 114-1 and the Y-scanner 114-2 are one example of a scanning unit for scanning measuring light for OCT, and are provided for the purpose of scanning measuring light over the fundus of the eye to be examined E. The X-scanner 114-1 is used for scanning measuring light in the X direction, and the Y-scanner 114-2 is used for scanning measuring light in the Y direction. Although in the present embodiment, the X-scanner 114-1 and the Y-scanner 114-2 are each constituted by a galvanometer mirror, the X-scanner 114-1 and the Y-scanner 114-2 may be constituted using any deflecting unit according to the desired configuration. Further, the scanning unit for scanning measuring light may be constituted, for example, by a deflecting unit capable of deflecting light in two-dimensional directions with one mirror such as an MEMS mirror.

The lens 115 is a focusing lens and is used for adjusting the focus on the fundus of light from a light source 118 that is emitted from an optical fiber 117-2 connected to an optical coupler 117. The lens 115 can be driven in the optical axis directions indicated by arrows in the drawing by an unshown motor or the like controlled by the controlling unit 20. By this focus adjustment, light from the fundus is imaged into a spot shape at the tip of the optical fiber 117-2 and simultaneously enters the optical fiber 117-2.

Next, the configuration of an optical path from the light source 118, a reference optical system, and a spectrometer will be described. The light source 118 is a super luminescent diode (SLD) that is a typical low-coherence light source. In the present embodiment, an SLD that has a central wavelength of 855 nm and a wavelength bandwidth of about 100 nm is used as the light source 118. In this case, the bandwidth influences the optical axial resolution of the obtained tomographic image and is therefore an important parameter. Further, with respect to the kind of light source, although an SLD is selected in this case, it suffices that the light source is capable of emitting low-coherence light, and an amplified spontaneous emission (ASE) light source or the like can also be used. In view of the purpose of performing measurement with respect to the eye, the central wavelength can fall within the near infrared range. Further, because the central wavelength influences the lateral resolution of the obtained tomographic image, the central wavelength can be made as short as possible. Because of these two reasons, in the present embodiment, the central wavelength is set at 855 nm.

The light source 118 is connected to the optical coupler 117 through an optical fiber 117-1. Single-mode optical fibers 117-1 to 117-4 are connected to and integrated with the optical coupler 117. The light emitted from the light source 118 is divided into measuring light and reference light by the optical coupler 117, and the measuring light is guided to the measurement optical path L1 through the optical fiber 117-2, and the reference light is guided to the reference optical system through the optical fiber 117-3. The measuring light passes through the measurement optical path L1 and is irradiated onto the fundus of the eye to be examined E, and due to reflection and scattering by the retina, the return light passes through the same optical path and reaches the optical coupler 117.

On the other hand, the reference light that was divided by the optical coupler 117 and guided by the optical fiber 117-3 is emitted to the reference optical system. In the reference optical system, a lens 121, a dispersion compensation glass 120, and a mirror 119 (reference mirror) are arranged in that order from the emitting end portion of the optical fiber 117-3.

The reference light that is emitted from the emitting end of the optical fiber 117-3 passes through the lens 121 and the dispersion compensation glass 120 and reaches the mirror 119 and is reflected. The dispersion compensation glass 120 is inserted into the optical path in order to cause the dispersion of the measuring light and the dispersion of the reference light to match. The reference light reflected by the mirror 119 returns along the same optical path, and reaches the optical coupler 117. The mirror 119 can be driven in the optical axis directions indicated by arrows in the drawing by an unshown motor or the like controlled by the controlling unit 20.

The return light of the measuring light that returned from the eye to be examined E and the reference light reflected from the mirror 119 are combined by the optical coupler 117 into interference light. Here, the interference occurs when the optical path length of the measuring light and the optical path length of the reference light become substantially equal to each other. Therefore, the mirror 119 can be moved in the optical axis direction by the aforementioned motor or the like to adjust the optical path length of the reference light to the optical path length of the measuring light that varies depending on the eye to be examined E. The interference light is guided to a spectrometer 180 through the optical fiber 117-4.

The spectrometer 180 is one example of a detecting unit for detecting interference light. Lenses 181 and 183, a diffraction grating 182, and a line sensor 184 are provided in the spectrometer 180. The interference light exiting from the optical fiber 117-4 is shaped by the lens 181 into substantially parallel light, and thereafter is diffracted by the diffraction grating 182, and imaged onto the line sensor 184 by the lens 183.

Information relating to intensity distribution in an interference signal obtained by the line sensor 184 that is a detecting element is output as an output signal to the controlling unit 20. The controlling unit 20 can generate a tomographic image based on the interference signal output from the line sensor 184.

In the present embodiment, a Michelson interferometer is formed by the measurement optical system, reference optical system and spectrometer optical system which are constituted by the respective members arranged in the measurement optical path L1. In this regard, a Mach-Zehnder interferometer may also be used as an interferometer. For example, in accordance with the light amount difference between the measuring light and the reference light, the Mach-Zehnder interferometer can be used in a case where the light amount difference is large, and the Michelson interferometer can be used in a case where the light amount difference is relatively small.

(Method for Imaging Tomographic Image)

Figure 3:
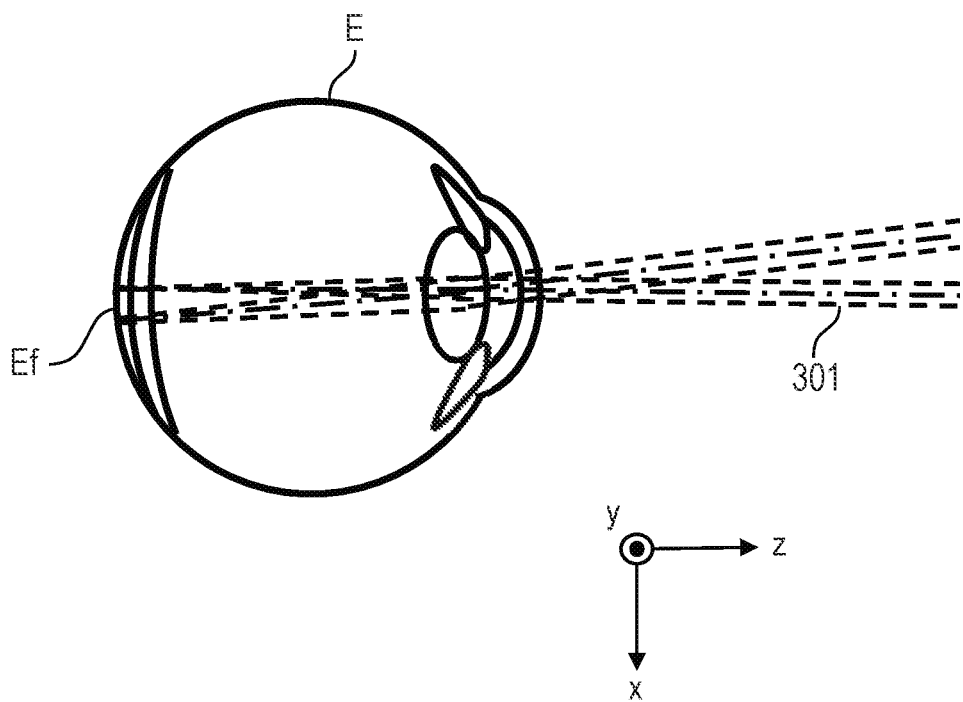
FIG. 3 is a view for describing a light flux of measuring light that is irradiated onto a fundus.

Next, a method for imaging a tomographic image using the OCT apparatus 1 will be described with reference to FIG. 3. FIG. 3 is a view for describing a light flux of measuring light irradiated onto the fundus. The controlling unit 20 of the OCT apparatus 1 can image a tomographic image of a desired site in a fundus Ef of the eye to be examined E by controlling the X-scanner 114-1 and the Y-scanner 114-2.

FIG. 3 illustrates a state in which the eye to be examined E is irradiated with a measuring light 301 and scanning in the X direction is being performed with respect to the fundus Ef. In order to image a tomographic image, first, the measuring light is scanned in the X direction on the fundus Ef, and information pertaining to a predetermined number of rounds of imaging from an imaging range in the X direction on the fundus Ef is obtained by the line sensor 184.

Here, acquiring tomographic information from one point of the eye to be examined E is referred to as an "A-scan". Further, the intensity distribution on the line sensor 184 obtained at a certain position in the X direction is subjected to a fast Fourier transform (FFT), and an image obtained by converting the obtained linear intensity distribution into density or color information is called an "A-scan image". In addition, a two-dimensional image in which a plurality of A-scan images are aligned is called a "B-scan image (tomographic image)".

Further, a plurality of B-scan images can be obtained by, after performing imaging of a plurality of A-scan images to construct one B-scan image, moving the scanning position in the Y-axis direction and performing scanning again in the X-axis direction. A three-dimensional tomographic image can be constructed by aligning a plurality of B-scan images in the Y direction. The controlling unit 20 can display a plurality of B-scan images or a three-dimensional tomographic image constructed from a plurality of B-scan images on the display unit 40, and an examiner can use these images for diagnosis with respect to the eye to be examined E.

Figure 4:
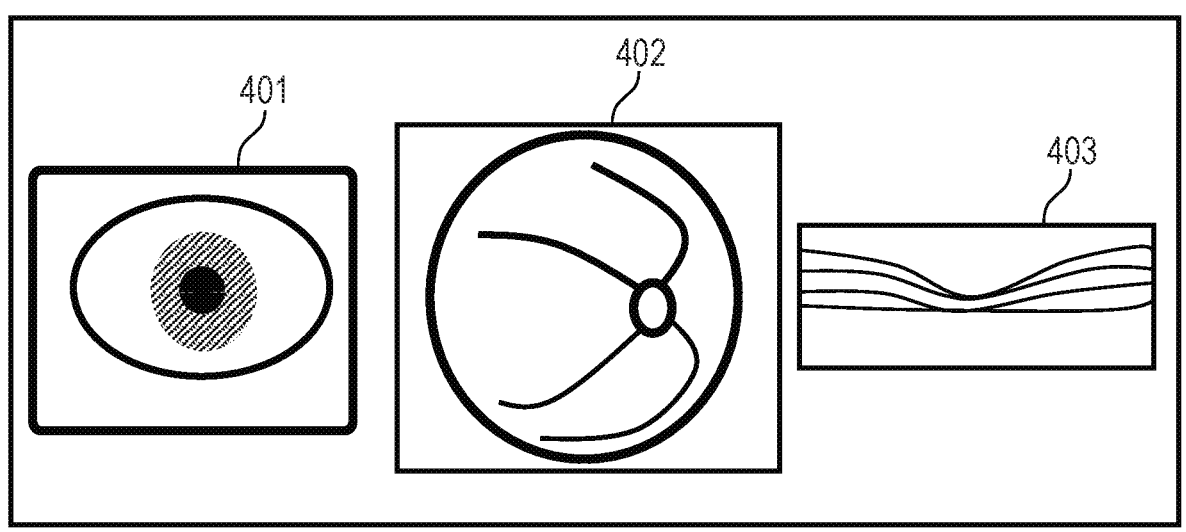
FIG. 4 illustrates an example of a display of an anterior ocular segment image, a fundus front image, and a tomographic image.

FIG. 4 is a view that illustrates an example of an anterior ocular segment image 401, a fundus front image 402, and a B-scan image 403 that is a tomographic image which are displayed on the display unit 40. The anterior ocular segment image 401 is an image generated by processing the output of the infrared CCD 112, the fundus front image 402 is an image generated by processing the output of the CCD 105, and the B-scan image 403 is an image generated by processing the output of the line sensor 184 as mentioned above.

(Configuration of Controlling Unit)

Figure 5:
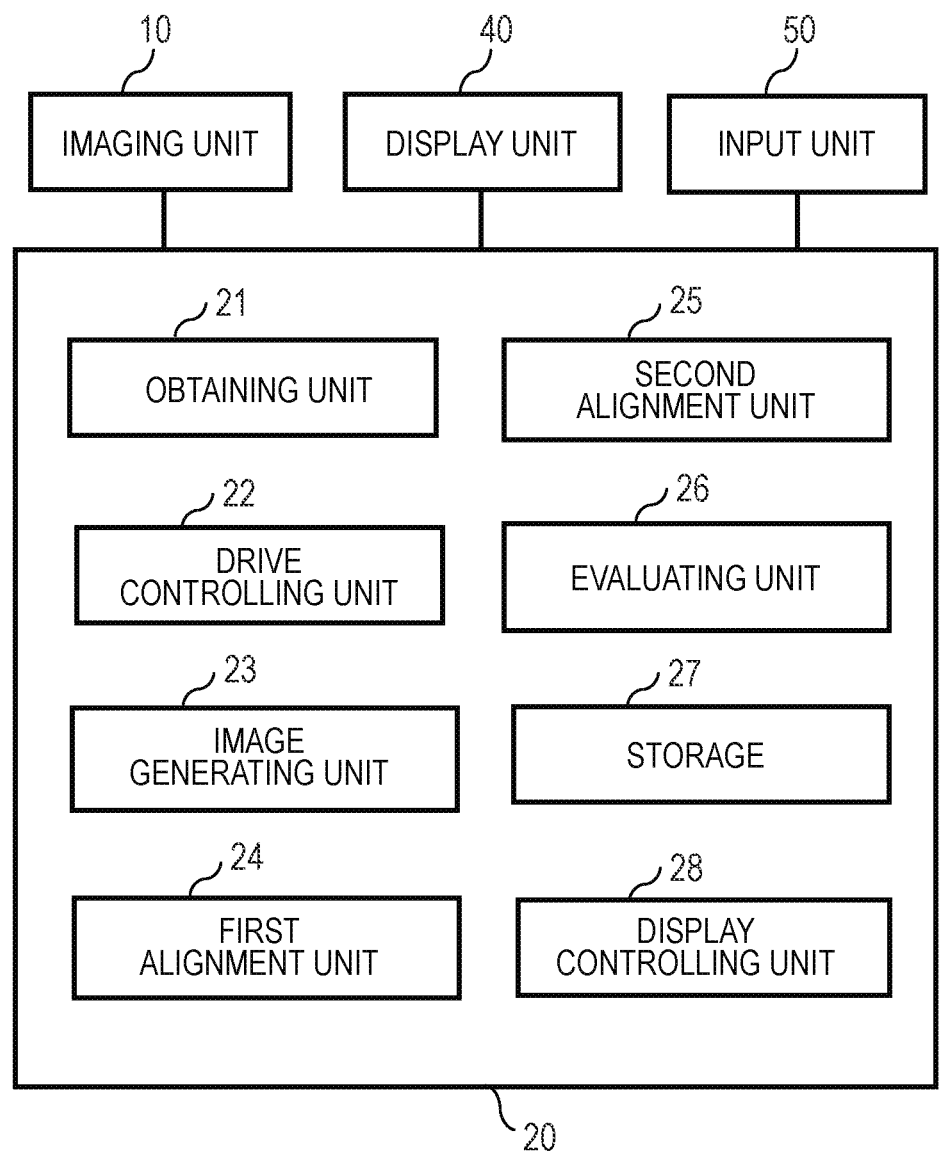
FIG. 5 is a block diagram illustrating an example of a controlling unit according to Embodiment 1.

Next, the configuration of the controlling unit 20 will be described with reference to FIG. 5. FIG. 5 is a block diagram illustrating an example of the configuration of the controlling unit 20. An obtaining unit 21, a drive controlling unit 22, an image generating unit 23, a first alignment unit 24 (first information obtaining unit), a second alignment unit 25 (second information obtaining unit), an evaluating unit 26, a storage 27, and a display controlling unit 28 are provided in the controlling unit 20.

The obtaining unit 21 can obtain various signals that are output from the CCD 105, the infrared CCD 112, and the line sensor 184. Further, the obtaining unit 21 can obtain an instruction from an operator via the input unit 50. In addition, the obtaining unit 21 can obtain various kinds of information such as subject information and various kinds of images such as tomographic images which are stored in the storage 27.

The drive controlling unit 22 controls driving of various components inside the imaging unit 10. Specifically, the drive controlling unit 22 can control driving of, for example, the stage unit 150, the lens 107, the prism lens 110, the X-scanner 114-1, the Y-scanner 114-2, the lens 115, and the mirror 119. The drive controlling unit 22 can also perform control for turning on and off an unshown illumination light source for fundus illumination and illumination light source for anterior ocular segment observation, the fixation lamp 106, and the light source 118. In addition, the drive controlling unit 22 can also control driving of the face receiving unit 160.

The image generating unit 23 can generate a fundus front image based on an output signal of the CCD 105 which the obtaining unit 21 obtained, generate an anterior ocular segment image based on an output signal of the infrared CCD 112, and generate a tomographic image based on an interference signal output from the line sensor 184. Note that, a known arbitrary method can be adopted as a method for generating an ophthalmic image such as a tomographic image or a fundus front image from ophthalmic information such as data relating to a tomogram or data relating to the fundus of the eye to be examined E.

The first alignment unit 24 can perform first alignment processing that determines information pertaining to a position (first alignment position) at which the optical head unit 100 should be disposed in the XYZ directions with respect to the eye to be examined E, based on an anterior ocular segment image generated by the image generating unit 23. Note that, the information pertaining to the first alignment position may be coordinates with respect to XYZ coordinates at which the optical head unit 100 should be disposed in the coordinate system of the optical head unit 100, or may be a movement amount (vector) of the optical head unit 100 to the first alignment position.

The first alignment unit 24 (first information obtaining unit) can also perform adjustment of the fundus focus. In the present embodiment, the first alignment unit 24 can obtain information pertaining to positions at which the lenses 107 and 115 should be disposed, based on a fundus front image generated by the image generating unit 23. Note that, coordinates of the positions or movement amounts to the relevant positions may be included in the positional information.

In addition, the first alignment unit 24 can perform adjustment of a coherence gate (CG). In the present embodiment, the first alignment unit 24 can obtain information pertaining to a position at which the mirror 119 should be disposed, based on a tomographic image generated by the image generating unit 23. Note that, the coordinates of the position or a movement amount to the relevant position may be included in the positional information.

The second alignment unit 25 (second information obtaining unit) can determine information pertaining to a position (second alignment position) at which the optical head unit 100 should be disposed with respect to the eye to be examined E from an anterior ocular segment image generated by the image generating unit 23, by using a learned model that is described later. Here, the learned model generates output data according to the learning tendency. Therefore, by using the learned model, the second alignment unit 25 can determine a second alignment position that depends on the learning tendency of the learned model, which is different from the first alignment position. Note that, the information pertaining to the second alignment position may be coordinates with respect XYZ coordinates at which the optical head unit 100 should be disposed in the coordinate system of the optical head unit 100, or may be a movement amount (vector) of the optical head unit 100 to the second alignment position.

The evaluating unit 26 can perform an evaluation of the image quality of a tomographic image generated by the image generating unit 23. In the present embodiment, a Q index value is used as the evaluation index for tomographic images. A method for calculating a Q index value is described in: "Stein D M, Ishikawa H, Hariprasad R, Wollstein G, Noecker R J, Fujimoto J G, Shuman J S, 'A new quality assessment parameter for optical coherence tomography', British Journal of Ophthalmology 2006; 90: pp. 186-190". Note that, although in the present embodiment, a Q index value is used as an evaluation index for image quality, a signal-to-noise ratio or a contrast value or the like may be used as an image evaluation index.

The storage 27 can store various kinds of information and various kinds of images that are generated. The storage 27 also serves as a subject information storage that stores identification information and the like pertaining to the subject. In addition, the storage 27 can store programs for imaging and the like.

The display controlling unit 28 can cause various kinds of information including subject information, various kinds of images such as a tomographic image, and a screen for imaging and the like to be displayed on the display unit 40. The display controlling unit 28 can also cause information that was input by the examiner and the like to be displayed on the display unit 40.

The respective components other than the storage 27 of the controlling unit 20 may be constituted by a software module executed by a processor such as a CPU (Central Processing Unit) or an MPU (Micro Processing Unit). Note that, the processor may be, for example, a GPU (Graphical Processing Unit) or a FPGA (Field-Programmable Gate Array) or the like. Further, the respective components in question may be constituted by a circuit that serves a specific function such as an ASIC, or the like. The storage 27, for example, may be constituted by any storage medium such a memory or an optical disk such as a hard disk.

(Flow of Imaging a Tomographic Image)

Figure 6A:
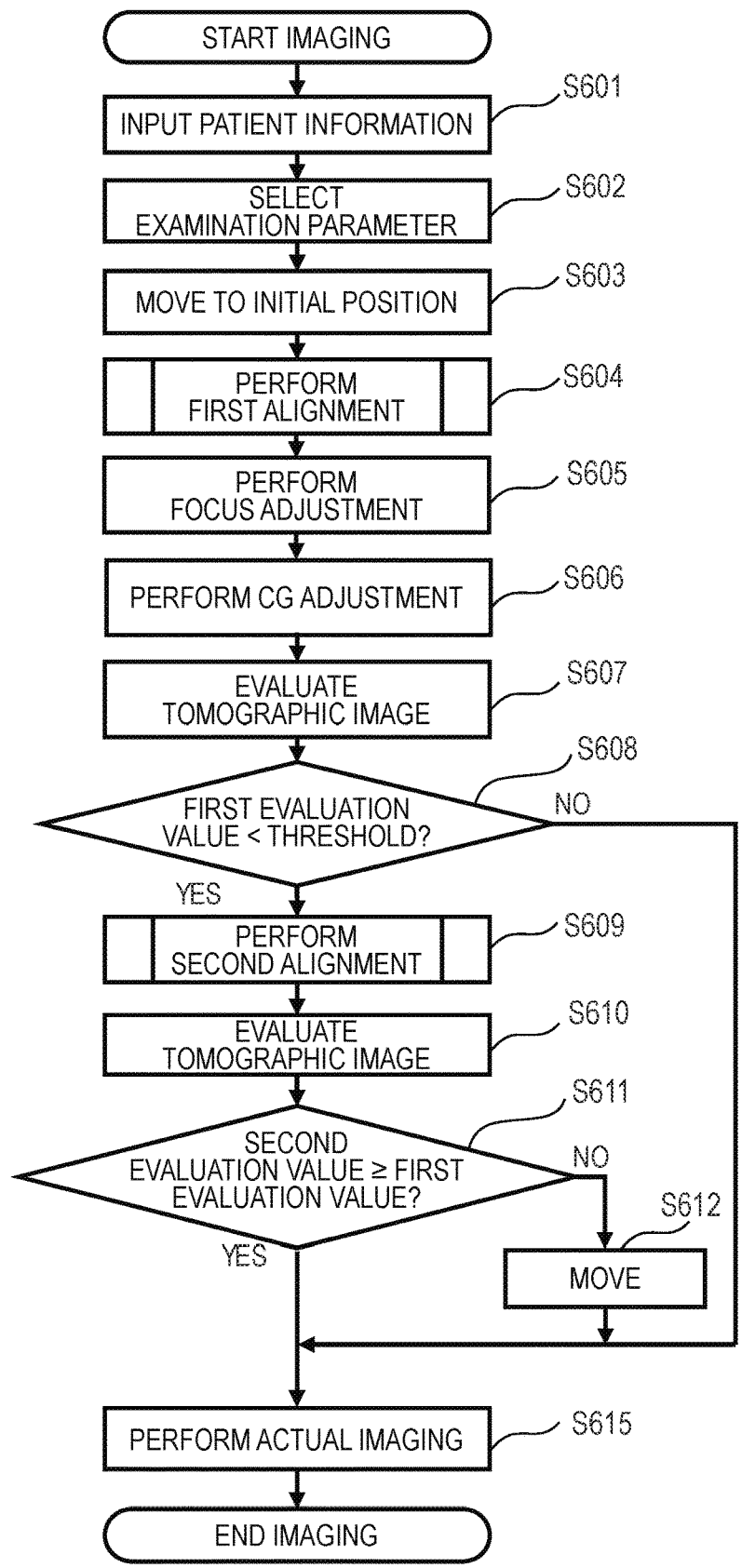
FIG. 6A is a flowchart illustrating a series of processing pertaining to imaging of an image.
Figure 6B:
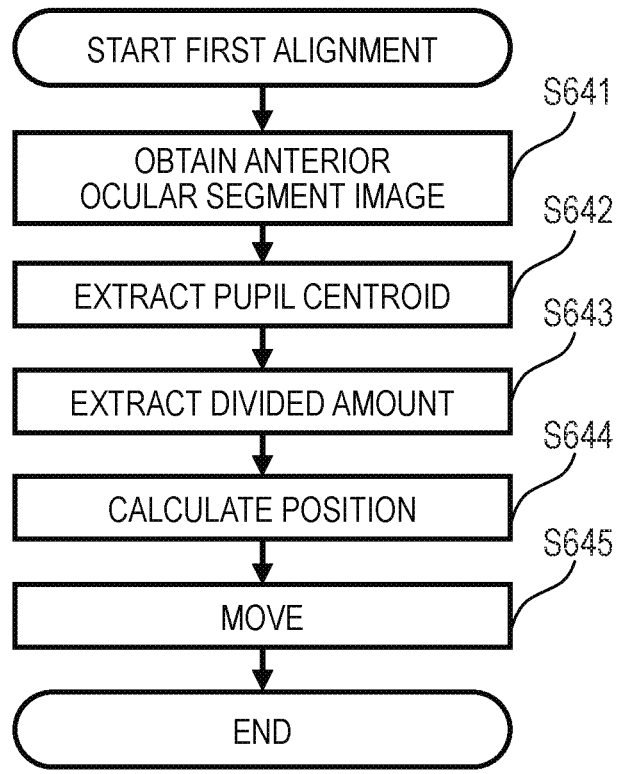
FIG. 6B is a flowchart illustrating first alignment processing.

Next, with reference to FIG. 6A to FIG. 6C, the flow of imaging an image according to the present embodiment will be described in step order. FIG. 6A is a flowchart illustrating a series of processing pertaining to imaging of an image according to the present embodiment. First, when the operator, for example, presses a "Start Imaging" button displayed on the display unit 40, a program for imaging is executed by the controlling unit 20, and the display controlling unit 28 displays a screen for imaging on the display unit 40. Further, the drive controlling unit 22 simultaneously actuates the X-scanner 114-1 and the Y-scanner 114-2.

When imaging of an image starts, in step S601, the display controlling unit 28 displays a patient information input screen on the display unit 40. On the patient information input screen, the operator (examiner) selects a patient, or if it is the first visit by the patient, the operator (examiner) inputs patient information.

In step S602, the display controlling unit 28 displays an examination parameter selection screen on the display unit 40. On the examination parameter selection screen, the examiner can set, as examination parameters, whether the eye to be examined E is the left or right eye, the range in which to perform tomography, the number of times to image a tomographic image, the number of A-scan images to be included in a B-scan image, and the like. Further, the examiner can set a raster scan, a radial scan, a cross scan, a circle scan, a Lissajous scan (scanning along a Lissajous curve) or the like as the scan pattern. Note that the imaging range at a site of interest such as the optic nerve head, the macula, or a blood vessel may be set on the examination parameter selection screen. In this case, the drive controlling unit 22 can control the X-scanner 114-1 and the Y-scanner 114-2 or the fixation lamp 106 according to the setting.

In step S603, the drive controlling unit 22 controls the stage unit 150 to move the optical head unit 100 to the initial alignment position. At this time, a screen for tomographic image imaging that is exemplified in FIG. 4 is displayed on the display unit 40. In this step, the anterior ocular segment image 401 and the fundus front image 402 are displayed. Note that, the initial alignment position may be stored in the storage 27.

Figure 7:
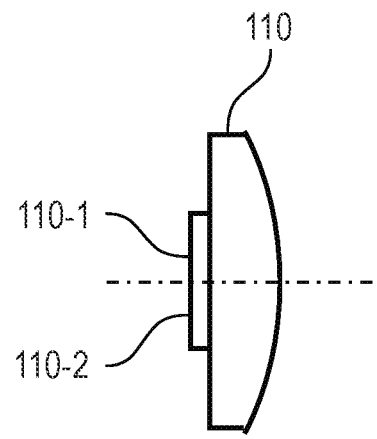
FIG. 7 is a view illustrating an example of a prism lens which has an image splitting prism.

Next, in step S604, the first alignment unit 24 performs first alignment processing, and the drive controlling unit 22 moves the optical head unit 100 based on positional information determined by the first alignment processing. Here, the operating principles of the first alignment processing according to the present embodiment will be described with reference to FIG. 7 and FIG. 8. FIG. 7 is a detailed view of an example of the prism lens 110 having an image splitting prism that divides the light flux at a position conjugate with the anterior ocular segment of the eye to be examined E.

Figure 8:
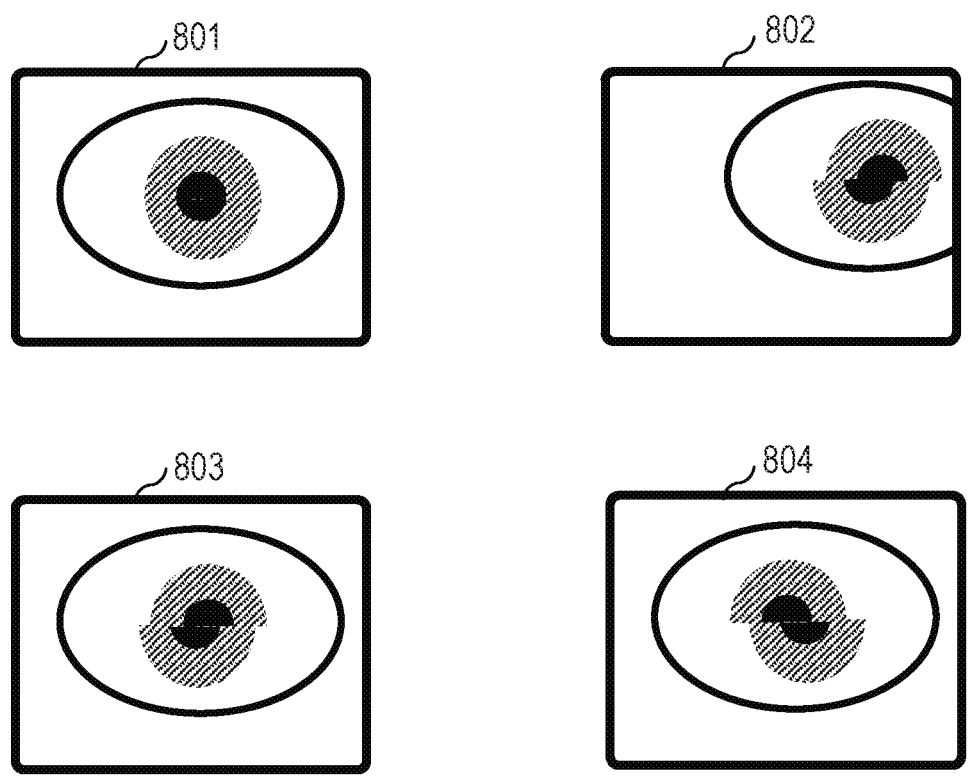
FIG. 8 is a view illustrating an example of anterior ocular segment images which were imaged using an infrared CCD.

FIG. 8 illustrates examples of anterior ocular segment images that were imaged using the infrared CCD 112.

As illustrated in FIG. 7, Fresnel prisms 110-1 and 110-2 are provided in the prism lens 110. Note that, the prism lens 110 is arranged at a position such that the Fresnel prisms 110-1 and 110-2 are conjugate with the anterior ocular segment of the eye to be examined E. Further, the surface of the prism lens 110 on the opposite side to the Fresnel prisms 110-1 and 110-2 (surface on the infrared CCD 112 side) is a spherical surface, and the prism lens 110 serves as a field lens with respect to the anterior ocular segment of the eye to be examined E. Therefore, the lens 111 that is arranged to the rear of the prism lens 110 can be reduced in size.

Here, the positional relation between the optical head unit 100 and the eye to be examined E, that is, a case where the alignment position is at the ideal position with respect to the first alignment processing will be described. In this case, the light flux from the anterior ocular segment of the eye to be examined E forms an image once on the Fresnel prisms 110-1 and 110-2 of the prism lens 110, and the image is then split due to the prism effect. However, because the imaging surface of the infrared CCD 112 is also conjugate with the Fresnel prisms 110-1 and 110-2, an anterior ocular segment image which is imaged using the infrared CCD 112 will appear as illustrated by an anterior ocular segment image 801 in FIG. 8. In the anterior ocular segment image 801, an image of the anterior ocular segment is at the center of the image, and the upper half and the lower half of the pupil image are aligned with each other.

In contrast, in a case where the alignment position is not at the ideal position in all of the XYZ directions, the anterior ocular segment image will appear as illustrated by an anterior ocular segment image 802. In the anterior ocular segment image 802, the image of the anterior ocular segment is at a position that deviates from the center of the image, and the upper half and the lower half of the pupil image are also out of alignment with each other. Further, in a case where the alignment position is at the ideal position in the X and Y directions, the image that is imaged will appear as illustrated by an anterior ocular segment image 803 when the alignment position is too far in the Z direction, and will appear as illustrated by an anterior ocular segment image 804 when the alignment position is too near in the Z direction. In the anterior ocular segment image 803 and the anterior ocular segment image 804, although the image of the anterior ocular segment is at the center of the image, the upper half and the lower half of the pupil image are out of alignment with each other, and the misalignment directions in the anterior ocular segment image 803 and the anterior ocular segment image 804 are the opposite directions to each other.

As described above, in the present embodiment, the prism lens 110 is provided at a position that is substantially conjugate with the anterior ocular segment of the eye to be examined E on the optical path L3 for observation of the anterior ocular segment. Therefore, by detecting the pupil position of the eye to be examined E from an anterior ocular segment image which was imaged using the infrared CCD 112, the first alignment unit 24 can know the alignment position relation between the optical head unit 100 and the eye to be examined E. The drive controlling unit 22 can align the optical head unit 100 with respect to the eye to be examined E by moving the optical head unit 100 to a position determined by the first alignment unit 24.

Here, the details of the first alignment processing according to the present embodiment in step S604 will be described referring to FIG. 6B. Upon the first alignment processing being executed in step S604, in step S641, the obtaining unit 21 obtains an output signal from the infrared CCD 112, and the image generating unit 23 generates and obtains an anterior ocular segment image.

In step S642, the first alignment unit 24 analyzes the obtained anterior ocular segment image and extracts the pupil region. Thereafter, the first alignment unit 24 quantifies the centroid position of the pupil image in the extracted pupil region as a position on the imaging surface of the infrared CCD 112.

Further, in step S643, the first alignment unit 24 quantifies the divided amount of the pupil image in the extracted pupil region. More specifically, the first alignment unit 24 binarizes the imaged anterior ocular segment image, and extracts, from the binarized image, a linear component as the position where the image structure was divided. The first alignment unit 24 then extracts the respective positions of end portions of the divided pupil image which are equal distances from the extracted linear component, and quantifies the degree of deviation of the positions of the end portions of the pupil image.

In step S644, the first alignment unit 24 determines information pertaining to a position (first alignment position) at which the optical head unit 100 should be disposed with respect to the eye to be examined E based on the pupil centroid position determined in step S642 and the divided amount determined in step S643. In the present embodiment, as the information pertaining to the first alignment position, the first alignment unit 24 determines movement amounts in the XYZ directions of the optical head unit 100 to the first alignment position. In step S645, the drive controlling unit 22 controls the stage unit 150 to move the optical head unit 100 based on the determined movement amount. When the optical head unit 100 has moved to the position determined in step S644, the processing transitions to step S605.

Note that, the above method for obtaining information pertaining to the position at which the optical head unit 100 should be disposed in the XYZ directions with respect to the eye to be examined E is one example. The first alignment unit 24 may determine information pertaining to the position at which the optical head unit 100 should be disposed in the XYZ directions with respect to the eye to be examined E by another known arbitrary method.

For example, the first alignment unit 24 may analyze an anterior ocular segment image in which a bright spot image was projected and imaged, detect a predetermined region including the bright spot, and determine a position in the X and Y directions at which the optical head unit 100 should be disposed so that the predetermined region falls within a predetermined alignment range in the anterior ocular segment image. Note that, the predetermined region in question is not limited to a region that includes the bright spot, and may be a region on which another index was projected, or may be a region in which the pupil image appears as described above. Further, the first alignment unit 24 may determine a position in the Z direction at which the optical head unit 100 should be disposed so that the contrast of a predetermined region in the anterior ocular segment image is maximized. Note that, the predetermined region in question may be the same as the predetermined region mentioned above.

Furthermore, the first alignment unit 24 may determine information pertaining to the position at which the optical head unit 100 should be disposed by adopting a configuration in which there are a plurality of stages, such as two stages that consist of a rough alignment and a fine alignment. For example, the first alignment unit 24 may determine a position in the Z direction at which the optical head unit 100 should be disposed based on a split index image, and thereafter determine a more exact position in the Z direction at which the optical head unit 100 should be disposed so that the contrast of a predetermined region in the anterior ocular segment image is maximized.

Next, in step S605, the first alignment unit 24 performs focus adjustment based on a fundus front image obtained using the optical head unit 100 disposed at the first alignment position. More specifically, the obtaining unit 21 obtains an output signal from the CCD 105 of the optical head unit 100 disposed at the first alignment position, and the image generating unit 23 generates a fundus front image based on the output signal. The first alignment unit 24 obtains information pertaining to the position of the lens 107 at which the intensity in the fundus front image is highest. Here, in a case where the lens 107 in the optical system for fundus observation and the lens 115 in the OCT optical system are operate in association with each other, the first alignment unit 24 can be caused to operate in association with the lens 107 that obtained positional information and can obtain information pertaining to the position at which the lens 115 of the OCT optical system should be disposed. Further, when the correspondence between the lens 107 in the optical system for fundus observation and the lens 115 in the OCT optical system is known, the first alignment unit 24 can determine the position at which the lens 115 of the OCT optical system should be disposed based on the position of the lens 107. When the positions at which the lenses 107 and 115 should be disposed have been obtained by the first alignment unit 24, the drive controlling unit 22 moves the lenses 107 and 115 to the positions determined by the first alignment unit 24.

Note that, the first alignment unit 24 may determine information pertaining to the position at which the lens 115 should be disposed based on a tomographic image generated by the image generating unit 23. In this case, the first alignment unit 24 can determine the position of the lens 115 at which the intensity in the tomographic image is highest. Therefore, the first alignment unit 24 may determine the position at which the lens 107 should be disposed based on a fundus front image, and may determine the position at which the lens 115 should be disposed based on a tomographic image.

Further, the first alignment unit 24 may adjust the focus in a plurality of stages, such as two stages that consist of a rough focus adjustment and a fine focus adjustment. For example, the first alignment unit 24 may determine the position at which the lens 115 that is operated in association with the lens 107 should be disposed based on a fundus front image, and thereafter determine a more exact position at which the lens 115 should be disposed based on a tomographic image.

Note that, the above method for adjusting the fundus focus is one example. The first alignment unit 24 may determine information pertaining to the position at which the lenses 107 and 115 should be disposed with respect to the eye to be examined E by another known arbitrary method. For example, the first alignment unit 24 may detect a predetermined region in a fundus front image or a tomographic image, and determine the positions of the lenses 107 and 115 at which the contrast in the predetermined region is highest. For example, a vascular zone, an optic nerve head, a macular area or an abnormal site (lesion region) may be included as the predetermined region. Note that, the predetermined region may be set according to an instruction of the operator.

Note that, when detecting for an abnormal site, rule-based detection processing may be performed. Here, the term "rule-based processing" refers to processing that utilizes known regularity such as, for example, the regularity of the shape of the retina. Further, in a case where an abnormal site is detected, the display controlling unit 28 may, for example, with respect to a region of the detected abnormal site, cause a region of interest (ROI) that shows the relevant region of the abnormal site to be displayed in a superimposed manner on a fundus front image displayed on the display unit 40.

In step S606, the first alignment unit 24 performs CG adjustment based on a tomographic image obtained using the optical head unit 100 that is disposed at the first alignment position. More specifically, the obtaining unit 21 obtains an interference signal that is output from the line sensor 184, and the image generating unit 23 generates a tomographic image based on the interference signal. The first alignment unit 24 can detect a predetermined region (for example, a predetermined retinal layer such as the RPE layer) in the tomographic image, and can obtain information pertaining to the position of the mirror 119 at a time that an image of the predetermined region is located at a predetermined depth position in the tomographic image. Here, apart from a retinal layer such as the RPE layer, for example, a vitreous body region, a vitreous body pocket region, a choroid region, a sclera region, or an abnormal site (lesion region) may be included as the predetermined region. Note that, the predetermined region may be set according to an instruction of the operator. When the position at which the mirror 119 should be disposed has been obtained by the first alignment unit 24, the drive controlling unit 22 moves the mirror 119 to the position determined by the first alignment unit 24.

Note that, when detecting for an abnormal site, rule-based detection processing may be performed. Further, in a case where an abnormal site is detected, the display controlling unit 28 may, for example, with respect to a region of the detected abnormal site, cause a region of interest that shows the relevant region of the abnormal site to be displayed in a superimposed manner on a tomographic image displayed on the display unit 40.

Note that, the above method for adjusting the coherence gate position is one example. For example, as information pertaining to the position at which the mirror 119 should be disposed, the first alignment unit 24 can determine a position at which a signal-to-noise ratio or an intensity value (total intensity value or the like) of a tomographic image becomes equal to or greater than a predetermined threshold or becomes a maximum value. Furthermore, as information pertaining to the position at which the mirror 119 should be disposed, the first alignment unit 24 can also determine a position that is offset by a predetermined amount from the relevant obtained position.

In step S607, the evaluating unit 26 performs an evaluation of the tomographic image obtained using the optical head unit 100 disposed at the first alignment position on which the focus adjustment and CG adjustment were performed. More specifically, the obtaining unit 21 obtains an interference signal output from the line sensor 184 after the focus adjustment and the CG adjustment were performed, and the image generating unit 23 generates a tomographic image based on the interference signal. The evaluating unit 26 determines a Q index value as a first evaluation value with respect to the image quality of the tomographic image.

In step S608, the evaluating unit 26 determines whether or not the first evaluation value obtained in step S607 is equal to or greater than a threshold. If the evaluating unit 26 determines that the first evaluation value is equal to or greater than the threshold, it is assumed that necessary and sufficient image quality was obtained, and the alignment processing is ended and the processing transitions to step S615. In step S615, actual imaging is performed using the optical head unit 100 on which the alignment was performed. Here, the term "actual imaging" means imaging pertaining to measurement relating to the fundus of the eye to be examined, and this imaging is referred to as "actual imaging" to distinguish it from the imaging in the preparatory stage. Note that, at this time, the display controlling unit 28 may display information to the effect that second alignment processing will not be performed on the display unit 40.

On the other hand, in step S608, if the evaluating unit 26 determines that the first evaluation value is lower than the threshold, the processing transitions to step S609. In step S609, the second alignment unit 25 carries out second alignment processing.

Here, the details of the second alignment processing in step S609 will be described with reference to FIG. 6C. When the second alignment processing is started, first, in step S691, an anterior ocular segment image is obtained. Specifically, the obtaining unit 21 obtains an output signal from the infrared CCD 112 of the optical head unit 100 that is disposed at the first alignment position and on which the focus adjustment and CG adjustment were performed, and the image generating unit 23 generates and obtains an anterior ocular segment image.

In step S692, using a learned model that is described later, the second alignment unit 25 determines information pertaining to a position (second alignment position) at which the optical head unit 100 should be disposed with respect to the eye to be examined E from the anterior ocular segment image. Specifically, the second alignment unit 25 inputs the anterior ocular segment image to the learned model, and determines the second alignment position based on the output (inference result) from the learned model. Note that, in the present embodiment, as the information pertaining to the second alignment position, the second alignment unit 25 determines movement amounts in the XYZ directions of the optical head unit 100 to the second alignment position.

In step S693, the drive controlling unit 22 controls the stage unit 150 to move the optical head unit 100 based on the determined movement amount. Upon the optical head unit 100 moving to the position determined in step S692, the processing transitions to step S610.

In step S610, the evaluating unit 26 performs an evaluation of a tomographic image obtained using the optical head unit 100 disposed at the second alignment position. More specifically, the obtaining unit 21 obtains an interference signal output from the line sensor 184 after the optical head unit 100 is disposed at the second alignment position, and the image generating unit 23 generates a tomographic image based on the interference signal. Similarly to step S607, the evaluating unit 26 determines a Q index value as a second evaluation value with respect to the image quality of the tomographic image.

In step S611, the evaluating unit 26 compares the second evaluation value obtained in step S610 with the first evaluation value obtained in step S607. If the evaluating unit 26 determines that the second evaluation value is equal to or greater than the first evaluation value, the processing transitions to step S615. In step S615, actual imaging is performed using the optical head unit 100 aligned at the second alignment position.

On the other hand, in step S611, if the evaluating unit 26 determines that the second evaluation value is lower than the first evaluation value, the processing transitions to step S612. In step S612, the drive controlling unit 22 controls the stage unit 150 to move the optical head unit 100 to the first alignment position that was determined in step S604. Thereafter, in step S615, actual imaging is performed using the optical head unit 100 aligned at the first alignment position.

By performing the processing as described above, the optical head unit 100 is aligned at a more appropriate position with respect to the eye to be examined E. Note that, the focus adjustment processing and the CG adjustment processing may also be performed after the movement of the optical head unit 100 in step S693 and step S612.

Further, the actual imaging in step S615 may be performed in accordance with an instruction of the operator. In this case, the processing from steps S604 to S612 may be repeated at predetermined time intervals until an instruction to perform actual imaging is given by the operator. Further, the display controlling unit 28 may display an anterior eye image, a fundus frontal image, and a tomographic image which are obtained at any time on the display unit 40 as moving images until an instruction to perform actual imaging is given. Hereinafter, such a display screen is referred to as a preview screen.

Note that, tracking processing that moves the optical head unit 100 to track movement of the subject while measurement is in progress may be performed. In this case, as described above, by continuing to execute alignment using alignment processing that utilizes a tomographic image having image quality with a high evaluation value, even in a case where the subject moves, movement of the optical head unit 100 to an appropriate alignment position can be continued.

(Configuration of Learned Model)

Here, the learned model that is used for the aforementioned second alignment processing will be described in detail. In the second alignment processing according to the present embodiment, processing for recognizing an alignment position from an anterior ocular segment image is implemented with a neural network that learned by a machine learning process according to deep learning (deep structured learning).

Figure 9:
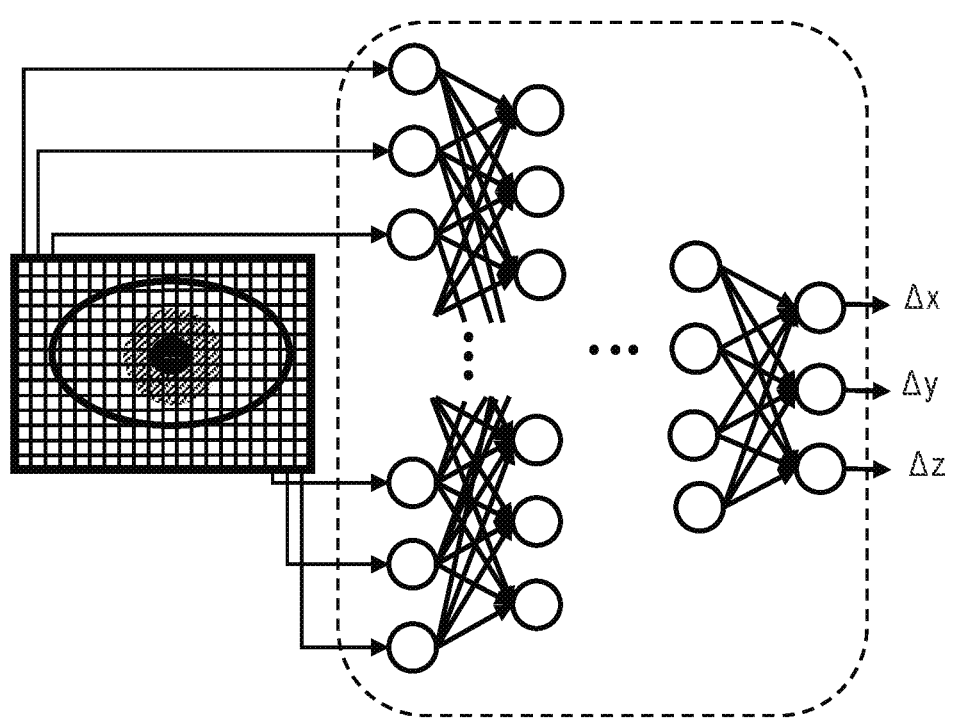
FIG. 9 is a schematic diagram of a neural network model.

FIG. 9 illustrates one example of a neural network model schematic diagram according to the present embodiment. The model schematic diagram illustrated in FIG. 9 is designed so that, with respect to image information that is two-dimensional pixel array data of an input anterior ocular segment image, the model recognizes an eye shape that was learned in advance, and outputs a deviation amount from an appropriate alignment position in the coordinate system of the optical head unit 100. Note that, three-dimensional positional information $\Delta x$, $\Delta y$ and $\Delta z$ is output as the deviation amount. The alignment information such as a deviation amount that is output is information which is based on the learning content in a machine learning process (deep learning), and the neural network according to the present embodiment learns the external shape of an eye included in anterior ocular segment image information and a feature value that represents a correlation with a position of the optical head unit 100.

In the neural network according to the basic specifications described above, flexible pattern recognition can be performed by adopting a configuration in which the layer closest to the input layer is implemented by, for example, a convolutional neural network (CNN), which is a combination of a so-called "convolutional layer" and a "pooling layer". Further, for example, the layer closest to the output layer can be implemented by a fully connected layer (not particularly illustrated in the drawing), which is suitable for optimal value operations.

As the learning method of the neural net according to the present embodiment, learning can be performed by either of so-called "supervised learning" and "reinforcement learning". When performing supervised learning, it suffices to use an anterior ocular segment image as input data, and to manually perform alignment between the eye to be examined and the optical head unit and use the manual alignment result (movement amount) as a ground truth.

Figure 11A:
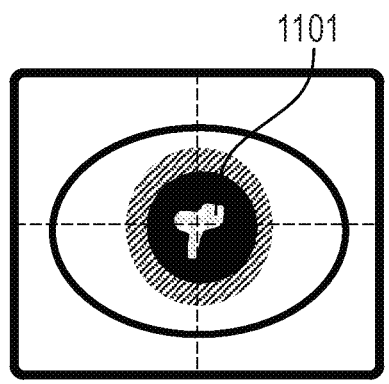
FIG. 11A is a view for describing an anterior ocular segment image at a time of learning.
Figure 11B:
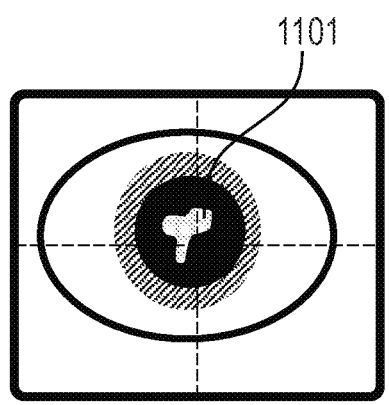
FIG. 11B is a view for describing an anterior ocular segment image at a time of learning.
Figure 11C:
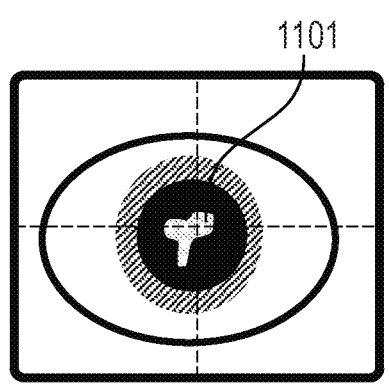
FIG. 11C is a view for describing an anterior ocular segment image at a time of learning.

Hereunder, training data of the learned model according to the present embodiment will be described with reference to FIG. 11A to FIG. 11C. FIG. 11A to FIG. 11C are views for describing an anterior ocular segment image at a time of learning. In FIG. 11A to FIG. 11C, anterior ocular segment images in a case where there is a partial opacity 1101 in the eye to be examined E are illustrated.

FIG. 11A illustrates an anterior ocular segment image in a case where, by performing the aforementioned first alignment processing, the optical head unit 100 was disposed at a position close to the ideal position in the first alignment processing with respect to the eye to be examined E. In the anterior ocular segment image illustrated in FIG. 11A, although the optical head unit 100 is disposed at a position close to the ideal position with respect to the eye to be examined E, because the opacity 1101 is present in the eye to be examined E, even if imaging is performed at the relevant position, the light flux of measuring light or the like will be scattered by the opacity 1101. Therefore, in a case where actual imaging is performed at such a position, an appropriate fundus front image or tomographic image cannot be imaged due to the opacity 1101.

Thus, in the present embodiment, the learning of a machine learning model is performed so that, by means of the second alignment processing, the optical axis of a light flux of measuring light or the like can be shifted to avoid the opacity of the eye to be examined E to thereby enable alignment of the optical head unit 100 with respect to the eye to be examined E. Therefore, in the present embodiment, as the training data pertaining to the learned model, an anterior ocular segment image is adopted as input data, and movement amounts in the XYZ directions when the optical head unit is aligned with respect to the eye to be examined so as to avoid the opacity that is present in the eye to be examined are adopted as a ground truth.

FIG. 11B illustrates an anterior ocular segment image in a case where, from the alignment position at which the anterior ocular segment image illustrated in FIG. 11A was obtained, the operator actually operated the optical head unit 100 to perform alignment so as to avoid the opacity 1101. In this case, the anterior ocular segment image after the first alignment processing illustrated in FIG. 11A is adopted as the input data of the training data, and the movement amount of the optical head unit 100 from the first alignment position to the alignment position at the time that the anterior ocular segment image illustrated in FIG. 11B was obtained is adopted as the ground truth.

Furthermore, while the optical head multiple times is being shifted in each of the XYZ directions from the first alignment position, a tomographic image may be imaged at the respective positions, and the movement amount of the optical head unit 100 at the time that the evaluation value of the tomographic image became highest may be adopted as the ground truth of the training data. The movement amount of the optical head unit 100 in this case is the movement amount from the first alignment position to the position of the optical head unit 100 at the time that the evaluation value of the tomographic image became highest. Note that, similarly to the case described above, the input data may be the anterior ocular segment image after the first alignment processing illustrated in FIG. 11A.

Note that, with regard to the training data, although a case of using data obtained when an eye to be examined E was imaged has been described, training data can also be generated using a model of an eye. In this case, a large amount of training data can be generated more efficiently. Further, with respect to the training data, by preparing and performing learning using eyes to be examined E and eye models which have opacity of various shapes, the learned model can output a movement amount by which the optical head unit 100 should be moved to avoid opacity with respect to eyes to be examined E which have opacity of various shapes. By preparing a large amount of training data in this way and causing the neural net to learn using the training data, the second alignment unit 25 can obtain information pertaining to a more appropriate second alignment position using the learned model.

Note that, thus far, a case in which opacity is present in an eye to be examined has been described in relation to a case where alignment of the apparatus with respect to an eye to be examined is to be performed by shifting the optical axis of measuring light. However, a case where alignment of the apparatus with respect to an eye to be examined is to be performed by shifting the optical axis of measuring light is not limited thereto. For example, in a diseased eye or the like, the pupil is often decentered with respect to the cornea. It is known that in a method that projects an alignment index, when alignment is performed based on an alignment index image projected onto the cornea of such kind of eye to be examined, the optical axis of the apparatus and the pupil of the eye to be examined do not match, and in a case where the pupil diameter is small, the measuring light flux may be eclipsed by the pupil. Further, if there is a large deviation in the positional relation between the apparatus and the eye to be examined, in some cases the corneal reflection light of the alignment index cannot be detected. Therefore, in these cases also, when performing various adjustment operations relating to the apparatus such as an operation to align the apparatus with respect to the eye to be examined, the operator is required to be familiar with these adjustment operations to a certain extent.

Therefore, in relation to the training data of a learned model that the second alignment unit 25 uses, for example, training data can also be prepared with respect to an eye to be examined E in which the pupil is decentered with respect to the cornea. In this case, an anterior ocular segment image may be adopted as input data of the training data, and a movement amount when the optical head unit 100 was aligned in accordance with the decentration of the pupil may be adopted as the ground truth. A model of an eye can also be used to create such learning data.

Further, information pertaining to alignment positions when alignment is appropriately performed with respect to a healthy eye may be included as training data. In this case, an anterior ocular segment image of a healthy eye may be adopted as input data of the training data, and a movement amount when the optical head unit 100 was appropriately aligned may be adopted as the ground truth. In the case of a learned model that learned using such kind of training data, the second alignment unit 25 can also obtain information pertaining to an appropriate alignment position with respect to an eye to be examined E in which there is no opacity and no decentration of the pupil. A model of an eye can also be used to create such learning data.

Note that, using these kinds of training data, learning can be performed according to the back propagation method (error back propagation method) that adjusts a weighting factor of each edge connecting together the respective nodes so that the relationship between an input layer and an output layer of each neural network is established. Specifically, first, an error between output data that is output from the output layer of the neural network according to the input data that is input to the input layer of the learning model, and training data is obtained. Note that, a configuration may be adopted so as to calculate an error between the output data from the neural network and the training data using a loss function. Next, based on the obtained error, combining weighting factors between nodes of the neural network or the like are updated using the error back propagation method so that the error becomes small. The error back propagation method is a method that adjusts combining weighting factors between the nodes of each neural network or the like so that the aforementioned error becomes small. Note that, in addition to such an error back propagation method, a combination of various known learning methods such as the so-called "stacked auto-encoder", "dropout", "noise addition", and "sparse regularization" methods may be used to improve the processing accuracy.

When data is input to a learned model that performed learning using training data of this kind, data in accordance with the design of the learned model is output. For example, data is output that has a high probability of corresponding to the data that was input, in accordance with the tendency for which the learned model was trained using the training data. In the present embodiment, when an anterior ocular segment image is input to the learned model that performed learning using the aforementioned training data, a movement amount (alignment result) for appropriately performing alignment of the optical head unit 100 with respect to the eye to be examined E is output. In particular, by using such kind of learned model, the second alignment unit 25 can also obtain information pertaining to a second alignment position such as a movement amount for appropriately performing alignment with respect to the eye to be examined E in which there is opacity or decentration of the pupil.

Here, the data that is output from the learned model will be described in more detail. For example, according to a machine learning model using the aforementioned CNN, a probability that an anterior ocular segment image which was input corresponds to respective values among a plurality of movement amounts which correspond to each of a plurality of anterior ocular segment images which were input at the time of learning is output, for example, as a probability for each of the values. Therefore, the output from the learned model is movement amounts that were adopted as output data at the time of learning that correspond to the anterior ocular segment image which was input, and values (probabilities) corresponding to the respective movement amounts.

The second alignment unit 25 refers to the probabilities and the like output from the learned model, and determines a movement amount that has a high probability of corresponding to the input anterior ocular segment image as the value that should be output. For example, the second alignment unit 25 inputs an obtained anterior ocular segment image to the learned model, and from among the plurality of movement amounts that are output from the learned model, determines the movement amount that has a higher probability than the other movement amounts to be the movement amount that should be output.

Note that, a method by which the second alignment unit 25 determines a movement amount that should be output from among a plurality of movement amounts output from the learned model is not limited to the above method. For example, the display controlling unit 28 may display the plurality of movement amounts and the probabilities of the movement amounts that were output from the learned model on the display unit 40, and based on the display, the operator may select a movement amount that the second alignment unit 25 should output. In this case, the second alignment unit 25 can determine the movement amount that should be output according to the instruction of the operator.

Further, a movement amount that the second alignment unit 25 should output from among a plurality of movement amounts output from the learned model may be determined by using another machine learning model. In this case, the machine learning algorithm may be a machine learning algorithm of a different kind to the machine learning algorithm used to obtain information pertaining to the second alignment position, and for example, Support Vector Machine, AdaBoost, a Bayesian network, or Random Forest may be used.

Note that, here a movement amount has been described as an example of information pertaining to the second alignment position that the second alignment unit 25 outputs. On the other hand, in a case where the information pertaining to the second alignment position is coordinates in an XYZ coordinate system at which the optical head unit 100 should be disposed also, it suffices to perform similar processing to determine a value that should be output from among a plurality of coordinates (positions) that are output from the learned model.

Further, in the learning method in the case of performing reinforcement learning, after performing the aforementioned first alignment processing, imaging of a tomographic image is performed while shifting the optical head unit 100 disposed at a random position by a random amount in a random direction among the XYZ directions, and evaluation of the tomographic image is then performed. Note that, an evaluation index such as the aforementioned Q index may be used for evaluation of the tomographic image. Thereafter, the optical head unit 100 is randomly moved once again, a tomographic image is obtained, and evaluation of the tomographic image is performed. Then, a difference between the evaluation values is calculated, and using the difference as a reward, learning of the neural network is performed by the error back propagation method so that the maximum reward can be obtained. Note that, the aim of the reinforcement learning may be set as, for example, arriving at the position at which the reward is maximized in the shortest time.

For example, FIG. 11A illustrates an anterior ocular segment image after the first alignment processing was performed, and FIG. 11B illustrates an example of an anterior ocular segment image in a case where, as a random direction, the optical head unit 100 was moved in the lower right direction from the first alignment position. According to one example of reinforcement learning, first, a tomographic image is imaged at this alignment position, and an evaluation value Eb of the tomographic image is obtained. Next, the optical head unit 100 is moved downward as a random direction, and moves to a position at which an anterior ocular segment image illustrated in FIG. 11C can be obtained, and a tomographic image is obtained once more and an evaluation value Ec is obtained. A difference Ec-Eb between these evaluation values is adopted as a reward.

By repeating this kind of learning operation while sequentially adjusting the randomness of the operation position, the learning model can learn an anterior ocular segment image and a feature value for outputting a moving distance of the optical head unit 100 to an appropriate alignment position corresponding thereto. It suffices to use a so-called "Q-learning algorithm", which is known, for such reinforcement learning, and a detailed description thereof will be omitted here. Note that, SARSA, a Monte Carlo method, a bandit algorithm or the like may also be used as the algorithm for reinforcement learning.

Further, in the reinforcement learning also, learning using a model of an eye may be performed. In addition, in the reinforcement learning, a learned model obtained by learning using a model of an eye in advance may be subjected to transfer learning in which learning with the human eye is additionally performed.

Note that, apart from a processing algorithm obtained by deep learning (deep structured learning) using the illustrated neural network, another processing algorithm that utilizes, for example, Support Vector Machine or a Bayesian network or the like may be applied as a processing algorithm.

Further, the prism lens 110 may be inserted onto and retracted from the optical path at both a time of learning and a time of inference in the second alignment processing based on machine learning also. However, in a case of performing alignment adjustment manually for the purpose of generating training data, it will be difficult for the examiner to perform alignment if the prism lens 110 is retracted. Therefore, when performing alignment manually, the prism lens 110 may be inserted into the optical path. For example, an anterior ocular segment image obtained at a time when the prism lens 110 was retracted from the optical path can be adopted as input data of the training data, and information pertaining to a manual alignment position in a state in which the prism lens 110 was inserted into the optical path can be adopted as a ground truth. In this case, learning of both an anterior ocular segment image obtained when there is no prism lens, and learning of information pertaining to a manual alignment position can both be achieved.

Figure 12:
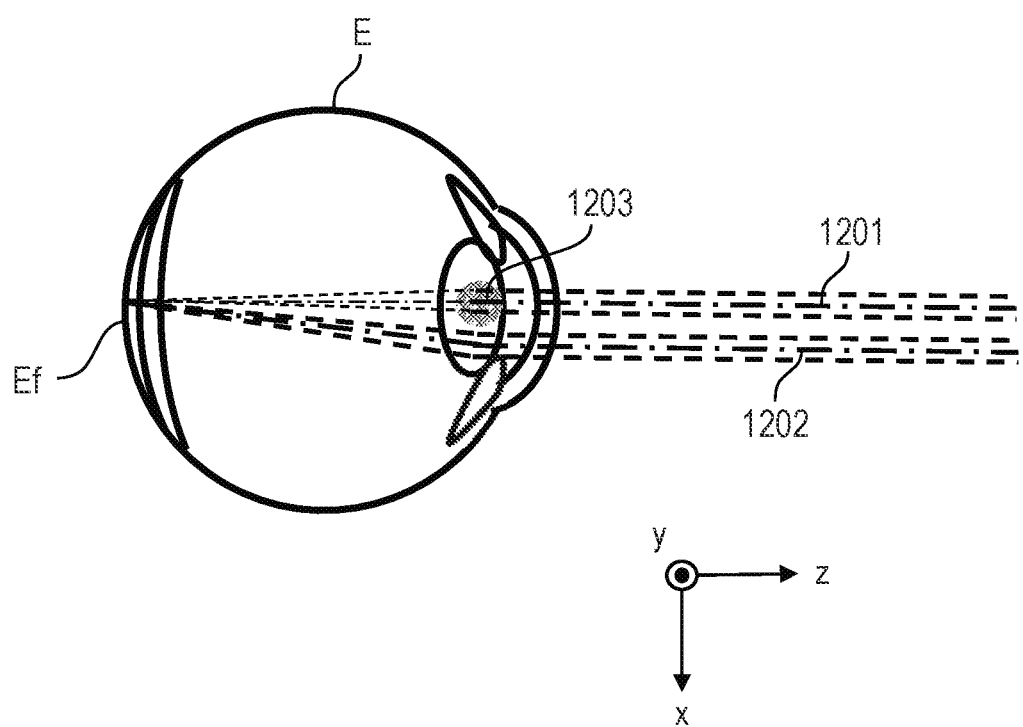
FIG. 12 is a view for describing an eye to be examined which has opacity and a light flux for observation.

Here, the advantages of alignment processing using a learned model will be described. Auto-alignment processing that avoids partial opacity of the crystalline lens due to a cataract may be mentioned as an example of the advantages. The auto-alignment processing will be described with reference to FIG. 12. FIG. 12 is a view for describing an eye to be examined that has opacity and a light flux for observation. In FIG. 12, partial opacity 1203 that is caused by degeneration of proteins or the like in the crystalline lens due to a cataract or the like is illustrated.

Here, in step S604, a light flux in a state in which the optical head unit 100 is disposed at the first alignment position with respect to the eye to be examined E is a light flux 1201. FIG. 12 illustrates an example in which the partial opacity 1203 is, in particular, at a central part of the optical path, and in this case the light flux 1201 of the measuring light for tomography is scattered by the opacity 1203 and most of the light flux 1201 does not reach the fundus Ef. Therefore, a preview image of a tomographic image that is imaged in such a state is very dark, and at the same time, the Q index value of the tomographic image is also low.

In the case of such an eye to be examined E, a skilled examiner will perform imaging after aligning the optical head unit 100 with respect to the eye to be examined E in a manner that avoids the opacity 1203. The light flux in a case where alignment was performed that avoided the opacity 1203 is denoted by reference numeral 1202. In this case, the optical head unit 100 can guide the light flux 1202 of measuring light for imaging a tomographic image to the fundus Ef while avoiding the opacity 1203. In order to avoid the opacity, auto-alignment processing that is effective for dealing with opacity can be performed by using a learned model to implement a technique whereby imaging is performed after shifting the alignment of the optical head unit 100 with respect to the eye to be examined E.

As described above, the OCT apparatus 1 according to the present embodiment is equipped with the optical head unit 100 that includes an optical system for irradiating the eye to be examined E with light and detecting return light from the eye to be examined, the first alignment unit 24, and the second alignment unit 25. The first alignment unit 24 obtains information pertaining to a first alignment position (first position) at which to dispose the optical head unit 100 with respect to the eye to be examined E, based on an image of the anterior ocular segment obtained using the optical head unit 100. The second alignment unit 25 uses a learned model obtained by learning positional information that relates to the position of the optical head unit 100 with respect to the eye to be examined E to obtain information pertaining to a second alignment position (second position), which is different from the first alignment position, at which to dispose the optical head unit 100 with respect to the eye to be examined, from an image of the anterior ocular segment obtained using the optical head unit 100. Further, the OCT apparatus 1 is configured so that information pertaining to the second alignment position can be obtained by the second alignment unit 25 after information pertaining to the first alignment position is obtained by the first alignment unit 24. Note that, the information pertaining to the first position and the second position is not limited to information pertaining to a first alignment position and a second alignment position at which the optical head unit 100 should be disposed (aligned) with respect to the eye to be examined E, and may be positional information relating to the position of the optical head unit 100 with respect to the eye to be examined E. Here, the positional information relating to the position of the optical head unit 100 with respect to the eye to be examined E may be information regarding the current position (position at the time of obtaining the image of the anterior ocular segment) of the optical head unit 100 with respect to the eye to be examined E.

Note that, the learned model is a machine learning model obtained by learning positional information of the optical head unit 100 in a case where the optical axis of the light flux from the optical head unit 100 was shifted from the centroid of the pupil of the eye to be examined E. Further, the OCT apparatus 1 is also equipped with the evaluating unit 26 for evaluating an image relating to the fundus Ef obtained using the optical head unit 100. In a case where the evaluation value for an image relating to the fundus Ef obtained at the first alignment position is lower than a threshold, the second alignment unit 25 obtains information pertaining to the second alignment position. Note that, in a case where the evaluation value for an image relating to the fundus Ef obtained at the first alignment position is equal to or greater than the threshold, information pertaining to a second position is not determined by the second alignment unit 25. Further, in the OCT apparatus 1, measurement relating to the fundus Ef of the eye to be examined E is performed at the position at which the image relating to the fundus Ef that has the higher evaluation value among the evaluation value for the image relating to the fundus Ef obtained at the first alignment position and the evaluation value for the image relating to the fundus Ef obtained at the second alignment position is obtained.

The OCT apparatus 1 is also equipped with the drive controlling unit 22 for controlling driving of the optical head unit 100. The drive controlling unit 22 controls driving of the optical head unit 100 to the first position based on information pertaining to the first position that the first alignment unit 24 obtained. Further, the drive controlling unit 22 controls driving of the optical head unit 100 to the second position based on information pertaining to the second position that the second alignment unit 25 obtained.

With this configuration, by performing the second alignment processing using a learned model, the second alignment unit 25 according to the present embodiment can recognize an appropriate alignment position from an image based on the learning contents in a machine learning process (for example, deep learning). By this means, since auto-alignment can be continuously performed, in particular, at a position that avoids opacity or a position corresponding to decentration of a pupil, the OCT apparatus 1 can perform imaging while maintaining a favorable state for an image that is obtained, even in the case of tomography for which the imaging time is comparatively long. Therefore, the complexity of an operation for adjusting an alignment position can be reduced with respect to, in particular, a diseased eye in which the corneal shape is abnormal or a diseased eye affected by a cataract or the like. Further, because auto-alignment to a position at which a good tomographic image can be imaged can be continuously performed, the imaging is simple and easy and thus the examination time is shortened, and consequently the burden on the subject can be reduced.

Note that, in the case of the second alignment processing for finding a position that avoids opacity or a position corresponding to decentration of the pupil, due to the processing load of the network of the learned model, the processing takes time compared to first alignment processing such as in step S604 that is conventionally performed. Therefore, in the present embodiment, a configuration is adopted so that the tomographic image is evaluated after the first alignment processing, and the second alignment processing is executed only in a case where the second alignment processing using the learned model is required according to the evaluation result. Therefore, in the case of an eye to be examined E that does not require the second alignment processing, the occurrence of a situation in which the time required for processing is long can be suppressed.

As another configuration, a configuration may be adopted that enables selection of the first alignment processing and the second alignment processing according to the disease of the patient. Further, a configuration may be adopted so that, by recording the alignment processing for which the evaluation value was higher together with the patient ID (identification information), the optimal alignment technique for the patient can be selectively performed when performing imaging a second time and subsequent times.

In addition, a configuration may be adopted so that information regarding the disease of a patient or the like is obtained, and for a patient for which there is a high probability that opacity such as a cataract will be recognized or the like, the first alignment processing is skipped, and alignment processing using a learned model that is the second alignment processing is performed. In other words, in the OCT apparatus 1, in a case where the eye to be examined E is a predetermined diseased eye, information pertaining to a second alignment position may be determined by the second alignment unit 25 without information pertaining to a first alignment position being determined by the first alignment unit 24. Here, the kinds of predetermined diseased eye may include at least one kind among a cataractous eye, an eye in which pupil decentration has occurred, and an eye in which miosis has occurred. In this case, by skipping the first alignment processing, the examination time can be shortened and the burden on the subject can thereby be reduced. Note that, in this case, the second alignment processing will be performed before the focus adjustment processing and the CG adjustment processing.

Here, a configuration in which the second alignment processing is performed without the first alignment processing being performed prior thereto will be described. In this case, not only an anterior ocular segment image after first alignment processing and a movement amount of the optical head unit corresponding thereto, but also an anterior ocular segment image obtained at the initial alignment position and a movement amount of the optical head unit corresponding thereto are used as training data of the learned model that is used for the second alignment processing. By this means, when performing the second alignment processing without the first alignment processing being performed, the second alignment unit 25 can obtain information pertaining to the second alignment position from an anterior ocular segment image which the optical head unit 100 obtained at the initial alignment position.

Note that, with regard to a moving image of an anterior ocular segment image displayed on the preview screen, in the case of performing the first alignment processing and the second alignment processing, these two kinds of alignment processing may be performed for each frame of the moving image, or may be performed at every predetermined number of frames of the moving image.

Further, in the case of performing the first alignment processing and second alignment processing with respect to a moving image, each processing may be ended in accordance with an instruction from the operator or may be ended automatically. In the case of automatically ending the first alignment processing and second alignment processing with respect to a moving image, for example, each processing may be ended when the Q index value of respective tomographic images obtained at the first and second alignment positions is equal to or greater than the threshold. Further, for example, these processings may be ended by, from among a plurality of alignment positions relating to images of a predetermined number of frames, taking an alignment position for which the Q index value of a tomographic image obtained at that position is highest as a final first or second alignment position. Note that, in the case of automatically ending these processings, the Q index values of tomographic images with respect to a first alignment position and a second alignment position that are determined at the time point at which each processing ends may be compared in a similar manner to step S611.

Note that, in the case of performing the first alignment processing and the second alignment processing with respect to a moving image, if the Q index value of a tomographic image obtained at each alignment position does not increase within a predetermined time period, the processing may be ended even if the Q index value is less than the threshold. Note that, in this case, on the display unit 40, the display controlling unit 28 may display information to the effect that although the Q index value is less than the threshold, the processing has been ended because a predetermined time period has elapsed.

Further, with respect to a fundus front image or a tomographic image displayed on the preview screen, in the case of performing focus adjustment processing or CG adjustment processing also, these processings may be ended in accordance with an instruction from the operator or may be ended automatically. Note that, the same processing as in the case of automatically ending the first and second alignment processing with respect to an anterior ocular segment image that is described above may be performed as the processing in the case of automatically ending the focus adjustment processing or CG adjustment processing.

Note that, with respect to a configuration that performs the second alignment processing without the first alignment processing being performed prior thereto also, the second alignment processing can be performed with respect to a moving image of an anterior ocular segment image. In this case, an anterior ocular segment image obtained at the second alignment position and a movement amount of the optical head unit corresponding thereto are also used as training data of the learned model that is used for the second alignment processing. By this means, when performing the second alignment processing without the first alignment processing being performed, the second alignment unit 25 can obtain information pertaining to the second alignment position from an anterior ocular segment image obtained by the optical head unit 100 at a second alignment position with respect to a previous anterior ocular segment image.

Note that, in the actual imaging in step S615, an image such as an en-face image or an OCTA front image may be imaged together with, or instead of, a tomographic image or a fundus front image. Here, the term "en-face image" refers to a front image generated by projecting or integrating data corresponding to a depth range that is at least a partial depth range of volume data (a three-dimensional tomographic image) obtained using light interference and that is defined based on two reference planes onto a two-dimensional plane. Note that, as a technique for projecting data corresponding to a depth range defined based on two reference planes onto a two-dimensional plane, for example, a technique can be used in which representative values of data within the relevant depth range are adopted as pixel values on a two-dimensional plane. Here, the representative values can include a value such as an average value, median value or maximum value of pixel values within a range in the depth direction of the region surrounded by the two reference planes. Further, the depth range pertaining to the en-face image may, for example, include only a range corresponding to a predetermined number of pixels in a deeper direction or a shallower direction with reference to one of the two layer boundaries relating to detected retinal layers. In addition, the depth range pertaining to the en-face image may be, for example, a range that has been changed (offset) according to an instruction of the operator from a range between the two layer boundaries relating to the detected retinal layers.

Further, the term "OCTA front image" refers to a motion contrast front image that, with respect to motion contrast data with respect to a plurality of volume data, is generated by projecting or integrating data corresponding to the aforementioned depth range on a two-dimensional plane. Here, the term "motion contrast data" refers to data indicating changes between a plurality of volume data obtained by controlling so that measuring light is scanned a plurality of times over the same region (same position) of an eye to be examined. At such time, the volume data is composed of a plurality of tomographic images obtained at different positions. The motion contrast data can then be obtained as volume data by, at respective positions that are different to each other, obtaining data showing changes between a plurality of tomographic images that were obtained at approximately the same position. Note that, a tomographic image generated with motion contrast data with respect to a plurality of two-dimensional tomographic images is also referred to as an OCTA tomographic image, and motion contrast data is also referred to as OCTA data. The motion contrast data can be obtained, for example, as a variance value or a decorrelation value between two tomographic images or between interference signals corresponding to the two tomographic images, or as a value obtained by dividing a maximum value by a minimum value (maximum value/ minimum value), and may be obtained by any known method. At such time, the two tomographic images can be obtained, for example, by controlling so that measuring light is scanned a plurality of times over the same region (same position) of the eye to be examined.

Here, on the aforementioned preview screen, an en-face image or OCTA front image corresponding to a predetermined depth range may be displayed as a moving image instead of a fundus front image. Further, on the preview screen, an OCTA tomographic image may be displayed as a moving image instead of a tomographic image.

Note that, with regard to a predetermined depth range relating to generation of an en-face image or an OCTA front image, a depth range in accordance with the result of layer segmentation processing may be set as a default depth range. However, the relevant depth range may be changed according to a user instruction performed by, for example, dragging the display form of the depth range that is displayed on the preview screen or specifying the depth range by numerical values or the like. If the depth range is changed according to an instruction of the user, the displayed en-face image or OCTA front image are updated. Note that, the layer segmentation processing may be performed by known image processing, or may be performed by using a learned model for image segmentation processing that is described later.

Further, with regard to a predetermined depth range relating to generation of an en-face image or an OCTA front image, a depth range that corresponds to a predetermined region specified by the operator for the focus adjustment processing (step S605) or the CG adjustment processing (step S606) may be set. In this case, the depth range relating to generation of an en-face image or an OCTA front image is changed in accordance with the specification of the predetermined region by the operator, and the displayed en-face image or OCTA front image is updated.

Note that, in the present embodiment, the determination regarding whether or not to perform the second alignment processing (step S608), and the tomographic image evaluation (step S607) for the purpose of the determination are performed after the first alignment processing (step S605). However, the determination regarding whether or not to perform the second alignment processing, and the tomographic image evaluation for the purpose of the determination may be performed after actual imaging at the first alignment position. In this case, actual imaging processing may be performed after the CG adjustment processing (step S606). Further, a determination regarding whether or not to perform the second alignment processing, and a tomographic image evaluation for the purpose of the determination may be performed at both a timing that is before and a timing that is after actual imaging.

In addition, although in the present embodiment, the determination regarding whether or not to perform the second alignment processing is performed automatically based on the tomographic image evaluation (step S607), the determination may be performed according to an instruction of the operator. In this case, for example, the display controlling unit 28 may cause a tomographic image that was imaged after the CG adjustment processing (step S606) to be displayed on the display unit 40, and the controlling unit 20 may accept an instruction of the operator regarding whether or not to perform the second alignment processing. Further, for example, the display controlling unit 28 may display an evaluation value determined by the tomographic image evaluation (step S607) on the display unit 40 together with the relevant tomographic image or instead of the relevant tomographic image, and the controlling unit 20 may accept an instruction of the operator regarding whether or not to perform the second alignment processing.

Note that, in the present embodiment, as a determination regarding which of the first alignment position and the second alignment position is to be adopted as the alignment position, the evaluating unit 26 performs a determination based on evaluation values of the tomographic images obtained at each of the alignment positions (step S610). On the other hand, the controlling unit 20 may perform the determination according to an instruction of the operator. In this case, for example, the display controlling unit 28 may display the tomographic images obtained at the respective alignment positions on the display unit 40, and the controlling unit 20 may accept an instruction of the operator regarding which alignment position among the first alignment position and the second alignment position is to be adopted. Further, for example, the display controlling unit 28 may display an evaluation value for the respective tomographic images on the display unit 40 together with the relevant tomographic image or instead of the relevant tomographic image, and the controlling unit 20 may accept an instruction of the operator regarding which alignment position among the first alignment position and the second alignment position is to be adopted.

Note that, in the present embodiment, after selection of the examination parameters, the optical head unit 100 is automatically moved to the initial alignment position (step S603), and thereafter the first alignment processing (step S604) is automatically started. On the other hand, the first alignment processing may be started in accordance with an instruction of the operator after the optical head unit 100 moves to the initial alignment position. Similarly, after the first alignment processing, the focus adjustment processing may be automatically started or may be started in accordance with an instruction of the operator. Likewise, after the focus adjustment processing, the CG adjustment processing (S606) may be automatically started or may be started in accordance with an instruction of the operator. Further, although in the present embodiment, the CG adjustment processing (S606) is performed after the focus adjustment processing (S605), the CG adjustment processing may be performed before the focus adjustment processing or may be performed in parallel with the focus adjustment processing.

Note that, in the present embodiment, in the first alignment processing, information pertaining to a first alignment position in the Z direction is obtained based on a split image obtained using the prism lens 110. On the other hand, in a case where the prism lens 110 is not used, the first alignment unit 24 can also obtain information pertaining to a first alignment position in the Z direction based on the amount of blurring in an anterior ocular segment image. Further, the first alignment unit 24 may perform the first alignment processing using a plurality of anterior ocular segment images obtained using a plurality of cameras provided outside the optical axis. In this case, the first alignment unit 24 can ascertain the position in the depth direction of the optical head unit 100 with respect to the eye to be examined E based on the plurality of anterior ocular segment images.

Further, in the present embodiment, as alignment processing between the eye to be examined E and the optical head unit 100, the optical head unit 100 is moved with respect to the eye to be examined E. On the other hand, the alignment processing between the eye to be examined E and the optical head unit 100 may be performed by moving the eye to be examined E with respect to the optical head unit 100. In this case, the information pertaining to the first alignment position which the first alignment unit 24 obtains and the information pertaining to the second alignment position which the second alignment unit 25 obtains is positional information pertaining to the position of the eye to be examined E with respect to the optical head unit 100. Here, the information pertaining to the first alignment position and the information pertaining to the second alignment position of the eye to be examined E may be coordinates in an XYZ coordinate system at which the eye to be examined E should be aligned, or may be a movement amount of the eye to be examined E. Further, the aforementioned information pertaining to the first position and second position is not limited to information pertaining to a first alignment position and a second alignment position at which the eye to be examined E should be aligned with respect to the optical head unit 100, and may be information relating to the eye to be examined E with respect to the optical head unit 100. Here, the information relating to the eye to be examined E with respect to the optical head unit 100 may be information regarding the current position (position at the time of obtaining the image of the anterior ocular segment) of the eye to be examined E with respect to the optical head unit 100.

In the case of moving the eye to be examined E with respect to the optical head unit 100 to perform alignment processing between the eye to be examined E and the optical head unit 100, for example, alignment processing may be performed by moving the face receiving unit 160, against which the forehead or chin of the subject is pressed, with respect to the optical head unit 100. In this case, drive control of the face receiving unit 160 by the drive controlling unit 22 may include movement in the XYZ directions of the face receiving unit 160 itself with respect to the optical head unit 100. In this case, the first alignment position or second alignment position may be coordinates (a position) in the XYZ coordinate system of the face receiving unit 160 (supporter) that supports the face of the subject. Therefore, positional information pertaining to the eye to be examined E that corresponds to information pertaining to the first alignment position or information pertaining to the second alignment position may be coordinates in the XYZ coordinate system at which the face receiving unit 160 should be disposed or may be movement amounts in the XYZ directions.

Further, in this case, with respect to the training data of a learned model which the second alignment unit 25 uses, an anterior ocular segment image can be adopted as the input, and movement amounts in the XYZ directions of the face receiving unit 160 when the eye to be examined is aligned with respect to the optical head unit so as to avoid opacity present in the eye to be examined E can be adopted as ground truth. In addition, the method for generating the training data and the like may be the same as in the case of the information for the training data described above, except that movement amounts in the XYZ directions when the eye to be examined E is aligned with respect to the optical head unit 100 are used.

The alignment processing may also be both drive control of the optical head unit 100 and drive control of the face receiving unit 160, and the drive control of the optical head unit 100 may include a part of the movement in the XYZ directions, and the drive control of the face receiving unit 160 may include the remaining movement in the XYZ directions. Thus, these drive controls may be of any kind as long as the drive control is drive control of an optical member that changes the positional relation between the optical head unit 100 and the eye to be examined E. Note that, it suffices that the training data used to obtain the second alignment position is training data that corresponds to the drive control used for the second alignment processing, and for example both a movement amount of the optical head unit 100 and a movement amount of the face receiving unit 160 may be used as the ground truth of the training data. Further, in the respective modifications to be described later, likewise, alignment processing may be performed by at least one of drive control of the optical head unit 100 and drive control of the face receiving unit 160. In this case also, it suffices that the training data of the learned model used for the second alignment processing is training data that corresponds to the drive control used in the second alignment processing.

Note that, the drive control of the optical head unit 100 may include movement in the XYZ directions of the optical head unit 100 itself with respect to the stage unit (base unit). Further, at least one part of the measurement optical system included in the optical head unit 100 may include, for example, each optical member on the eye to be examined E side from one part of the optical fiber 117-2, and a separate stationary housing may include each optical member on the OCT optical system side from the one part of the optical fiber 117-2. Furthermore, at least one part of the measurement optical system may include, for example, each optical member on the eye to be examined E side from one part of the optical fiber 117-4, and a separate stationary housing or the stage unit (base unit) may include each optical member from the one part of the optical fiber 117-4 to the line sensor 184.

In addition, in the present embodiment, focus adjustment processing is performed using the lens 107 in the optical system for fundus observation and the lens 115 in the OCT optical system. On the other hand, focus adjustment processing may be performed using a configuration referred to as a "Badal optical system" which changes the optical path length of measuring light by movement of mirrors or the like. The Badal optical system may be configured so that the optical path length of measuring light can be adjusted by, for example, mounting two mirrors which are arranged so as to deflect light approximately 90° on a motor-driven stage, and moving the motor-driven stage in the optical axis direction of the measuring light.

Note that, a Badal optical system may be disposed on a common optical path of the optical system for fundus observation and the OCT optical system, or may be disposed separately in these optical systems. Further, a focusing lens may be disposed in one optical system among the optical system for fundus observation and the OCT optical system, and a Badal optical system may be disposed in the other optical system. In addition, a Badal optical system may be disposed on a common optical path of the optical system for fundus observation and the OCT optical system, and a focusing lens may be disposed on at least one common optical path of the optical system for fundus observation and the OCT optical system. Note that, the configuration of the Badal optical system is not limited to the configuration described above, and it suffices that the Badal optical system has a configuration that can change the optical path length of measuring light by movement of a mirror or the like.

Further, hereinafter, an optical system used for focus adjustment processing, including a focusing lens and a Badal optical system, is referred to as a "focusing optical system". Note that, in the respective modifications described later, focus adjustment processing may be performed using a Badal optical system instead of or in addition to a focusing lens.

Modification 1

In Embodiment 1, an anterior ocular segment image is adopted as input data with respect to training data for a learned model that the second alignment unit 25 uses. On the other hand, a transillumination image which is an image in which opacity of the eye to be examined E is easier to confirm may be adopted as input data of the training data.

The term "transillumination image" refers to an image of a pupil region illuminated by reflected light from the fundus Ef after the eye to be examined E is irradiated with light. A transillumination image may be generated, for example, by the image generating unit 23 in accordance with an output signal that is received when, in the optical head unit 100, the prism lens 110 is removed from the optical path, an unshown light source for transillumination observation is turned on, and reflected light from the eye to be examined E is received by the infrared CCD 112. Note that, the foregoing configuration for imaging a transillumination image is one example, and the configuration for imaging a transillumination image may be arbitrarily designed according to a desired configuration.

In a transillumination image, an opaque portion of the eye to be examined E appears as a shadow, and that portion has a low intensity. Therefore, by using a transillumination image, it is easier to ascertain an opaque portion of the eye to be examined E. Therefore, in Modification 1, a transillumination image is used as the input data of the training data for the learned model which the second alignment unit 25 uses. Note that, with respect to the ground truth, similarly to Embodiment 1, movement amounts (vectors) in the XYZ directions when the optical head unit 100 is aligned with respect to the eye to be examined E so as to avoid opacity of the eye to be examined E may be used as the ground truth.

Further, regarding the learned model that the second alignment unit 25 uses, even when performing reinforcement learning, the learned model may be the same as in the learning method according to Embodiment 1, except for the use of a transillumination image as input data. In this case also, a learned model obtained by learning using a model of an eye in advance may be subjected to transfer learning in which learning with the human eye is additionally performed.

Figure 6C:
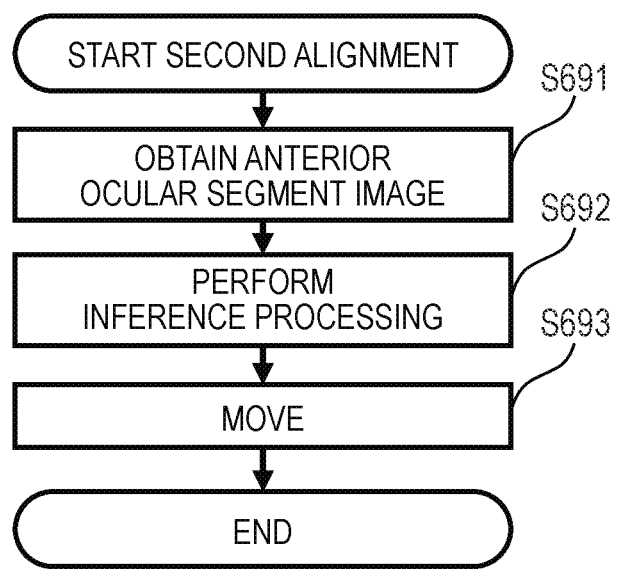
FIG. 6C is a flowchart illustrating second alignment processing.

In the case of using a learned model which performed such learning, in step S691 of the series of processing illustrated in FIG. 6C, a transillumination image is obtained instead of an anterior ocular segment image by the obtaining unit 21 and the image generating unit 23. Further, in step S692, the second alignment unit 25 adopts the transillumination image obtained in step S691 as input data, and obtains information pertaining to the second alignment position from the transillumination image using the learned model.

Even with such a configuration, a similar effect as the effect of Embodiment 1 can be obtained. Further, in a transillumination image, an opaque portion can be imaged more clearly compared to an anterior ocular segment image. Therefore, it is considered that by adopting a transillumination image as the input, the learned model can extract and process a feature value of an opaque portion more exactly. For this reason, it can be expected that the second alignment processing can be performed with greater accuracy by using a transillumination image as input data.

Note that, the input data of the learned model which the second alignment unit 25 uses may be both an anterior ocular segment image and a transillumination image. In this case, an anterior ocular segment image and a transillumination image can be adopted as the input data of the training data, and movement amounts in the XYZ directions when the optical head unit 100 is aligned with respect to the eye to be examined E so as to avoid opacity of the eye to be examined E can be adopted as the ground truth of the training data. Further, reinforcement learning may be performed. In the case of performing reinforcement learning, the learning method may be the same as the learning method according to Embodiment 1, except for the use of an anterior ocular segment image and a transillumination image as input data. Further, in this case also, a learned model obtained by learning using a model of an eye in advance may be subjected to transfer learning in which learning with the human eye is additionally performed.

Note that, similarly to the anterior ocular segment image, a transillumination image used in the present modification may be a moving image.

Modification 2

Although in Embodiment 1, a CNN was used as a machine learning model for image recognition, image data may be analyzed using a recurrent neural network (RNN) or the like. For example, on the aforementioned preview screen, an anterior ocular segment image, a fundus front image and a tomographic image are updated at any time as moving images. Therefore, by using a neural network which handles time-series information, such as an RNN, the tendency of changes in an image can be used as a feature value.

Here, as another example of the machine learning model according to the Embodiment 1, an RNN that is a neural network that handles time-series information will be described with reference to FIG. 13A and FIG. 13B. Further, a long short-term memory (hereinafter referred to as an "LSTM"), which is a kind of RNN, will be described with reference to FIG. 14A and FIG. 14B.

Figure 13A:
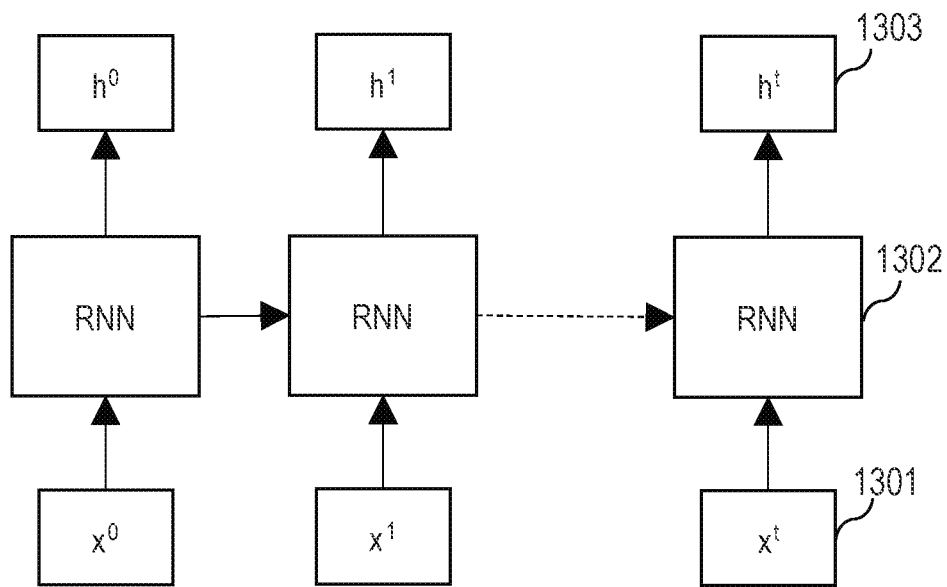
FIG. 13A is a view for describing an RNN.

FIG. 13A illustrates a configuration of an RNN that is a machine learning model. An RNN 1302 illustrated in FIG. 13A has a loop structure in the network, and when image information $x^t$ 1301 of an anterior ocular segment image is input at time t, the RNN 1302 outputs data $h^t$ 1303. Since the RNN 1302 has a loop function in the network, the state at the current time can be taken over to the next state, and hence time-series information can be handled.

Figure 13B:
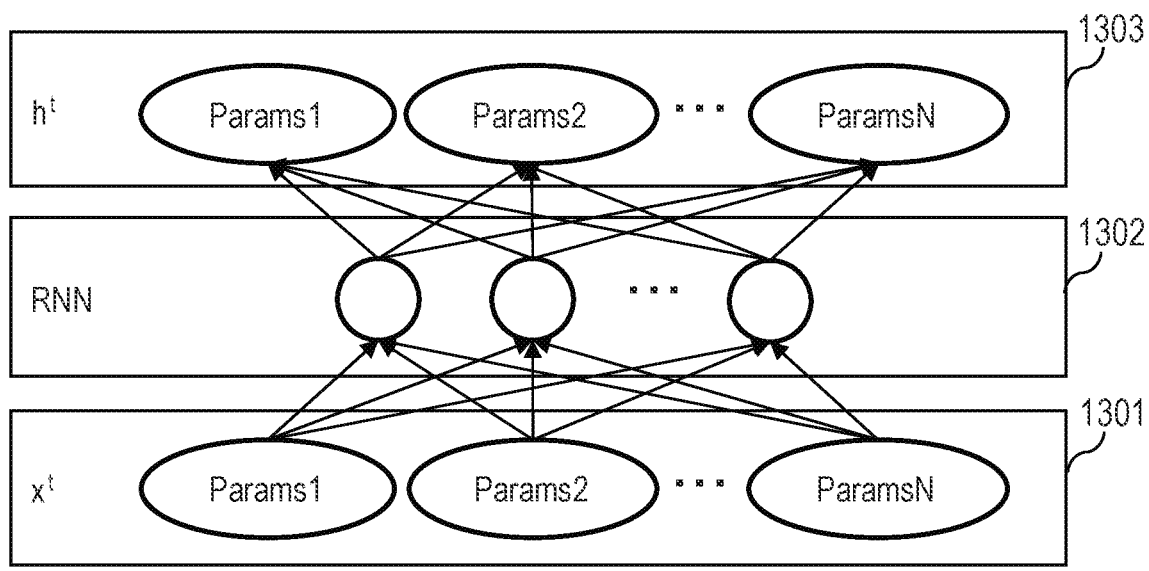
FIG. 13B is a view for describing an RNN.

FIG. 13B illustrates an example of the input/output of parameter vectors at time t. Data relating to parameters (Params 1 to Params N) of N pieces of two-dimensional pixel array data relating to an anterior ocular segment image can be included in the image information $x^t$ 1301. Further, N estimated values (for example, Params 1 to Params N) corresponding to the input data can be included in the data $h^t$ 1303 output by the RNN 1302. In this case, the second alignment unit 25 may determine a deviation amount to the second alignment position or the like based on the N estimated values that are output.

Figure 14A:
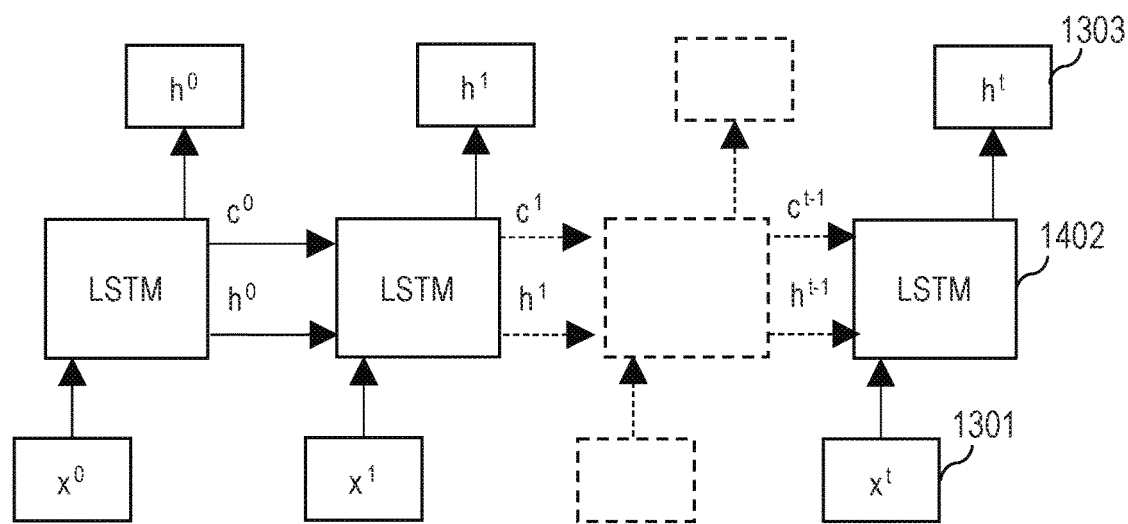
FIG. 14A is a view for describing an LSTM.

However, since the RNN cannot handle long-term information during back propagation. In this regard, the LSTM may be used as a machine learning model which handles long-term information. The LSTM can learn long-term information by providing a forget gate, an input gate, and an output gate. FIG. 14A illustrates a structure of the LSTM. In an LSTM 1402, information that the network takes over at the next time t is an internal state $c^{t-1}$ of the network called a cell and output data h". Note that lowercase letters (c, h, x) in the figure represent vectors.

Figure 14B:
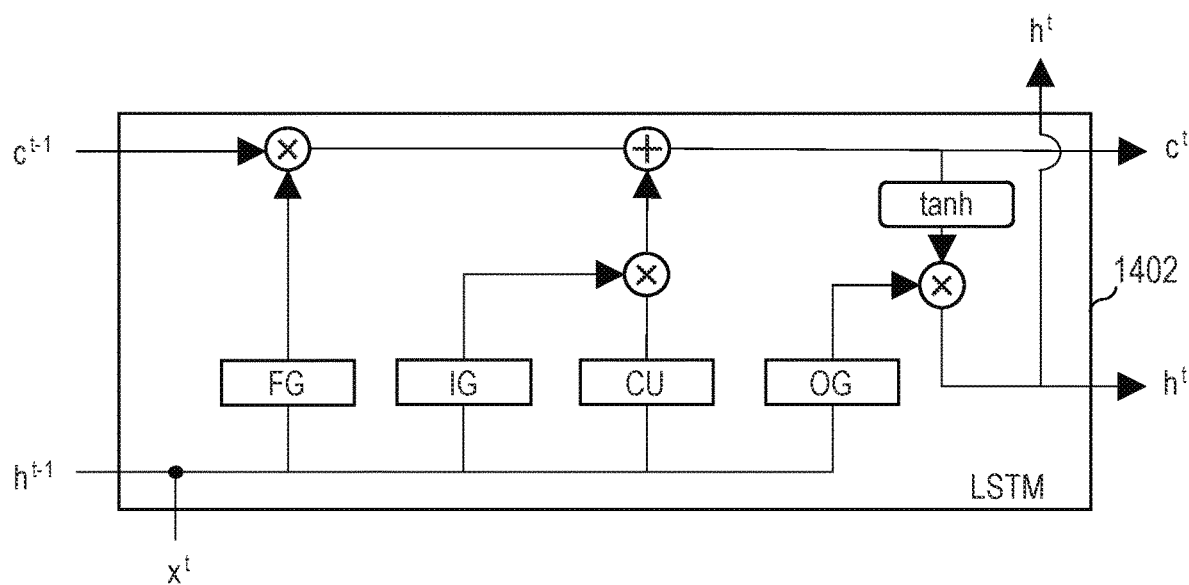
FIG. 14B is a view for describing an LSTM.

Next, the LSTM 1402 is illustrated in detail in FIG. 14B. A forget gate network FG, an input gate network IG and an output gate network OG are illustrated in FIG. 14B, and each of these is a sigmoid layer. Therefore, a vector in which each element has a value from 0 to 1 is output. The forget gate network FG determines how much past information is held, and the input gate network IG determines which value is to be updated. A cell update candidate network CU which is an activation function tanh layer is also illustrated in FIG. 14B. This creates a vector of new candidate values to be added to the cell. The output gate network OG selects an element of a cell candidate and selects how much information is to be transmitted at the next time.

Figure 15:
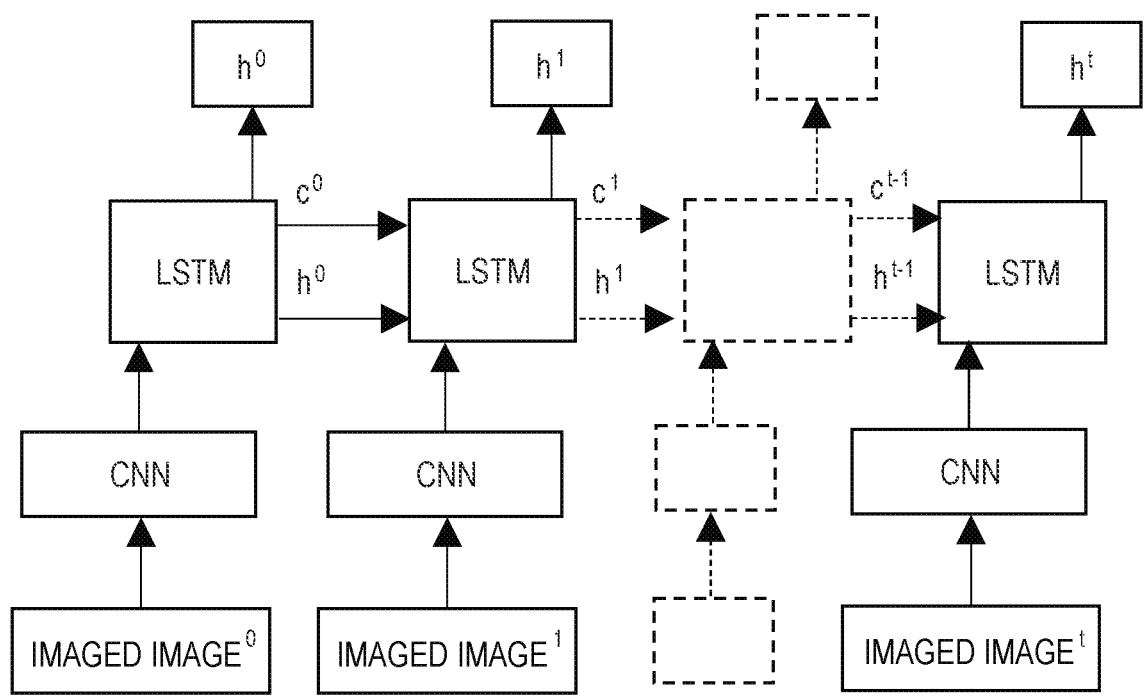
FIG. 15 is a view for describing a combination of a CNN and an LSTM.

Further, a CNN and an LSTM can also be combined and used. FIG. 15 is a schematic diagram illustrating a structure in which a CNN and an LSTM are combined. In this case, calculations with respect to an anterior ocular segment image that is the input are performed by the CNN, and a feature value that is the output is input to the LSTM. Note that, in this case, as the training data of the CNN, an anterior ocular segment image can be adopted as the input data, and various feature values that are desired can be adopted as the ground truth. Further, as the training data of the LSTM, the relevant various feature values that are desired can be adopted as the input data, and information pertaining to the second alignment position such as a deviation amount from the first alignment position can be adopted as the ground truth.

Note that, the LSTM model described above is a basic form, and the present invention is not limited to the network illustrated here. The coupling between networks may be changed. Further, a QRNN (quasi-recurrent neural network) may be used instead of an LSTM. In addition, the machine learning model is not limited to a neural network, and a machine learning model such as Boosting or Support Vector Machine or the like may be used.

Modification 3

In Embodiment 1, in the first alignment processing (step S604), the focus adjustment processing (step S605) and the CG adjustment processing (step S606), the first alignment unit 24 analyzes an image to perform the processing. On the other hand, the first alignment unit 24 may use various kinds of learned models to perform the processing in these steps. Therefore, in Modification 3, a configuration is described in which the first alignment unit 24 performs the first alignment processing (step S604), the focus adjustment processing (step S605) and the CG adjustment processing (step S606) using various kinds of learned models.

First, with regard to the first alignment processing, the first alignment unit 24 may detect a predetermined region in an anterior ocular segment image using a learned model, and determine a position in the XY directions at which the optical head unit 100 should be disposed so that the predetermined region falls within a predetermined alignment range in the anterior ocular segment image. Further, with regard to a position in the Z direction, the first alignment unit 24 may determine a position in the Z direction at which the optical head unit 100 should be disposed so that the contrast of the predetermined region in the anterior ocular segment image is maximized. Here, the predetermined region that is detected may be, for example, a pupil region or a region in which an indicator such as a bright spot was projected. Further, the predetermined region may be an opaque region in the pupil region. In this case, the first alignment unit 24, for example, may determine a position in the XY directions at which the optical head unit 100 should be disposed so that, in the region other than the opaque region, a region which is close to the center region of the pupil region falls within the predetermined alignment range.

Here, a machine learning model which the first alignment unit 24 uses for detecting a predetermined region from an anterior ocular segment image will be described. A machine learning model that performs segmentation processing on an anterior ocular segment image in pixel units, and a machine learning model that performs object recognition (detection) in ROI units are available as machine learning models which can be used for detecting a predetermined region from an anterior ocular segment image. The first alignment unit 24 may use either of these machine learning models for detecting a predetermined region from an anterior ocular segment image.

For example, a convolutional neural network (CNN) can be used as a machine learning model that performs segmentation processing on an anterior ocular segment image.

Figure 10:
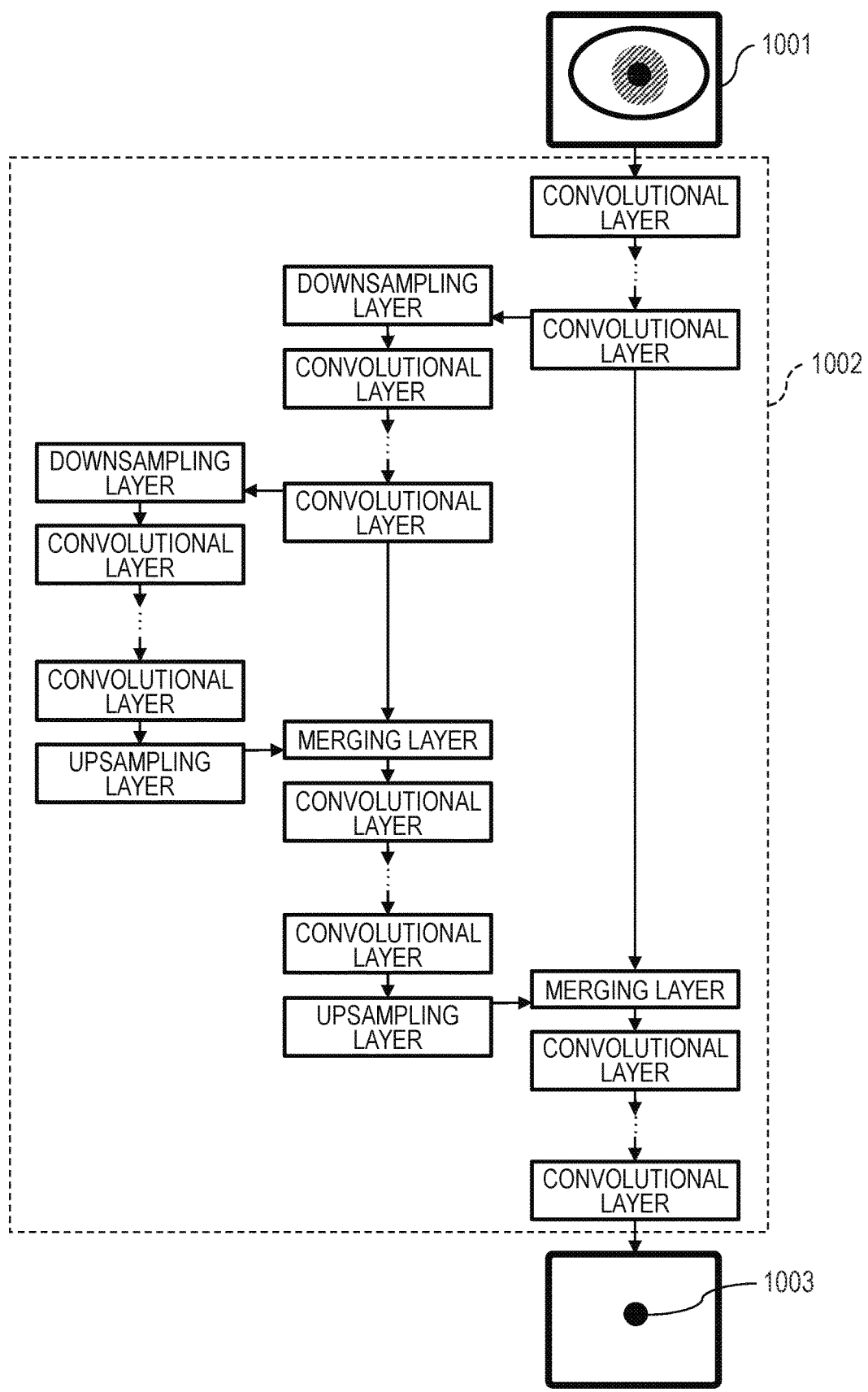
FIG. 10 is a view for describing a U-Net type CNN.

Here, an example in which a machine learning model according to the present modification is constituted by a CNN will be described with reference to FIG. 10. FIG. 10 illustrates one example of a configuration 1002 of a learned model that the first alignment unit 24 uses for detecting a predetermined region 1003 in an anterior ocular segment image 1001. Note that, for example, an FCN (fully convolutional network) or a SegNet or the like can also be used as the machine learning model according to the present modification. Further, as a machine learning model for performing object recognition, for example, RCNN (Region CNN), Fast-RCNN, or Faster-RCNN can be used. In addition, YOLO (You Only Look Once), SSD (Single Shot Detector, or Single Shot MultiBox Detector) can also be used as a machine learning model for performing object recognition in region units.

The machine learning model illustrated in FIG. 10 is constituted by a plurality of layer groups that are responsible for processing to process an input value group for output. Note that, the types of layers included in a configuration 1002 of the machine learning model are a convolutional layer, a downsampling layer, an upsampling layer, and a merging layer.

The convolutional layer is a layer that performs convolutional processing with respect to an input value group according to parameters such as the kernel size of the filters, the number of filters, the value of a stride, and the dilation value which are set. Note that, the number of dimensions of the kernel size of the filter may be changed according to the number of dimensions of an input image.

The downsampling layer is a layer that performs processing for making the number of output value groups less than the number of input value groups by thinning out or combining the input value groups. Specifically, for example, max pooling processing is available as such processing.

The upsampling layer is a layer that performs processing for making the number of output value groups greater than the number of input value groups by duplicating an input value group or adding a value interpolated from an input value group. Specifically, for example, linear interpolation processing is available as such processing.

The merging layer is a layer that performs processing that inputs, from a plurality of sources, value groups such as an output value group of a certain layer or a pixel value group constituting an image, and merges the value groups by concatenating or adding the value groups.

Note that, it is necessary to pay attention in this regard because if the settings of parameters with respect to layer groups and node groups constituting a neural network differ, in some cases the degrees to which a tendency trained based on training data is reproducible in the output data will differ. That is, in many cases, the appropriate parameters will differ according to the form at the time of implementation, and therefore parameters can be changed to preferable values as needed.

Further, there are also cases where the CNN can obtain better characteristics by changing the configuration of the CNN, and not just by using a method that changes parameters as described above. The term "better characteristics" refers to, for example, outputting information pertaining to alignment positions that has higher accuracy, the processing time becoming shorter, and the time required for training of the machine learning model becoming shorter.

Note that, the configuration 1002 of the CNN used in the present embodiment is a U-Net type machine learning model that has a function of an encoder that is composed of a plurality of levels including a plurality of downsampling layers, and a function of a decoder that is composed of a plurality of levels including a plurality of upsampling layers. In the U-Net type machine learning model, positional information (spatial information) that has been made ambiguous in a plurality of levels configured as an encoder is configured (for example, using a skip connection) so that the information can be used in levels of the same dimension (levels corresponding to each other) in a plurality of levels configured as a decoder.

Although not illustrated in the drawings, as a modification of the configuration of the CNN, for example, a batch normalization layer or an activation layer that uses a rectifier linear unit may be incorporated after the convolutional layer or the like. Features of an imaged image can be extracted through these steps of the CNN.

As the training data relating to these machine learning models, an anterior ocular segment image can be adopted as input data, and an image obtained by performing labeling (annotation) with respect to the aforementioned predetermined region of the anterior ocular segment image can be adopted as a ground truth. Note that, with respect to the ground truth of the training data, the ground truth of the training data may be an image obtained when a medical professional performed labelling with respect to an anterior ocular segment image, or may be an image that was generated based on an arbitrary labeling algorithm, or an image obtained when a medical professional modified such an image that was generated based on an arbitrary labeling algorithm or the like.

Note that, such a machine learning model may perform learning by reinforcement learning. In this case, for example, anterior ocular segment images can be labelled, and learning can be performed in a manner so that the reward given to a result that obtained an image with ideal labels with the least delay possible is greatest. Further, in this case also, a learned model obtained by learning using a model of an eye in advance may be subjected to transfer learning in which learning with the human eye is additionally performed.

In the case of detecting the predetermined region 1003 from the anterior ocular segment image 1001 using such kind of learned model, it can be expected that the predetermined region 1003 will be quickly and accurately detected.

Next, with regard to the focus adjustment processing, the first alignment unit 24 may detect a predetermined region in a fundus front image using a learned model, and may determine movement amounts of the lenses 107 and 115 so that the contrast in the predetermined region becomes the maximum contrast. Here, examples of a predetermined region to be detected may include a vascular zone, an optic nerve head, a macular area, an abnormal site (lesion region) and the like.

Here, a machine learning model which the first alignment unit 24 uses for detecting a predetermined region from a fundus front image will be described. A machine learning model that performs segmentation processing on a fundus front image in pixel units, and a machine learning model that performs object recognition (detection) in ROI units are available as machine learning models which can be used for detecting a predetermined region from a fundus front image. The first alignment unit 24 may use either of these machine learning models for detecting a predetermined region from a fundus front image. Note that, regarding the kinds of these machine learning models, the same kinds of machine learning models as the machine learning models used for detecting a predetermined region from an anterior ocular segment image can be used.

As the training data relating to these machine learning models, a fundus front image can be adopted as input data, and an image obtained by performing labeling (annotation) with respect to the aforementioned predetermined region of the fundus front image can be adopted as a ground truth. Note that, with respect to the ground truth of the training data, the ground truth of the training data may be an image obtained when a medical professional performed labelling with respect to a fundus front image, or may be an image that was generated based on an arbitrary labeling algorithm, or an image obtained when a medical professional modified such an image that was generated based on an arbitrary labeling algorithm or the like.

Note that, such a machine learning model may perform learning by reinforcement learning. In this case, for example, fundus front images can be labelled, and learning can be performed in a manner so that the reward given to a result that obtained an image with ideal labels with the least delay possible is greatest. Further, in this case also, a learned model obtained by learning using a model of an eye in advance may be subjected to transfer learning in which learning with the human eye is additionally performed.

Further, in the case of detecting an abnormal site, the first alignment unit 24 may use a generative adversarial networks (GAN) or a variational auto-encoder (VAE). For example, a DCGAN (Deep Convolutional GAN) that is composed of a generator that is obtained by learning to generate a fundus front image, and a discriminator that is obtained by learning to distinguish between a new fundus front image which the generator generated and a real fundus front image can be used as a machine learning model.

In the case of using a DCGAN, for example, the discriminator subjects an input fundus front image to encoding to convert the fundus front image into a latent variable, and the generator generates a new fundus front image based on the latent variable. Thereafter, a difference between the input fundus front image and the new fundus front image that was generated can be extracted (detected) as an abnormal site. Further, in the case of using a VAE, for example, an input fundus front image is converted into a latent variable by encoding the fundus front image using an encoder, and a new fundus front image is generated by decoding the latent variable using a decoder. Thereafter, a difference between the input fundus front image and the new fundus front image that was generated can be extracted as an abnormal site.

Note that, in a case where a plurality of abnormal sites are detected or the like, which of the detected plurality of regions to perform focus adjustment based on may be selected in accordance with an instruction of the operator. Further, in a case where an abnormal site was detected, for example, with regard to the region of the abnormal site that was detected, an ROI indicating the relevant region may be displayed in a superimposed manner on the fundus front image.

In the case of detecting a predetermined region using such kind of learned model, it can be expected that the predetermined region will be quickly and accurately detected from a fundus front image. Note that an image which is used for focus adjustment is not limited to the aforementioned fundus front image. For example, an infrared fundus front image which was imaged using a two-dimensional sensor, a fundus front image which was imaged using an SLO apparatus, an en-face image, or an OCTA front image or the like may also be used. Therefore, in the focus adjustment processing, the training data of the machine learning model to be used for detecting a predetermined region may be images that correspond to these images that are used for the focus adjustment processing.

Furthermore, with regard to the focus adjustment processing, the first alignment unit 24 may determine the movement amounts of the lenses 107 and 115 from the fundus front image by using a learned model. The machine learning model in this case may be, for example, a CNN. As the training data in this case, a fundus front image can be adopted as the input data, and with respect to the aforementioned predetermined region of the fundus front image, movement amounts (vectors) of the lenses 107 and 115 so that the contrast is maximized can be adopted as the ground truth. Note that, with regard to the ground truth of the training data, it may be a movement amount during focus adjustment that is performed according to an operation of a medical professional with respect to a fundus front image, or a movement amount during focus adjustment performed based on a known algorithm with respect to a fundus front image, or a movement amount obtained when a medical professional modified the aforementioned movement amount, or the like.

Note that, this kind of machine learning model may also perform learning by reinforcement learning. In this case, for example, fundus front images are obtained while shifting the lens 107 disposed at a random position by a random amount in a random direction among the driving directions of the lens 107, and evaluation of the fundus front images is performed. Then, a difference between the evaluation values is calculated, and using the difference as a reward, learning of the neural network is performed by the error back propagation method so that the maximum reward is obtained. Note that, the aim of the reinforcement learning may be set as, for example, arriving at the position at which the reward is maximized in the shortest time. Further, in this case also, a learned model obtained by learning using a model of an eye in advance may be subjected to transfer learning in which learning with the human eye is additionally performed.

If this kind of learned model is used, movement amounts for moving the lenses 107 and 115 to an appropriate focusing position can be quickly determined from a fundus front image.

Next, with respect to the CG adjustment processing, the first alignment unit 24 may detect a predetermined region in a tomographic image using a learned model, and determine the position of the mirror 119 at a time that an image of the predetermined region is located at a predetermined depth position in the tomographic image. Here, apart from a retinal layer such as the RPE layer, for example, a vitreous body region, a vitreous body pocket region, a choroid region, a sclera region, or an abnormal site (lesion region) may be included as the predetermined region.

A machine learning model which the first alignment unit 24 uses for detecting a predetermined region from a tomographic image will now be described. A machine learning model that performs segmentation processing on a tomographic image in pixel units, and a machine learning model that performs object recognition (detection) in region of interest units are available as machine learning models which can be used for detecting a predetermined region from a tomographic image. The first alignment unit 24 may use either of these machine learning models for detecting a predetermined region from a tomographic image. Note that, with respect to the kinds of these machine learning models, the same kinds of machine learning models as the machine learning models used for detecting a predetermined region from an anterior ocular segment image or a fundus front image can be used.

As the training data relating to these machine learning models, a tomographic image can be adopted as input data, and an image obtained by performing labeling with respect to the aforementioned predetermined region of the tomographic image can be adopted as a ground truth. Note that, with respect to the ground truth of the training data, the ground truth of the training data may be an image obtained when a medical professional performed labelling with respect to a tomographic image, or may be an image that was generated based on an arbitrary labeling algorithm, or an image obtained when a medical professional modified such an image that was generated based on an arbitrary labeling algorithm or the like. Note that, in the CG adjustment processing, generally, the mirror 119 is moved at any time to scan a plurality of positions of the eye to be examined and obtain a plurality of tomographic images. Therefore, a plurality of tomographic images may be used as one set of input data.

Note that, such a machine learning model may perform learning by reinforcement learning. In this case, for example, tomographic images can be labelled, and learning can be performed in a manner so that the reward given to a result that obtained an image with ideal labels with the least delay possible is greatest. Further, in this case also, a learned model obtained by learning using a model of an eye in advance may be subjected to transfer learning in which learning with the human eye is additionally performed.

Further, in the case of detecting an abnormal site, the first alignment unit 24 may use a GAN or a VAE. For example, a DCGAN composed of a generator that is obtained by learning to generate a tomographic image, and a discriminator that is obtained by learning to distinguish between a new tomographic image which the generator generated and a real tomographic image can be used as a machine learning model.

In the case of using a DCGAN, for example, the discriminator subjects an input tomographic image to encoding to convert the tomographic image into a latent variable, and the generator generates a new tomographic image based on the latent variable. Thereafter, a difference between the input tomographic image and the new tomographic image that was generated can be extracted as an abnormal site. Further, in the case of using a VAE, for example, an input tomographic image is converted into a latent variable by encoding the tomographic image using an encoder, and a new tomographic image is generated by decoding the latent variable using a decoder. Thereafter, a difference between the input tomographic image and the new tomographic image that was generated can be extracted as an abnormal site.

Note that, in a case where a plurality of abnormal sites are detected or the like, which of the detected plurality of regions to perform CG adjustment based on may be selected in accordance with an instruction of the operator. Further, in a case where an abnormal site was detected, for example, with regard to the region of the abnormal site that was detected, an ROI indicating the relevant region may be displayed in a superimposed manner on the tomographic image.

In the case of detecting a predetermined region using such kind of learned model, it can be expected that the predetermined region will be quickly and accurately detected from a tomographic image.

Furthermore, with regard to the CG adjustment processing, the first alignment unit 24 may determine the movement amount of the mirror 119 from the tomographic image by using a learned model. The machine learning model in this case may be a CNN or the like. As the training data in this case, an anterior ocular segment image can be adopted as the input data, and a movement amount (vector) to the position of the mirror 119 at a time that an image of the aforementioned predetermined region of the anterior ocular segment image is located at a predetermined depth position in the tomographic image can be adopted as the ground truth. Note that, with regard to the ground truth of the training data, it may be a movement amount during CG adjustment that is performed according to an operation of a medical professional with respect to a tomographic image, or a movement amount during CG adjustment performed based on a known algorithm with respect to a tomographic image, or a movement amount obtained when a medical professional modified the aforementioned movement amount, or the like.

Note that, this kind of machine learning model may also perform learning by reinforcement learning. In this case, for example, tomographic images are obtained while shifting the mirror 119 disposed at a random position by a random amount in a random direction among the driving directions of the mirror 119, and evaluation of the tomographic images is performed. Then, a difference between the evaluation values is calculated, and using the difference as a reward, learning of the neural network is performed by the error back propagation method so that the maximum reward is obtained. Note that, the aim of the reinforcement learning may be set as, for example, arriving at the position at which the reward is maximized in the shortest time. Further, in this case also, a learned model obtained by learning using a model of an eye in advance may be subjected to transfer learning in which learning with the human eye is additionally performed.

If this kind of learned model is used, a movement amount for moving the mirror 119 to an appropriate CG position can be quickly determined from a tomographic image. Note that, in Embodiment 1 and the present modification, when performing the CG adjustment processing, the CG position is adjusted by moving the mirror 119. However, a method for adjusting the CG position is not limited thereto. The CG position can be changed by adjusting (changing) the optical path length difference between the measurement optical path and the reference optical path. Therefore, the CG adjustment processing may be performed using a mechanism that changes the optical path length of the reference optical path or a mechanism that changes the optical path length of the measuring light, which are mechanisms other than the mirror 119. In this case, it suffices that the output data of the learned model used for the CG adjustment processing is the amount of change (information pertaining to a position at which to dispose the CG) in an optical path length that is caused by the mechanism used for the CG adjustment processing.

Note that, although a configuration in which the first alignment unit 24 performs detection of a predetermined region is adopted in the present modification and in Embodiment 1, a detecting unit for detecting a predetermined region may be provided separately to the first alignment unit 24. Such a detecting unit may be constituted by a software module executed by a processor such as a CPU, an MPU, a GPU, or an FPGA, or by a circuit that serves a specific function such as an ASIC, or the like.

Note that, with regard to moving images of an anterior ocular segment image, a fundus front image, and a tomographic image which are displayed in a preview image, in the case of performing the first alignment processing, focus adjustment processing, and CG adjustment processing, each processing mentioned above may be performed for each frame of the moving image. Further, these processings may be performed at every predetermined number of frames of the moving image. Therefore, with respect to processing for detecting a predetermined region using the various learned models mentioned above also, similarly the processing may be performed for each frame of a moving image, or may be performed at every predetermined number of frames.

Further, with regard to detection for an abnormal site in various kinds of images, for example, the detection processing may be performed with respect to various kinds of images such as a fundus front image or a tomographic image obtained by actual imaging. The detection method in this case may be a rule-based method as mentioned in Embodiment 1, or may be a method that uses a learned model. In this case, the display controlling unit 28 may display a detected abnormal site in a superimposed manner on various kinds of images. By this means, the examiner can be prompted to make a decision regarding whether to perform imaging again, and thus the diagnosis by the examiner can be assisted. Note that, when displaying a detected abnormal site in a superimposed manner on various kinds of images, the display controlling unit 28 may cause a message prompting the examiner to perform additional imaging corresponding to the abnormal site to be displayed on the display unit 40. For example, in a case where an abnormal site was detected in the vascular zone, the display controlling unit 28 can cause a message that prompts the examiner to additionally perform OCTA imaging or fluorescence imaging to be displayed on the display unit 40.

Note that, the first alignment processing according to the present modification is also not limited to a configuration in which the first alignment is performed by movement of the optical head unit 100, and the first alignment may be performed by at least one of drive control of the optical head unit 100 and drive control of the face receiving unit 160. In this case also, it suffices that the training data of the learned model used for the first alignment processing is training data corresponding to the drive control that is used for the first alignment processing. Further, the focus adjustment processing according to the present modification is also not limited to a configuration in which the focus adjustment is performed using a focusing lens, and the focus adjustment may be performed using a focusing optical system such as a Badal optical system.

Modification 4

In Embodiment 1, after the first alignment unit 24 performs the first alignment processing, focus adjustment processing, and CG adjustment processing, the second alignment unit 25 performs the second alignment processing using a learned model. On the other hand, the second alignment unit 25 may perform the second alignment processing, focus adjustment processing, and CG adjustment processing using a learned model. In Modification 4, a configuration is described in which the second alignment unit 25 performs the second alignment processing, focus adjustment processing, and CG adjustment processing using a learned model.

In this case, a machine learning model that is used may be, for example, a CNN or a model in which a CNN and an LSTM are combined. Further, with regard to the training data, an anterior ocular segment image, a fundus front image, and a tomographic image are adopted as input data, and movement amounts of the optical head unit 100, the lenses 107 and 115, and the mirror 119 are adopted as a ground truth. More specifically, the ground truth of the training data includes movement amounts in the XYZ directions when the optical head unit 100 was aligned with respect to the eye to be examined E so as to avoid opacity in the eye to be examined E, movement amounts of the lenses 107 and 115 so that the contrast is maximized in the aforementioned predetermined region in a fundus front image, and a movement amount to the position of the mirror 119 when an image of the aforementioned predetermined region in an anterior ocular segment image is located at a predetermined depth position in a tomographic image. Note that, these movement amounts may be represented by vectors.

Note that, this kind of machine learning model may perform learning by reinforcement learning. In this case, for example, tomographic images are obtained while shifting the optical head unit 100, the lens 107, and the mirror 119 which are disposed at a random position by a random amount in a random direction, respectively, and evaluation of the tomographic images is performed. Then, a difference between the evaluation values is calculated, and using the difference as a reward, learning of the neural network is performed by the error back propagation method so that the maximum reward is obtained. Note that, the aim of the reinforcement learning may be set as, for example, arriving at the position at which the reward is maximized in the shortest time. Further, in this case also, a learned model obtained by learning using a model of an eye in advance may be subjected to transfer learning in which learning with the human eye is additionally performed.

By using this kind of learned model, the second alignment unit 25 according to the present modification can perform the second alignment processing, focus adjustment processing and CG adjustment processing in parallel with each other from an anterior ocular segment image, a fundus front image, and a tomographic image. Consequently, the preparatory processing up to the actual imaging can be performed more quickly, and because the examination time is shortened, the burden on the subject can be reduced.

Note that, in the foregoing, it is described that movement amounts in the XYZ directions when the optical head unit 100 was aligned with respect to the eye to be examined E so as to avoid opacity of the eye to be examined E are included as the ground truth of the training data. In addition thereto, the ground truth of the training data may include movement amounts in the XYZ directions when the optical head unit 100 was aligned with respect to the eye to be examined E so as to correspond to decentration of the pupil of the eye to be examined. Further, similarly, movement amounts in the XYZ directions when the optical axis of the optical head unit 100 was aligned with the centroid of a pupil with respect to a healthy eye may be included as the ground truth of the training data. Thus, by using a learned model that performed learning using the relevant training data, appropriate alignment processing can also be performed with respect to an eye in which pupil decentration has occurred and a healthy eye.

Further, it is considered that, by the learned model which the second alignment unit 25 using being equipped with, for example, three input channels for inputting an anterior ocular segment image, a fundus front image, and a tomographic image, respectively, and extracting feature values from the images input from the respective input channels, and performing processing in a manner that takes into consideration the mutual relationship between the respective feature values, respective movement amounts that are appropriate can be output. With regard to machine learning models, for example, it is known that a machine learning model which adopts a color image as input data is equipped with an input channel for each of R (red), G (green), and B (blue), and performs processing in a manner that takes into consideration the mutual relationship between the respective feature values of images that were input from the respective input channels. Therefore, it is considered that the learned model according to the present modification can also perform processing that is similar to such processing.

Note that, in the present modification, an anterior ocular segment image, a fundus front image, and a tomographic image are used as input data of the machine learning model. On the other hand, two kinds of images among an anterior ocular segment image or a fundus front image and a tomographic image, or only a tomographic image may be used as the input data of the machine learning model. Even in this case, if the learned model is used, it can be expected that appropriate second alignment processing, focus adjustment processing, and CG adjustment processing can be performed according to the training data or the contents of reinforcement learning.

Note that, the second alignment processing that includes focus adjustment processing and CG adjustment processing (hereinafter, referred to as "integrated alignment processing") which uses a learned model according to the present modification, may be executed without performing the first alignment processing. In this case, the ophthalmic apparatus need not be equipped with the first alignment unit 24. Further, the integrated alignment processing according to the present modification may adopt a moving image as input data, similarly to Embodiment 1. With regard to moving images of an anterior ocular segment image, a fundus front image, and a tomographic image that are displayed on a preview screen, in the case of performing the integrated alignment processing, the processing may be performed for each frame of the moving image, or may be performed at every predetermined number of frames of the moving image.

As described above, the ophthalmic apparatus according to the present modification is equipped with the optical head unit 100 that includes an optical system for irradiating the eye to be examined E with light and detecting return light from the eye to be examined, and the second alignment unit 25 (information obtaining unit). The second alignment unit 25 uses a learned model obtained by learning information showing the position of the optical head unit 100 with respect to the eye to be examined E to obtain information pertaining to a position at which to dispose the optical head unit 100 with respect to the eye to be examined E from a tomographic image obtained using the optical head unit 100. Further, the learned model which the second alignment unit 25 uses is a machine learning model obtained by learning positional information of the optical head unit 100 in a case where the optical axis of the light flux from the optical head unit 100 was shifted from the centroid of the pupil of the eye to be examined E.

Further, the ophthalmic apparatus according to the present modification is an optical tomographic imaging apparatus in which the second alignment unit 25 uses a learned model obtained by learning information showing a position of the optical head unit 100 with respect to the eye to be examined E, information showing a position of the lens 107, and information showing a position of the mirror 119 to obtain information pertaining to positions at which to dispose the optical head unit 100, the lenses 107 and 115 and the mirror 119 with respect to the eye to be examined E from a tomographic image obtained using the optical head unit 100. In addition, by using the learned model, the second alignment unit 25 can obtain information pertaining to positions at which to dispose the optical head unit 100, the lenses 107 and 115 and the mirror 119 with respect to the eye to be examined E, based on at least one of a tomographic image, a fundus front image and an anterior ocular segment image obtained using the optical head unit 100.

In addition, the ophthalmic apparatus according to the present modification is further equipped with the drive controlling unit 22 that controls driving of the optical head unit 100. Based on information pertaining to a position at which to dispose the optical head unit 100 that the second alignment unit 25 obtained, the drive controlling unit 22 controls driving of the optical head unit 100 to the relevant position. Further, the drive controlling unit 22 functions as one example of an adjusting unit that adjusts the arrangement of the optical head unit 100, the lens 107, and the mirror 119. Therefore, the drive controlling unit 22 can adjust the arrangement of the optical head unit 100, the lens 107, and the mirror 119 based on information pertaining to positions at which to dispose the optical head unit 100, the lens 107, and the mirror 119 that the second alignment unit 25 obtained.

In the ophthalmic apparatus according to the present modification, the second alignment unit 25 can use the learned model to perform second alignment processing, focus adjustment processing, and CG adjustment processing in parallel from an anterior ocular segment image, a fundus front image, and a tomographic image. Consequently, the preparatory processing up to the actual imaging can be performed more quickly, and because the examination time is shortened, the burden on the subject can be reduced. Further, since the second alignment unit 25 can perform similar second alignment processing to the second alignment processing in Embodiment 1, the ophthalmic apparatus according to the present modification can obtain the same effects as the effects stated in Embodiment 1.

Note that, as described above, the CG adjustment processing may be performed using a mechanism that changes the optical path length of the reference optical path or a mechanism that changes the optical path length of the measuring light which is a mechanism other than the mirror 119. In this case, it suffices that the output data of the learned model relating to the CG adjustment processing is the amount of change (information pertaining to the position at which to dispose the CG) in an optical path length that is caused by the mechanism used for the CG adjustment processing.

Further, in the case of performing the integrated alignment processing with respect to a moving image, the processing may be ended in accordance with an instruction from the operator or the processing may be ended automatically. In the case of automatically ending the integrated alignment with respect to a moving image, for example, the processing may be ended when the Q index value of a tomographic image obtained at an alignment position (including a focusing position and a CG position also) that was adjusted by the integrated alignment processing is equal to or greater than a threshold. Further, for example, the processing may be ended by, from among a plurality of alignment positions based on images of a predetermined number of frames, taking an alignment position for which the Q index value of a tomographic image obtained at that position is highest as the final alignment position. In addition, in the case of automatically ending the integrated alignment with respect to a moving image, the display controlling unit 28 may display information indicating the end of the integrated alignment processing on the display unit 40, and display a message prompting the operator to execute actual imaging on the display unit 40. Note that, in the case of automatically ending the processing, the Q index value of a tomographic image with respect to an alignment position that is determined at the time point at which the processing ends may be compared with a Q index value for a tomographic image with respect to a first alignment position in a similar manner to step S611.

Further, in the case of performing the integrated alignment processing with respect to a moving image, if the Q index value of a tomographic image obtained at respective alignment positions does not increase within a predetermined time period, the processing may be ended even if the Q index value is less than the threshold. Note that, in this case, on the display unit 40, the display controlling unit 28 may display information to the effect that although the Q index value is less than the threshold, the processing has been ended because a predetermined time period has elapsed.

Note that, the second alignment processing according to the present modification is also not limited to a configuration in which the second alignment is performed by movement of the optical head unit 100, and the second alignment may be performed by at least one of drive control of the optical head unit 100 and drive control of the face receiving unit 160. In this case also, it suffices that the training data of the learned model used for the second alignment processing is training data corresponding to the drive control that is used for the second alignment processing. Further, the focus adjustment processing according to the present modification is also not limited to a configuration in which the focus adjustment is performed using a focusing lens, and the focus adjustment may be performed using a focusing optical system such as a Badal optical system.

Modification 5

In Embodiment 1, an anterior ocular segment image is adopted as the input data for the training data of the learned model which the second alignment unit 25 uses. On the other hand, an image relating to the fundus Ef, for example, a fundus front image, a tomographic image, an en-face image or an OCTA front image may be adopted as the input data. Therefore, in Modification 5, a case where an image relating to the fundus Ef is adopted as the input data for the training data of the learned model which the second alignment unit 25 uses is described.

As described above, in a case where there is an opaque portion in the eye to be examined E, a light flux for fundus observation or for fundus measurement is scattered by the opaque portion, and an image obtained using the light flux is darkened. Therefore, alignment that avoids an opaque portion can also be performed by moving the optical head unit 100 based on the position of a place (dark portion) that is darkened in an obtained image relating to the fundus Ef. For example, in a case where, in a fundus front image, there is a place which is darkened in comparison to other places in a portion on the right side, an opaque portion can be avoided by moving the optical head unit 100 to the left side of the eye to be examined E.

Hereunder, a learned model which the second alignment unit 25 uses in the present modification will be described. For example, a CNN or a model in which a CNN and an LSTM are combined or the like can be used as the machine learning model according to the present modification.

Here, the aforementioned image relating to the fundus Ef is used as input data for the training data of the learned model that the second alignment unit 25 uses in the present modification. Note that, an image relating to the fundus Ef that serves as the input data is not limited to an image obtained at a position after the first alignment processing, and images obtained at various alignment positions are used. With respect to the ground truth, a movement amount in at least one direction among the XYZ directions when the operator aligned the optical head unit 100 with respect to the eye to be examined E so as to avoid opacity in the eye to be examined E when the image relating to the fundus Ef used as the input data was obtained may be adopted as the ground truth. Note that, the ground truth may be movement amounts in the XYZ directions when the operator aligned the optical head unit with respect to the eye to be examined E so as to avoid opacity in the eye to be examined E based on an anterior ocular segment image or a transillumination image obtained together with the image relating to the fundus Ef that is used as the input data.

Note that, the ground truth of the training data may include movement amounts in the XYZ directions when the optical head unit 100 was aligned with respect to the eye to be examined E so as to correspond to decentration of the pupil of the eye to be examined E. Further, similarly, movement amounts in the XYZ directions when the optical axis of the optical head unit 100 was aligned with the centroid of a pupil with respect to a healthy eye may be included as the ground truth of the training data. Thus, by using a learned model that performed learning using the relevant training data, appropriate alignment processing can also be performed with respect to an eye in which pupil decentration has occurred and a healthy eye.

Further, with regard to the learned model that the second alignment unit 25 uses, in the case of performing reinforcement learning, an image adopted as input data is not limited to an image obtained at a position after the first alignment processing, and images obtained at various alignment positions are used. Further, when performing learning, from the respective positions among various alignment positions, imaging of a tomographic image is performed while shifting the optical head unit 100 that was disposed at a random position by a random amount in a random direction among the XYZ directions, and evaluation of the tomographic image is performed. Note that, an evaluation index such as the aforementioned Q index may be used for evaluation of the tomographic image. Thereafter, the optical head unit 100 is randomly moved once again, a tomographic image is obtained, and evaluation of the tomographic image is performed. Then, a difference between the evaluation values is calculated, and using the difference as a reward, learning of the neural network is performed by the error back propagation method so that the maximum reward is obtained. Note that, a Q-learning algorithm, SARSA, a Monte Carlo method, a bandit algorithm or the like may also be used as the algorithm for reinforcement learning. Note that, the aim of the reinforcement learning may be set as, for example, arriving at the position at which the reward is maximized in the shortest time.

Note that, it is considered that a learned model which performed such learning extracts a range and shape of a dark portion included in an image relating to the fundus Ef, and learns a feature value that represents the correlation between the range and shape of the dark portion and the position of the optical head unit 100. However, it is considered that the information amount of the information relating to the range and shape of a dark portion included in an image relating to the fundus Ef is less than the information amount of the information relating to the shape of an opaque part included in an anterior ocular segment image or a transillumination image. Therefore, it is also considered that moving the alignment position one time is not sufficient to enable the optical head unit 100 to move to an appropriate alignment position for avoiding opacity. Consequently, in the present modification, in the second alignment processing, inference of an alignment position using a learned model and movement are repeated until the optical head unit 100 can move to an appropriate alignment position.

Figure 16:
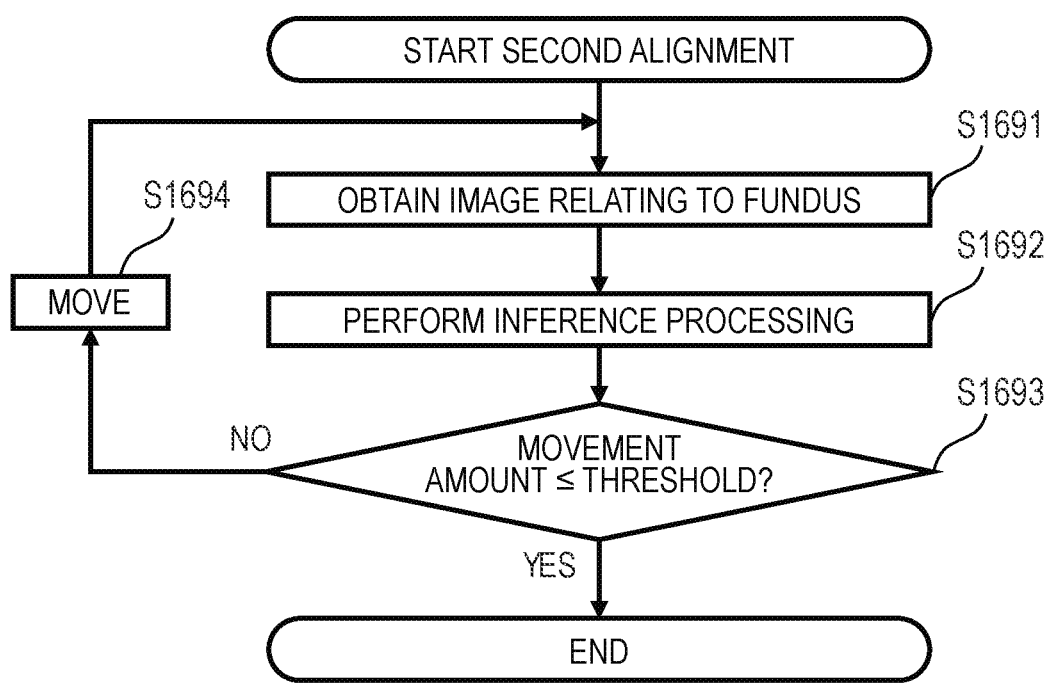
FIG. 16 is a flowchart illustrating second alignment processing according to Modification 5.

FIG. 16 is a flowchart illustrating the second alignment processing according to the present modification. In the present modification, the second alignment processing illustrated in FIG. 16 is executed in step S609 in the series of processing illustrated in FIG. 6A. Note that, hereunder, an example in which a fundus front image is used as an image relating to the fundus Ef is described. However, as described above, the image relating to the fundus Ef may be, for example, a tomographic image, an en-face image, or an OCTA front image.

Upon the second alignment processing being executed, in step S1691, the obtaining unit 21 obtains an output signal from the CCD 105, and the image generating unit 23 generates a fundus front image based on the output signal. In step S1692, the second alignment unit 25 uses the aforementioned learned model to determine information pertaining to a position at which the optical head unit 100 should be disposed with respect to the eye to be examined E (second alignment position) from the fundus front image. Specifically, the second alignment unit 25 inputs the fundus front image to the learned model, and determines the second alignment position based on the output (inference result)

from the learned model. Note that, in the present modification, as the information pertaining to the second alignment position, the second alignment unit 25 determines movement amounts in the XYZ directions of the optical head unit 100 to the second alignment position.

In step S1693, the second alignment unit 25 determines whether or not the determined movement amount is greater than a threshold. In the present modification, the initial threshold is set to a predetermined value. Further, in a case where the relevant determination processing is being performed for a second or subsequent time, the threshold is set to half of the movement amount that was determined the previous time. Note that, the threshold may be arbitrarily set according to the desired configuration.

In step S1693, if the second alignment unit 25 determines that the determined movement amount is greater than the threshold, the processing transitions to step S1694. In step S1694, the drive controlling unit 22 controls the stage unit 150 to move the optical head unit 100 based on the determined movement amount. Upon the optical head unit 100 moving to the position determined in step S1692, the processing transitions to step S1691.

On the other hand, in step S1693, if the second alignment unit 25 determines that the determined movement amount is equal to or less than the threshold, the second alignment unit 25 ends the second alignment processing, and the processing transitions to step S610.

In the second alignment processing according to the present modification, an image relating to the fundus Ef is adopted as the input, and inference of an alignment position using a learned model and movement are repeated until the optical head unit 100 can be moved to an appropriate alignment position. With this processing also, since autoalignment can be continuously performed to a position that avoids an opaque part or a position corresponding to decentration of the pupil of the eye to be examined E, imaging can be performed while maintaining a favorable state for an image that is obtained, even in the case of tomography for which the imaging time is comparatively long. Therefore, the complexity of an operation for adjusting an alignment position can be reduced with respect to, in particular, a diseased eye in which the corneal shape is abnormal or a diseased eye affected by a cataract or the like.

Note that, the second alignment processing according to the present modification can also be applied to a moving image on the aforementioned preview screen and the like.

In the reinforcement learning of the machine learning model according to the present modification, apart from the learning described above, learning may be used which determines a movement amount of the optical head unit 100 so that a reward given to a state (result) which obtained an ideal image relating to the fundus Ef with the least delay possible is greatest. Here, an ideal image relating to the fundus Ef may be an image for which an evaluation value, for example, a Q index value, a signal-to-noise ratio, or a contrast value or the like with respect to the image relating to the fundus Ef is equal to or greater than the threshold or the like.

Further, in the present modification, it has been described that an image relating to the fundus Ef is used as input data. On the other hand, an anterior ocular segment image or a transillumination image and an image relating to the fundus Ef that were obtained at approximately the same timing may be used as the input data. In addition, a plurality of kinds of images relating to the fundus Ef that were obtained at approximately the same timing may be used as the input data. In these cases, it suffices to adopt similar images as the input data of the training data also. Note that, with regard to the ground truth of the training data, a movement amount in at least one direction among the XYZ directions when the operator aligned the optical head unit with respect to the eye to be examined E so as to avoid opacity in the eye to be examined E when these images were obtained may be adopted as the ground truth. In these cases, it is considered that a greater amount of information relating to the shape of an opaque part can be extracted from an image, and therefore it is considered that the optical head unit can be moved to an appropriate alignment position with a smaller number of repetitions, that is, in a shorter time.

In addition, in the present modification, the second alignment unit 25 uses a movement amount to make a determination as to whether or not to repeat the second alignment processing. On the other hand, the evaluating unit 26 may make the determination using an evaluation value for an image relating to the fundus Ef obtained at the second alignment position which was determined. Note that, as the evaluation value in this case, for example, a Q index value, a signal-to-noise ratio, or a contrast value or the like may be used according to the kind of image relating to the fundus Ef.

Note that, the second alignment processing using a learned model according to the present modification may be executed without performing the first alignment processing. In this case, the ophthalmic apparatus need not be equipped with the first alignment unit 24. Further, although in the present modification, an image relating to the fundus is used as input data of the training data, an image of the anterior ocular segment may be used.

Modification 6

Information pertaining to the second alignment position that is obtained using a learned model by the second alignment unit 25 according to the embodiment and modifications described above may be manually modified according to an instruction from the operator. For example, after the optical head unit 100 was moved to the second alignment position, the operator can give an instruction to perform additional movement of the optical head unit 100. At such time, the instruction (movement amount and movement direction) from the operator may be stored in the storage 27 as additional information with respect to the information pertaining to the second alignment position that was determined using the learned model.

Here, the information pertaining to the second alignment position that was manually modified may be used for incremental learning for the learned model that the second alignment unit 25 uses. In this case, with respect to the learned model that the second alignment unit 25 uses, incremental learning can be performed in which an anterior ocular segment image or the like that was input is adopted as input data of the training data, and information pertaining to a second alignment position according to an instruction from the operator is adopted as a ground truth (correct answer data).

By performing this kind of incremental learning with respect to the learned model, it can be expected that the accuracy of the second alignment processing using the learned model will be improved, and that second alignment processing which is in accordance with the tendency of operations performed by the examiner can be performed. Further, by performing such processing, labeling processing (annotation processing) relating to training data can be easily performed, and higher accuracy training data can be easily created.

Note that, the aforementioned incremental learning may be performed according to an instruction of the operator. For example, in a case where a modification has been made according to an instruction of the operator with respect to information pertaining to the second alignment position, the display controlling unit 28 can cause a display for selecting whether or not to use the modified information pertaining to the second alignment position as training data to be displayed on the display unit 40. By selecting one of the choices displayed on the display unit 40, the operator can give an instruction as to whether or not incremental learning is necessary. By this means, the controlling unit 20 can determine whether or not incremental learning is necessary in accordance with the instruction given by the operator.

Note that, as described later, a learned model can also be provided in an apparatus such as a server. In such a case, the controlling unit 20 can, according to an instruction by an operator to perform incremental learning, transmit and store an input image and information of the second alignment position on which the aforementioned modification was performed as a pair of training data to the relevant server or the like. In other words, the controlling unit 20 can determine whether to transmit training data for incremental learning to an apparatus such as a server which is equipped with a learned model, according to an instruction of the operator.

Note that, with respect to the various learned models described in the modifications 2-5, the respective learned models may also similarly perform incremental learning using data that was manually modified according to an instruction of the operator as training data. Further, a determination as to whether or not incremental learning is necessary and a determination as to whether or not to transmit data to a server may also be performed by similar methods. In these cases also, it can be expected that the accuracy of each kind of processing will be enhanced, and processing in accordance with the tendency of the preference of the examiner can be performed.

Modification 7

Individual differences exist with respect to alignment positions that are desired by operators as alignment positions with respect to an eye to be examined. Therefore, learning that tunes a learned model according to a particular operator may be performed.

For example, past alignment operations by the operator with respect to eyes to be examined can be used to perform transfer learning to a general purpose learned model for alignment, and in this way a learned model for alignment that is for dedicated use by the relevant operator can be generated. In this case, for example, a learned model for dedicated use by a given operator that is linked to an operator ID which is information indicating the relevant operator can be stored in the controlling unit 20 or a server or the like, and the learned model for dedicated use by the relevant operator which is in accordance with the operator ID can be used for the current examination. By this means, the convenience of the apparatus for each operator can be enhanced.

Modification 8

In the case of a diseased eye, the image features will differ according to the kind of disease. Therefore, various learned models used in the embodiments and modifications described above may be generated and prepared for each kind of disease or each abnormal site. In this case, for example, the controlling unit 20 can select a learned model to be used for processing, according to an input (instruction) indicating the kind disease, the abnormal site of the eye to be examined or the like from the operator. With regard to the learned models for each kind of disease or each abnormal site, if the learned models are for the second alignment processing, for example, a model for cataracts, a model for pupil decentration, a model for miosis, a model for healthy eyes and the like may be prepared. These learned models, for example, may be learned models that performed learning using training data for each of a cataractous eye, an eye in which pupil decentration has occurred, an eye in which miosis has occurred, and a healthy eye. Note that, learned models that are prepared for each kind of disease or each abnormal site are not limited to learned models for the second alignment processing. The learned models that are prepared for each kind of disease or each abnormal site may be learned models for detecting a predetermined region in various kinds of images, or learned models for focus adjustment processing, for CG adjustment processing, or for integrated alignment processing or the like.

Further, the controlling unit 20 may identify the kind of disease or an abnormal site of an eye to be examined from an image using a separately prepared learned model. In this case, the controlling unit 20 can automatically select a learned model to be used in the aforementioned processing based on the kind of disease or the abnormal site that was identified using the separately prepared learned model. Note that, a learned model for identifying the kind of disease or an abnormal site of the eye to be examined can perform learning using pairs of training data for which an anterior ocular segment image, a fundus front image, a tomographic image or the like is adopted as input data, and kinds of diseases or abnormal sites in these images are adopted as ground truth. In this case, with respect to the input data of the training data, an anterior ocular segment image, a fundus front image, a tomographic image or the like may be independently adopted as input data, or a combination of these images may be adopted as input data.

In addition, in an ophthalmic apparatus, for example, in an OCT apparatus, a scan pattern of a light flux used for measurement or an imaging site differs for each imaging mode. Therefore, with regard to a learned model that adopts a tomographic image as input data, a configuration may be adopted in which a learned model is prepared for each imaging mode, and a learned model is selected that corresponds to an imaging mode which was selected according to an instruction of the operator. In this case, for example, a retina imaging mode, an anterior ocular segment imaging mode, a vitreous body imaging mode, a macular area imaging mode, and an optic nerve head imaging mode or the like may be included as the imaging modes. Further, a 3D scan, a radial scan, a cross scan, a circle scan, a raster scan, a Lissajous scan (scanning along a Lissajous curve) or the like may be included as scan patterns. Furthermore, with regard to a learned model that adopts a tomographic image as input data, the learned model can perform learning that uses tomographic images corresponding to cross sections in different directions as training data. For example, learning that uses tomographic images of cross sections in the XZ directions and tomographic images of cross sections in the YZ directions for training data may be performed.

Modification 9

In the focus adjustment processing (step S605) or CG adjustment processing (step S606) according to Embodiment 1, in a case where a predetermined region is specified by an instruction by the operator, and respective regions are detected by rule-based processing, the first alignment unit 24 can ascertain the name of each region. Therefore, in this case, the display controlling unit 28 can display the name of each region on the display unit 40 together with a fundus front image or a tomographic image displayed in the preview screen.

Further, in a case where an abnormal site is specified as a predetermined region, the controlling unit 20 may determine a name or a diagnosis name indicating the abnormal site based on rule-based processing, and the display controlling unit 28 may display the name or the diagnosis name indicating the abnormal site on the display unit 40. Note that, the controlling unit 20 may determine a name or a diagnosis name indicating an abnormal site using a learned model that performed learning in which an image in which an abnormal site appears or a label image showing region names, and names or diagnosis names indicating abnormal sites are used as training data. Note that, names or diagnosis names indicating an abnormal site may be displayed in order of highest probability, for example, around three names or diagnosis names, on the display unit 40. Note that, the number of names or diagnosis names indicating an abnormal site that are displayed is not limited to three, and any number may be displayed.

Further, the controlling unit 20 may cause a name of a region specified as a predetermined region, or a name or diagnosis name indicating an abnormal site to be stored in the storage 27 in association with image data obtained by actual imaging. Further, the controlling unit 20 may transmit these to an external server or record them in electronic clinical records.

Note that, a name or diagnosis name of an abnormal site may be manually modified by the operator. In this case, the controlling unit 20 may cause the learned model used for the relevant determination to perform incremental learning in which the image used for the determination and the modified name or diagnosis name are used as training data. Note that, whether or not to perform the incremental learning may be determined according to an instruction by the operator.

Further, when performing a follow-up observation (follow-up), the controlling unit 20 may perform detection for the aforementioned predetermined region with respect to past data that is stored. In this case also, similarly, the display controlling unit 28 may cause the name of each region or a name or diagnosis name of an abnormal site to be displayed on the display unit 40 together with an image that is displayed. In particular, in a case where data from a preview time is stored, a name of each region or a name or diagnosis name of an abnormal site may be displayed on the display unit 40 together with an image that is displayed on the relevant preview screen. Further, specification of a predetermined region in this case may also be performed according to an instruction of the operator.

Note that, as mentioned in Modification 3, in the focus adjustment processing (step S605) or the CG adjustment processing (step S606), similar processing may also be performed in the case of detecting for a predetermined region using a learned model. In this case, the learned model that detects a predetermined region may be, for example, a learned model that outputs a label image in which region names have been labeled for each pixel of an input image.

Modification 10

The ophthalmic apparatus is not limited to an OCT apparatus, and may be, for example, a fundus camera, a scanning laser ophthalmoscope (SLO) apparatus, an OCTA apparatus, or a refractometer (eye refractive power measuring apparatus). Further, in the embodiment described above, a spectral domain OCT (SD-OCT) apparatus is described as the OCT apparatus. However, other Fourier domain OCT (FD-OCT) apparatuses including a swept source OCT (SS-OCT) apparatus, or a time domain OCT (TD-OCT) apparatus may be included as examples of the OCT apparatus. Further, a Line-OCT apparatus (or an SS-Line-OCT apparatus) that uses line light may be included as an example of the OCT apparatus. Furthermore, a Full Field-OCT apparatus (or an SS-Full Field-OCT apparatus) that uses area light may be included as an example of the OCT apparatus. Further, a Doppler-OCT apparatus may be included as an example of the OCT apparatus. In addition, an adaptive optics SLO (AO-SLO) apparatus and an adaptive optics OCT (AO-OCT) apparatus that use an adaptive optics system and the like may be included as examples of an SLO apparatus or an OCT apparatus, respectively. Furthermore, a polarization-sensitive SLO (PS-SLO) apparatus and a polarization-sensitive OCT (PS-OCT) apparatus and the like for visualizing information relating to polarization phase differences or depolarization may be included as examples of an SLO apparatus or an OCT apparatus, respectively. In addition, a pathology microscope SLO apparatus and a pathology microscope OCT apparatus and the like may be included as examples of an SLO apparatus and an OCT apparatus, respectively. Further, a hand-held type SLO apparatus and a hand-held type OCT apparatus and the like may be included as examples of an SLO apparatus and an OCT apparatus, respectively. In addition, a catheter SLO apparatus and a catheter OCT apparatus and the like may be included as examples of an SLO apparatus and an OCT apparatus, respectively.

Note that, in a case where the ophthalmic apparatus is a fundus camera, an SLO apparatus, or a refractometer or the like, it is not necessary to adjust a coherence gate. Therefore, in this case, the processing in step S606 may be omitted from the series of processing illustrated in FIG. 6A.

Further, in Embodiment 1, since the OCT apparatus 1 was described, with respect to the evaluation of the image quality, it was described that the image quality of a tomographic image was evaluated. On the other hand, in the series of processing illustrated in FIG. 6A, an image relating to the fundus Ef evaluated after each alignment may be an image that is the object of imaging according to the type of ophthalmic apparatus. For example, in the case of an SLO apparatus or a fundus camera, evaluation of a fundus front image may be performed, and in the case of an OCTA apparatus, evaluation of an OCTA tomographic image or an OCTA front image may be performed. Further, in the case of an OCT apparatus, for example, evaluation of an intensity en-face image may also be performed. In addition, the evaluation performed during reinforcement learning is also not limited to a tomographic image, and evaluation of an image that is the object of the imaging may be performed.

Note that, in Embodiment 1, focus adjustment processing was performed based on a fundus front image that was imaged using the OCT apparatus 1. On the other hand, in a case where the ophthalmic apparatus is an SLO apparatus or a case where the ophthalmic apparatus includes an SLO optical system, focus adjustment may be performed so that the received light amount at a light receiving unit of the SLO optical system is maximized. Further, in a case where the ophthalmic apparatus is a fundus camera, in some cases, the ophthalmic apparatus includes a split lens for focus adjustment. In this case, focus adjustment may be performed so that split index images that are imaged using the split lens correspond (are aligned).

In addition, in an apparatus that uses an adaptive optics system (AO-OCT apparatus or AO-SLO apparatus), in general, adaptive optics processing is performed using a sensor such as a Shack-Hartmann wavefront sensor as an aberration measuring unit, and using a deformable mirror as an aberration correcting unit. With respect to such a configuration, estimation of a control amount of the aberration correcting unit may be performed using a machine learning model. In this case, for example, a Shack-Hartmann image is adopted as the input data of the training data, and a control amount of the aberration correcting unit is adopted as the ground truth. In such a case, since a correction amount of a wavefront aberration can be estimated using a learned model, calculation of a wavefront aberration can be simplified, and drive control can be performed quickly. Note that, the data that is input may be a moving image or may be a still image.

For example, a CNN or a model in which a CNN and an LSTM are combined or the like can be used as a machine learning model that is used for the adaptive optics processing. It is considered that in such a learned model a feature value relating to distortion of a wavefront is extracted for an image of each frame and is used for estimation processing.

Modification 11

The controlling unit 20 may perform various image processing using an image obtained by actual imaging. For example, with respect to an image obtained by actual imaging, the controlling unit 20 may generate a high quality image in which the image quality was improved using a learned model for improving image quality (image quality improving model). Here, the improvement of the image quality includes a reduction of noise, conversion of an imaging target to a color and gradation that are easy to observe, an improvement in the resolution or spatial resolution, and enlargement of the image size with suppressed deterioration of the resolution.

For example, a CNN or the like can be used as a machine learning model for improving image quality. Further, as the training data of an image quality improving model, various kinds of images such as an anterior ocular segment image and a fundus front image are adopted as input data and, for example, a high quality image that was subjected to image quality improving processing which corresponds to the image that was input is adopted as ground truth. Here, as an example of the image quality improving processing, processing in which alignment is performed with respect to images obtained by imaging the same spatial position a plurality of times, and the aligned images are then subjected to arithmetic averaging processing may be mentioned. Note that, the image quality improving processing is not limited to arithmetic averaging processing, and for example may be processing using a smoothing filter, maximum a posteriori processing (MAP estimation processing), or gradation conversion processing. Further, as an image that was subjected to image quality improving processing, for example, an image on which filter processing such as noise removal and edge enhancement was performed may be used, or an image for which the contrast was adjusted so as to obtain a high-intensity image from a low-intensity image may be used. In addition, with regard to a ground truth of training data pertaining to the image quality improving model, since it suffices that the ground truth is a high quality image, the ground truth may be a tomographic image that was imaged using an OCT apparatus with higher performance than the OCT apparatus used to image the image that is the input data, or may be an image that was imaged with high load settings.

However, if machine learning is performed using an image on which image quality improving processing has not been suitably performed as ground truth of the training data, there is a probability that an image obtained using a learned model that learned using the relevant training data will also be an image on which image quality improving processing has not been suitably performed. Therefore, by removing pairs which include such images from the training data, the probability that an image which is not suitable will be generated using the learned model can be reduced.

By performing image quality improving processing using this kind of image quality improving model, the controlling unit 20 can more quickly obtain an image that was subjected to image quality improving with favorable accuracy.

Note that, an image quality improving model may be prepared for each of various kinds of images that are the input data. For example, an image quality improving model for anterior ocular segment images, an image quality improving model for fundus front images, an image quality improving model for tomographic images, and an image quality improving model for OCTA front images may be prepared. Further, with respect to OCTA front images or en-face images, an image quality improving model may be prepared for each depth range for generating an image. For example, an image quality improving model for a surface layer and an image quality improving model for a deep layer may be prepared. In addition, image quality improving models may be learned models that performed learning with respect to images for each imaging site (for example, the center of the macular area and the center of the optic nerve head). At this time, for example, a fundus OCTA front image may be subjected to image quality improving using an image quality improving model obtained by learning using a fundus OCTA front image as training data, and an anterior ocular segment OCTA front image may be subjected to image quality improving using an image quality improving model obtained by learning using an anterior ocular segment OCTA front image as training data. Further, the image quality improving model may be a learned model that performed learning regardless of an imaging site. Here, for example, the appearance of the distribution of blood vessels which are an imaging target is sometimes comparatively similar in a fundus OCTA front image and an anterior ocular segment OCTA front image. In a plurality of kinds of medical images in which the appearance of an imaging target is comparatively similar to each other in this way, the feature values of the respective images are sometimes comparatively similar to each other. Therefore, for example, a configuration may be adopted in which an image quality improving model obtained by learning using a fundus OCTA front image as training data can be used not only to subject a fundus OCTA front image to image quality improving, but also to subject an anterior ocular segment OCTA front image to image quality improving. Further, for example, a configuration may be adopted in which an image quality improving model obtained by learning using an anterior ocular segment OCTA front image as training data can be used not only to subject an anterior ocular segment OCTA front image to image quality improving, but also to subject a fundus OCTA front image to image quality improving. That is, a configuration may be adopted in which an image quality improving model obtained by learning using at least one kind of front image among a fundus OCTA front image and an anterior ocular segment OCTA front image can be used to subject at least one kind of front image among a fundus OCTA front image and an anterior ocular segment OCTA front image to image quality improving. Thus, for example, in a case where it is considered that the feature values (appearance of the imaging target) of a plurality of kinds of medical images are comparatively similar to each other, a configuration may be adopted in which image quality improving of at least one kind of medical image among the plurality of kinds of medical images can be performed using an image quality improving model obtained by learning using at least one kind of medical image among the plurality of kinds of medical images as training data. Therefore, for example, a configuration can be adopted in which image quality improving of a plurality of kinds of medical images can be executed using a common learned model (common image quality improving model).

Here, for example, a plurality of OCTA front images (OCTA en-face images, motion-contrast en-face images) (corresponding to a plurality of depth ranges) may be target images of the image quality improving processing. Further, a target image of the image quality improving processing may be, for example, one OCTA front image corresponding to one depth range. Further, instead of an OCTA front image, a target image of the image quality improving processing may be, for example, an intensity front image (intensity en-face image), an OCT tomographic image that is a B-scan image, or a tomographic image of motion contrast data (OCTA tomographic image). In addition, a target image of the image quality improving processing is not limited to an OCTA front image, and various medical images may be a target image, for example, an intensity front image, an OCT tomographic image that is a B-scan image, and a tomographic image of motion contrast data (OCTA tomographic image). That is, it suffices that the target image of the image quality improving processing is, for example, at least one of various medical images displayed on a display screen of the display unit 40. At such time, for example, since there are cases where the feature values of the images differ for each kind of image, learned models for improving image quality which correspond to the respective kinds of target images of the image quality improving processing may be used. For example, a configuration may be adopted so that when an image quality improving button is pressed according to an instruction from the examiner, not only is an OCTA front image subjected to image quality improving processing using a learned model for improving image quality corresponding to OCTA front images, but an OCT tomographic image is also subjected to image quality improving processing using a learned model for improving image quality corresponding to OCT tomographic images. Further, for example, a configuration may be adopted so that when an image quality improving button is pressed according to an instruction from the examiner, not only is the display changed to a display of a high quality OCTA front image generated using a learned model for improving image quality corresponding to OCTA front images, but the display is also changed to a display of a high quality OCT tomographic image generated using a learned model for improving image quality corresponding to OCT tomographic images. At such time, a configuration may be adopted so that a line indicating the position of the OCT tomographic image is displayed in a superimposed manner on the OCTA front image. Further, a configuration may be adopted so that the aforementioned line can be moved on the OCTA front image according to an instruction from the examiner. Further, a configuration may be adopted so that in a case where the display of the image quality improving button is in an active state, after the aforementioned line was moved, the display is changed to a display of a high quality OCT tomographic image obtained by subjecting an OCT tomographic image corresponding to the current position of the line to image quality improving processing. Further, a configuration may be adopted that, by displaying an image quality improving button for each target image of the image quality improving processing, enables image quality improving processing to be performed independently for each image.

Further, information indicating a vascular zone (for example, motion contrast data that is equal to or greater than a threshold) in an OCTA tomographic image may be displayed in a superimposed manner on an OCT tomographic image that is a B-scan image of the corresponding position. At such time, for example, when the OCT tomographic image is subjected to image quality improving, the OCTA tomographic image of the corresponding position may be subjected to image quality improving. Further, information indicating a vascular zone in an OCTA tomographic image obtained by performing image quality improving may be displayed in a superimposed manner on an OCT tomographic image obtained by performing image quality improving. Note that, the information indicating a vascular zone may be of any kind as long as the information enables a color or the like to be distinguished. Further, a configuration may be adopted so that the display can be changed between superimposed display and non-display of information indicating a vascular zone according to an instruction from the examiner. Further, when a line indicating the position of an OCT tomographic image is moved on an OCTA front image, the display of an OCT tomographic image may be updated according to the position of the line. At such time, since an OCTA tomographic image of the corresponding position is also updated, the superimposed display of information indicating a vascular zone obtained from the OCTA tomographic image may be updated. Therefore, for example, at an arbitrary position, the three-dimensional distribution or state of the vascular zone can be effectively confirmed while easily confirming the positional relation between the vascular zone and a region of interest. Further, instead of using a learned model for improving image quality, the image quality improving of an OCTA tomographic image may be image quality improving processing performed by arithmetic averaging processing or the like of a plurality of OCTA tomographic images obtained at corresponding positions. Further, the OCT tomographic image may be a pseudo-OCT tomographic image that was reconstructed as a cross section at an arbitrary position in OCT volume data. Further, the OCTA tomographic image may be a pseudo-OCTA tomographic image that was reconstructed as a cross section at an arbitrary position in OCTA volume data. Note that, it suffices that the arbitrary position is at least one arbitrary position, and a configuration may be adopted so that the arbitrary position can be changed according to an instruction from the examiner. At such time, a configuration may be adopted so that a plurality of pseudo-tomographic images corresponding to a plurality of positions are reconstructed.

Note that, the number of displayed tomographic images (for example, OCT tomographic images or OCTA tomographic images) may be one tomographic image or may be a plurality of tomographic images. In a case where a plurality of tomographic images are displayed, tomographic images obtained at different positions to each other in the subscanning direction may be displayed, and for example in a case where a plurality of tomographic images obtained by cross-scanning or the like are subjected to image quality improving and displayed, the respective images in the different scanning directions may be displayed. Further, for example, in a case where a plurality of tomographic images obtained by radial scanning or the like are subjected to image quality improving and displayed, some selected (plurality of) tomographic images (for example, two tomographic images at positions symmetrical to each other with respect to a reference line) may each be displayed. In addition, a plurality of tomographic images may be displayed on a display screen for follow-up observation, and an instruction for image quality improvement or an analysis result (for example, the thickness of a specific layer) may be displayed by a similar method as the method described above. Further, image quality improving processing may be executed on a tomographic image based on information stored in a database by the same method as the method described above.

Similarly, in the case of subjecting an SLO fundus image to image quality improving and displaying the resultant image, for example, an SLO fundus image displayed on the same display screen may be subjected to image quality improving and displayed. In addition, in the case of subjecting an intensity front image to image quality improving and displaying the resultant image, for example, an intensity front image displayed on the same display screen may be subjected to image quality improving and displayed. In addition, a plurality of SLO fundus images or intensity front images may be displayed on a display screen for follow-up observation, and an instruction for image quality improvement or an analysis result (for example, the thickness of a specific layer) may be displayed by a similar method as the method described above. Further, image quality improving processing may be executed on an SLO fundus image or an intensity front image based on information stored in a database by the same method as the method described above. Note that, the displays of the tomographic images, SLO fundus images, and intensity front images are for illustrative purposes, and these images may be displayed in any form according to a desired configuration. Further, at least two or more of OCTA front images, tomographic images, SLO fundus images and intensity front images may be subjected to image quality improving and displayed based on a single instruction.

According to such a configuration, the display controlling unit 28 can cause a high quality image obtained by performing image quality improving processing to be displayed on the display unit 40. Note that, a configuration may be adopted so that in a case where at least one condition is selected among a plurality of conditions relating to the display of high quality images, the display of analysis results, and the depth range of a front image to be displayed and the like, even if the display screen is transitioned to another display screen, the selected condition(s) is maintained. Note that, control of the display of various high quality images, the aforementioned line, or information indicating a vascular zone or the like may be performed by the display controlling unit 28.

Further, an image quality improving model may be used for even at least one frame of a live moving image on a preview screen displayed on the display unit 40 by the display controlling unit 28. At such time, a configuration may be adopted so that, in a case where a plurality of live moving images of different sites or different kinds are displayed on the preview screen, learned models that correspond to the respective live moving images are used. For example, with regard to an anterior ocular segment image that is used for the second alignment processing by the second alignment unit 25, an image that was subjected to image quality improving by an image quality improving model for anterior ocular segment images may be used. Similarly, with regard to various kinds of images that are used for processing for detecting a predetermined region in various kinds of images by the first alignment unit 24, images that were subjected to image quality improving using image quality improving models for the respective images may be used.

At such time, for example, a configuration may be adopted so that, if the image quality improving button is pressed according to an instruction from the examiner, the display of a plurality of live moving images of different kinds (for example, an anterior ocular segment image, a fundus front image, and a tomographic image) is (simultaneously) changed to a display of high quality moving images obtained by performing image quality improving processing on each of the live moving images. At such time, the display of high quality moving images may be a consecutive display of high quality images obtained by subjecting each frame to image quality improving processing. Further, for example, since there are cases where the feature values of the images differ for each kind of image, learned models for improving image quality which correspond to the respective kinds of target images of the image quality improving processing may be used. For example, a configuration may be adopted so that when an image quality improving button is pressed according to an instruction from the examiner, not only is an anterior ocular segment image subjected to image quality improving processing using an image quality improving model corresponding to anterior ocular segment images, but a fundus front image is also subjected to image quality improving processing using an image quality improving model corresponding to fundus front images. Further, for example, a configuration may be adopted so that when the image quality improving button is pressed according to an instruction from the examiner, not only is the display changed to a display of a high quality anterior ocular segment image generated using an image quality improving model corresponding to anterior ocular segment images, but the display is also changed to a display of a high quality fundus front image generated using an image quality improving model corresponding to fundus front images. Further, for example, a configuration may be adopted so that when the image quality improving button is pressed according to an instruction from the examiner, not only is a fundus front image subjected to image quality improving processing using an image quality improving model corresponding to fundus front images, but a tomographic image is also subjected to image quality improving processing using an image quality improving model corresponding to tomographic images. Furthermore, for example, a configuration may be adopted so that when the image quality improving button is pressed according to an instruction from the examiner, not only is the display changed to a display of a high quality fundus front image generated using an image quality improving model corresponding to fundus front images, but the display is also changed to a display of a high quality tomographic image generated using an image quality improving model corresponding to tomographic images. At such time, a configuration may be adopted so that a line indicating the position of the tomographic image is displayed in a superimposed manner on the fundus front image. Furthermore, a configuration may be adopted so that the aforementioned line can be moved on the fundus front image according to an instruction from the examiner. Further, a configuration may be adopted so that in a case where the display of the image quality improving button is in an active state, after the aforementioned line was moved, the display is changed to a display of a high quality tomographic image obtained by subjecting a tomographic image corresponding to the current position of the line to image quality improving processing. Further, a configuration may be adopted that, by displaying an image quality improving button for each target image of the image quality improving processing, enables image quality improving processing to be performed independently for each image.

By this means, for example, since the processing time can be shortened even for a live moving image, the examiner can obtain highly accurate information prior to the start of imaging. Therefore, for example, in a case where the operator modifies an alignment position while checking the preview screen, failures of re-imaging and the like can be reduced, and consequently the accuracy and efficiency of diagnosis can be improved. Further, according to an instruction relating to the start of imaging, the controlling unit 20 may control driving of the aforementioned scanning unit so that, during imaging or at the end of imaging, a partial region such as an artifact region obtained by segmentation processing or the like is imaged again (rescanned). Further, for example, a configuration may be adopted so as to automatically perform respective adjustments or automatically start imaging or the like when information (for example, a numerical value indicating a percentage) that indicates the likelihood of an object recognition result relating to a site of interest exceeds a threshold. Further, for example, a configuration may be adopted so as to change (release an execution-prohibited state) to a state in which respective adjustments or the start of imaging or the like can be executed according to an instruction from the examiner, in a case where information (for example, a numerical value indicating a percentage) that indicates the likelihood of an object recognition result relating to a site of interest exceeds a threshold.

Here, there is a probability that, during auto-alignment, the imaging target such as the retina of the eye to be examined E could not yet be successfully imaged. Consequently, there is a probability that a high quality image will not be accurately obtained because there is a large difference between the medical image that is input to the learned model and the medical image that was used as training data. Therefore, a configuration may be adopted so that when an evaluation value such as a value obtained when the image quality of a tomographic image (B-scan image) is evaluated exceeds a threshold, display of a high quality moving image (consecutive display of high image quality frames) is automatically started. Further, a configuration may be adopted so that when an evaluation value such as a value obtained when the image quality of a tomographic image is evaluated exceeds a threshold, the image quality improving button is changed to a state (active state) in which the button can be selected by the examiner. Note that, the image quality improving button is a button for specifying execution of image quality improving processing. Naturally, the image quality improving button may be a button for inputting an instruction to display a high quality image.

Further, as mentioned in Modification 8, a configuration may be adopted in which a different image quality improving model is prepared for each imaging mode which each uses a different scanning pattern or the like, and a learned model for improving image quality that corresponds to a selected imaging mode is selected. Further, one image quality improving model obtained by learning using training data including various medical images obtained in different imaging modes may be used.

Note that, a determination as to whether or not it is necessary to execute image quality improving processing by an image quality improving model (or to display a high quality image obtained by performing image quality improving processing) may be made according to an instruction of the operator with respect to an image quality improving button that is provided on the display screen, or may be made according to a setting that is stored in advance in the storage 27. Note that, the fact that the image quality improving processing is performed using a learned model (image quality improving model) may be displayed in an active state of the image quality improving button or the like, or that fact may be displayed as a message on the display screen. Further, with regard to execution of the image quality improving processing, the execution state thereof the previous time that the ophthalmic apparatus was started may be maintained, or the execution state at the time of the previous examination may be maintained for each subject.

Further, a moving image to which various kinds of learned models such as an image quality improving model can be applied is not limited to a live moving image, and for example the moving image may be a moving image stored (saved) in the storage 27. At such time, for example, a moving image obtained by performing alignment with respect to even at least one frame of a tomographic moving image of the fundus stored (saved) in the storage 27 may be displayed on the display screen. For example, in a case where it is desired to suitably observe the vitreous body, first, a reference frame based on conditions such as that the vitreous body is present as much as possible in the frame may be selected. At such time, each frame is a tomographic image (B-scan image) in the XZ directions. Subsequently, a moving image in which other frames have been aligned in the XZ directions with respect to the selected reference frame may be displayed on the display screen. At such time, for example, a configuration may be adopted so as to cause high quality images (high image quality frames) sequentially generated by an image quality improving engine for even at least one frame of the moving image to be consecutively displayed.

Note that, as methods for performing alignment among frames that is described above, the same method may be applied with respect to the method for performing alignment in the X direction and the method for performing alignment in the Z direction (depth direction), or the methods that are applied may all be different. In addition, alignment in the same direction may be performed a plurality of times by different methods. For example, a rough alignment may be performed, and thereafter a fine alignment may be performed. Further, as a method for alignment, for example, a method is available that performs (rough Z-direction) alignment using a retinal layer boundary obtained by subjecting a tomographic image (B-scan image) to segmentation processing, a method is available that performs (fine X-direction or Z-direction) alignment using correlation information (similarity) between a plurality of regions obtained by dividing a tomographic image and a reference image, a method is available that performs (X-direction) alignment using a one-dimensional projection image generated for each tomographic image (B scan image), and a method is available that performs (X-direction) alignment using a two-dimensional front image and the like. Further, a configuration may be adopted so as to perform fine alignment in sub-pixel units after rough alignment was performed in pixel units.

Further, the image quality improving model may be updated by incremental learning in which the value of a ratio that was set (changed) according to an instruction from the examiner is adopted as training data. For example, if the examiner tends to set the ratio of the input image to the high quality image high when the input image is relatively dark, the learned model performs incremental learning so as to have such a tendency. Thus, for example, the learned model can be customized as a learned model that can obtain a combining ratio that matches the preference of the examiner. At such time, a button for determining, according to an instruction from the examiner, whether or not to use the set (changed) value of the ratio as training data for incremental learning may be displayed on the display screen. Further, a configuration may be adopted in which a ratio determined using the learned model is taken as a default value and, thereafter, the ratio value can be changed from the default value according to an instruction from the examiner. Further, the image quality improving model may be a learned model obtained by incremental learning using training data including at least one high quality image generated using an image quality improving model. At such time, a configuration may be adopted that enables a selection as to whether or not a high quality image is to be used as training data for incremental learning to be made by an instruction from the examiner.

Modification 12

In addition, the controlling unit 20 may, with respect to an image obtained by actual imaging, use a learned model for image segmentation to generate a label image and perform image segmentation processing. Here, the term "label image" refers to a label image in which a label of a region has been given to each pixel with respect to the tomographic image. Specifically, the term "label image" refers to an image in which arbitrary regions among a group of regions visualized in the obtained image are classified according to identifiable pixel value (hereunder, referred to as a "label value") groups. Here, a region of interest and a volume of interest (VOI) and the like are included in the arbitrary regions that are identified.

When identifying groups of coordinates of pixels having an arbitrary label value from an image, it is possible to identify a group of coordinates of pixels that visualize a corresponding region such as a retinal layer in the image. Specifically, for example, in a case where a label value that indicates the ganglion cell layer forming the retina is "1", a coordinate group for which the pixel value is "1" is identified among the pixel groups of the image, and a pixel group corresponding to the coordinate group is extracted from the image. By this means, the region of the ganglion cell layer in the image can be identified.

Note that, the image segmentation processing may include processing in which the label image is subjected to reduction or enlargement processing. At such time, the use of a nearest-neighbor method or the like that does not erroneously generate an undefined label value or a label value that should not exist at the corresponding coordinates may be adopted as an image interpolation processing method that is used for reducing or enlarging the label image.

The term "image segmentation processing" refers to processing that identifies a region called an ROI or a VOI such as an organ or a lesion that is visualized in an image, in order to utilize such regions for image diagnosis or image analysis. For example, according to the image segmentation processing, a group of regions of a layer group constituting the retina can be identified from an image obtained by OCT imaging for which the posterior ocular segment was taken as the imaging target. Note that, if regions to be identified are not visualized in the relevant image, the number of identified regions is 0. Further, if a group of a plurality of regions to be identified is visualized in the image, the number of identified regions may be a plural, or may be a single region that surrounds a group of regions so as to include the group of regions.

The identified group of regions is output as information that can be utilized in other processing. Specifically, for example, a group of coordinates of pixel groups that constitute the identified group of regions, respectively, can be output as a numerical value data group. Further, for example, a group of coordinates indicating a rectangular region, an elliptical region, a parallelepiped region, an ellipsoidal region or the like including each of the identified groups of regions can also be output as a numerical value data group. In addition, for example, a group of coordinates indicating a straight line, a curved line, a plane, a curved surface or the like that is the boundary of an identified group of regions can be output as a numerical value data group. Further, for example, a label image indicating an identified group of regions can also be output.

In this case, for example, a convolutional neural network (CNN) can be used as a machine learning model for image segmentation. Note that, for example, a CNN (U-Net type machine learning model) as illustrated in FIG. 10, a model obtained by combining a CNN and an LSTM, an FCN or a SegNet or the like can also be used as the machine learning model according to the present modification. In addition, a machine learning model that performs object recognition in region units which is described in the modification 3 or the like can be used according to a desired configuration. Further, for the training data of a machine learning model for image segmentation, a tomographic image obtained by an OCT is adopted as input data, and a label image obtained by giving a label of a region to each pixel with respect to the tomographic image is adopted as a ground truth. As the label image, for example, a label image in which labels such as inner limiting membrane (ILM), nerve fiber layer (NFL), ganglion cell layer (GCL), photoreceptor inner segment-outer segment junction (ISOS), retinal pigment epithelium (RPE), Bruch's membrane (BM) and choroid have been given to regions can be used. Note that, as other regions, for example, a label image in which labels such as vitreous body, sclera, outer plexiform layer (OPL), outer nuclear layer (ONL), inner plexiform layer (IPL), inner nuclear layer (INL), cornea, anterior chamber, iris, and crystalline lens have been given to regions may be used.

Further, the input data of the machine learning model for image segmentation is not limited to a tomographic image. The input data may be an anterior ocular segment image, a fundus front image, an OCTA image, or the like. In this case, for the training data, various kinds of images can be adopted as input data, and a label image in which region names or the like have been labeled for each pixel of the various kinds of images can be adopted as a ground truth. For example, in a case where the input data of the training data is a fundus front image, the ground truth may be an image in which labels have been given to regions such as a cup, a disc and a peripheral portion of the optic nerve head.

Note that, a label image that is used as the ground truth may be an image in which a label has been given to each region in a tomographic image by a physician or the like, or may be an image in which a label has been given to each region by rule-based region detection processing. However, if machine learning is performed using a label image for which labeling has not been appropriately performed as the ground truth of training data, there is a probability that an image obtained using a learned model that performed learning using the training data in question will also be a label image for which labeling has not been appropriately performed. Therefore, by excluding pairs including such kind of label images from the training data, the probability that an inappropriate label image will be generated using the learned model can be reduced. Here, the term "rule-based region detection processing" refers to detection processing that utilizes, for example, known regularity such as the regularity of the shape of the retina.

By performing image segmentation processing using such a kind of learned model for image segmentation, it can be expected that the controlling unit 20 will quickly and accurately detect specific regions with respect to various kinds of images. Note that, the learned model for image segmentation may be used as the learned model for detecting a predetermined region which is mentioned in Modification 3.

Note that, a learned model for image segmentation also may be prepared for each kind of image among various kinds of images that are input data. Further, with regard to an OCTA front image or an en-face image, a learned model may be prepared for each depth range for generating an image. In addition, the learned model for image segmentation also may be a learned model that has performed learning with respect to images of each imaged site (for example, the center of the macular area and the center of the optic nerve head), or may be a learned model that has performed learning irrespective of the imaged sites.

Further, with regard to the learned model for image segmentation also, similarly to the processing described in Modification 6, incremental learning may be performed in which data that was manually modified according to an instruction of the operator is used as training data. Further, a determination as to whether or not incremental learning is necessary and a determination as to whether or not to transmit data to a server can be performed by the same methods as the methods described above. In these cases also, it can be expected that the accuracy of each processing will be enhanced, and processing according to the tendency of the preference of the examiner can be performed.

In addition, in a case where the controlling unit 20 detects for partial regions (for example, a site of interest, an artifact region, or an abnormal site) of the eye to be examined E using a learned model, predetermined image processing can also be performed for each detected region. As an example, let us consider a case of detecting at least two partial regions among a vitreous body region, a retina region and a choroid region. In this case, when performing image processing such as contrast adjustment with respect to the at least two partial regions that were detected, adjustment that is suited to the respective regions can be performed by using different image processing parameters for the respective regions. By displaying an image on which adjustment suited to the respective regions was performed, the operator can more appropriately diagnose a disease or the like in each partial region. Note that, with regard to a configuration that uses image processing parameters that differ for each partial region that was detected, such a configuration may also be similarly applied with respect to partial regions of the eye to be examined E that were determined by detecting partial regions of the eye to be examined E without using a learned model.

Modification 13

Further, the display controlling unit 28 may cause analysis results such as the thickness of a desired layer or various blood vessel densities to be displayed on the report screen of the display screen of an image obtained by actual imaging. Further, a parameter value (distribution) relating to a site of interest including at least one of the optic nerve head, the macular area, a vascular zone, a capillary zone, an artery zone, a vein zone, a nerve fascicle, a vitreous region, a macular region, a choroid region, a sclera region, a lamina cribrosa region, a retinal layer boundary, a retinal layer boundary edge, a photoreceptor cell, a blood cell, a blood vessel wall, a blood vessel inner wall boundary, a blood vessel external boundary, a ganglion cell, a corneal region, a corner region, and Schlemm's canal and the like may be displayed as an analysis result. At such time, for example, an accurate analysis result can be displayed by analyzing a medical image subjected to various kinds of artifact removal processing. Note that, an artifact may be, for example, a false image region caused by light absorption by a vascular zone or the like, a projection artifact, or a band-like artifact in a front image that arises in the main scanning direction of the measuring light due to the state of the eye to be examined (movement or blinking or the like). Further, an artifact may be of any kind as long as the artifact is an imaging failure region that, for example, randomly arises at each imaging on a medical image of a predetermined site of the subject. Further, the display controlling unit 28 may cause the value (distribution) of a parameter relating to a region including at least one of the various kinds of artifacts (imaging failure regions) described above to be displayed as an analysis result on the display unit 40. Furthermore, the value (distribution) of a parameter relating to a region including at least one abnormal site such as drusen, a neovascular site, leucoma (hard exudates), pseudodrusen or the like may be displayed as an analysis result. Further, a comparison result obtained by comparing a standard value or standard range obtained using a standard database and an analysis result may be displayed.

An analysis result may be displayed using an analysis map, or using sectors which indicate statistical values corresponding to respective divided regions or the like. Note that, an analysis result may be generated using a learned model (analysis result generating engine, or a learned model for generating analysis results) obtained by learning the analysis results of various kinds of images as training data. At such time, the learned model may be a model obtained by learning using training data including a medical image and an analysis result for the medical image, or training data including a medical image and an analysis result for a medical image of a different kind from the relevant medical image or the like.

Further, the training data of a learned model for performing image analysis may include a label image generated using a learned model for image segmentation processing and a result of analyzing a medical image using the label image. In this case, the controlling unit 20, for example, can function as one example of an analysis result generating unit that generates an analysis result with respect to a tomographic image from a result of the image segmentation processing using a learned model for generating analysis results. In addition, a learned model may be a model obtained by learning using training data including input data in which a plurality of medical images of different kinds of a predetermined site, such as an en-face image and an OCTA front image, are taken as a set.

Further, a configuration may be adopted so as to display an analysis result obtained using a high quality image generated using an image quality improving model. In this case, input data included in the training data may be a high quality image generated using a learned model for improving image quality, or may be a set composed of a low quality image and a high quality image. Note that, the training data may be an image obtained by manually or automatically modifying at least one part of an image that was subjected to image quality improving using a learned model.

Further, the training data may be, for example, data obtained by labeling (annotation) input data for which information including at least one kind of information among an analysis value (for example, an average value or a median value) obtained by analyzing an analysis region, a table including analysis values, an analysis map, and a position of an analysis region such as a sector in an image or the like, is adopted as correct answer data (of supervised learning). Note that, a configuration may be adopted so that an analysis result obtained using a learned model for generating analysis results is displayed according to an instruction from the examiner.

The display controlling unit 28 in the embodiments and modifications described above may cause various kinds of diagnosis results such as results relating to diabetic retinopathy, glaucoma or age-related macular degeneration to be displayed on the report screen of the display screen of an image obtained by actual imaging. At such time, for example, an accurate diagnosis result can be displayed by analyzing a medical image subjected to various kinds of artifact removal processing as described above. Further, as the diagnosis result, the position of a specified abnormal site may be displayed on the image, and the state of an abnormal site or the like may be displayed using characters or the like. Further, a classification result (for example, Curtin's classification) for an abnormal site may be displayed as a diagnosis result. Further, as a classification result, for example, information (for example, a numerical value indicating a percentage) that indicates the degree of likelihood for each abnormal site may be displayed. In addition, information that is required so that the physician can confirm the diagnosis may be displayed as a diagnosis result. For example, advice such as to perform additional imaging is conceivable as the aforementioned required information. For example, in a case where an abnormal site is detected in a vascular zone in an OCTA image, information on the effect of advising the physician to additionally perform fluorescence imaging using a contrast medium that enables more detailed observation of blood vessels than by OCTA may be displayed. Further, a diagnosis result may be information relating to the future medical examination and treatment policy regarding the subject or the like. Furthermore, a diagnosis result may be information including at least one of, for example, the diagnosis, a kind or state (extent) of a lesion (abnormal site), the position of a lesion in the image, the position of a lesion relative to a region of interest, the findings (interpretation findings or the like), grounds for the diagnosis (affirmative medical support information or the like), and grounds for negating the diagnosis (negative medical support information). At this time, for example, a diagnosis result for which the likelihood is greater than a diagnosis result such as a diagnosis that was input according to an instruction from the examiner may be displayed as medical support information. Further, in a case where a plurality of kinds of medical images were used, for example, the kind of medical image that can be grounds for the diagnosis result may be distinguishably displayed. In addition, grounds for the diagnosis result may be a map in which a feature value that the learned model extracted is visualized, for example, a color map (heat map) in which a feature value is shown in color. At such time, for example, the heat map may be displayed in a superimposed manner on the medical image used as the input data.

Note that, a diagnosis result may be a result generated using a learned model (diagnosis result generating engine, or a learned model for diagnosis result generation) obtained by learning using diagnosis results for medical images as training data. Further, the learned model may be a model obtained by learning using training data including a medical image and a diagnosis result for the medical image, or training data including a medical image and a diagnosis result for a medical image of a different kind from the relevant medical image or the like.

Furthermore, the training data may include a label image generated using a learned model for image segmentation processing and a result of diagnosing a medical image using the label image. In this case, the controlling unit 20, for example, can function as one example of a diagnosis result generating unit that generates a diagnosis result with respect to a tomographic image from a result of an image segmentation processing using a learned model for diagnosis result generation.

In addition, a configuration may be adopted so as to display a diagnosis result obtained using a high quality image generated using a learned model for improving image quality. In this case, input data included in the training data may be a high quality image generated using a learned model for improving image quality, or may be a set composed of a low quality image and a high quality image. Note that, the training data may be an image obtained by manually or automatically modifying at least one part of an image that was subjected to image quality improving using a learned model.

Further, the training data may be, for example, data obtained by labeling (annotation) input data for which information including at least one kind of information among the diagnosis, a kind or state (extent) of a lesion (abnormal site), the position of a lesion in the image, the position of a lesion relative to a region of interest, the findings (interpretation findings or the like), grounds for the diagnosis (affirmative medical support information or the like), and grounds for negating the diagnosis (negative medical support information) and the like is adopted as correct answer data (of supervised learning). Note that, the display controlling unit 28 may be configured to cause the display unit 40 to display a diagnosis result obtained using a learned model for diagnosis result generation, according to an instruction from the examiner.

Further, for example, when it is desired to obtain a diagnosis result for glaucoma, a medical image including the optic nerve head (tomographic image, color fundus front image, intensity front image, OCTA front image or the like) or an analysis map (a thickness map obtained from OCT data, a vascular density map obtained from OCTA data or the like) may be used as the input data. At such time, one kind of information among these kinds of information may be used as the input data, or a plurality of kinds of information may be used as the input data. Further, for example, in a case where the input data of a plurality of kinds of information is an intensity front image and an OCTA front image, these front images may be front images of a common depth range obtained using OCT data in which at least one part is common, or may be front images of different depth ranges to each other. Further, for example, when it is desired to obtain a diagnosis result with respect to glaucoma, a tomographic image or OCTA tomographic image obtained by a circle scan around the optic nerve head may be used as input data. Further, for example, when it is desired to obtain a diagnosis result for glaucoma, a plurality of tomographic images or a plurality of OCTA tomographic image obtained by cross-scanning the optic nerve head may be used as input data. Further, for example, a diagnosis result for glaucoma may be the type or state (degree) of glaucoma. At such time, for example, the diagnosis result for glaucoma may be preperimetric glaucoma (PPG), first stage, intermediate stage, or later stage of glaucoma or the like. Further, the diagnosis result for glaucoma may be that although there is a low suspicion of a visual field abnormality such as a visual field defect, the state is one in which there is a high suspicion of a morphological change (abnormality) related to the retina such as enlargement of the optic nerve head cup or an optic nerve fiber defect is high, or the state is one in which there is a low suspicion of glaucoma or the like.

Note that, a learned model may be prepared for each piece of information or each kind of information to be used as input data, and a diagnosis result may be obtained using the learned models. In this case, the information output from each learned model may be subjected to statistical processing to determine the final diagnostic result. For example, the proportions of information output from the respective learned models may be added for each kind of information, and the information having a higher total proportion than the other information may be determined as the final diagnosis result. Note that, the statistical processing is not limited to the calculation of totals, and may be the calculation of an average value or a median value or the like. Further, for example, among the information output from each learned model, the diagnosis result may be determined by using information having a higher proportion (information having the highest proportion) than other information. Similarly, among the information output from each learned model, the diagnosis result may be determined by using information having a proportion that is equal to or greater than the threshold.

Further, a configuration may be adopted that enables a decision (acknowledgement) with respect to the quality of the determined diagnosis result according to an instruction (selection) of the operator. Further, the diagnosis result may be determined from information output from each learned model, according to an instruction (selection) of the operator. At such time, for example, the display controlling unit 28 may display the information output from each learned model and the proportion thereof side by side on the display unit 40. Further, a configuration may be adopted so that when the operator, for example, selects information that has a higher proportion than other information, the selected information is determined as the diagnosis result. In addition, a machine learning model may be used to determine the diagnosis result from information output from each learned model. In this case, the machine learning algorithm may be a machine learning algorithm of a different kind to the machine learning algorithm used to generate the diagnosis result, and for example Support Vector Machine, AdaBoost, a Bayesian network, or Random Forest may be used.

Note that, the learning of the various learned models mentioned above may not only be supervised learning (learning with labeled training data), but may also be semi-supervised learning. Semi-supervised learning is a method in which, for example, after a plurality of discriminators (classifiers) have each performed supervised learning, the discriminators identify (classify) unlabeled training data, automatically label (annotate) the unlabeled training data depending on the reliability of the identification result (classification result) (for example, an identification result for which the likelihood is equal to or greater than a threshold), and perform learning using the labeled training data. The semi-supervised learning may be, for example, co-training (or multiview training). At such time, a learned model for diagnosis result generation may be, for example, a learned model obtained by semi-supervised learning (for example, co-training) using a first discriminator that identifies a medical image of a normal subject, and a second discriminator that identifies a medical image including a specific lesion. Note that, use of semi-supervised learning is not limited to the purpose of diagnosis, and for example the purpose may be to assist imaging or the like. In this case, the second discriminator may be a discriminator that, for example, identifies a medical image including a partial region such as a site of interest or an artifact region.

Further, the display controlling unit 28 according to the various embodiments and modifications described above may cause an object recognition result (object detection result) or a segmentation result with respect to a site of interest, an artifact, an abnormal site or the like as described above to be displayed on the report screen of the display screen. At such time, for example, a rectangular frame or the like may be superimposed around an object on the image and displayed. Further, for example, a color or the like may be superimposed on an object in the image and displayed. Note that, an object recognition result or a segmentation result may be a result generated using a learned model (object recognition engine, learned model for object recognition, segmentation engine, or learned model for segmentation) obtained by learning using training data in which information that indicates object recognition or segmentation is labeled (annotated) on a medical image as correct answer data. Note that, the aforementioned analysis result generation or diagnosis result generation may be realized by utilizing the aforementioned object recognition result or segmentation result. For example, processing for generating an analysis result or for generating a diagnosis result may be performed with respect to a site of interest obtained by object recognition processing or segmentation processing.

Further, in the case of detecting an abnormal site, the controlling unit 20 may use a GAN or a VAE. For example, a DCGAN that is composed of a generator that is obtained by learning to generate a medical image, and a discriminator that is obtained by learning to distinguish between a new medical image which the generator generated and a real medical image of the ocular fundus can be used as a machine learning model.

In the case of using a DCGAN, for example, the discriminator subjects an input medical image to encoding to convert the medical image into a latent variable, and the generator generates a new medical image based on the latent variable. Thereafter, a difference between the input medical image and the new medical image that was generated can be extracted (detected) as an abnormal site. Further, in the case of using a VAE, for example, an input medical image is converted into a latent variable by encoding the medical image using an encoder, and a new medical image is generated by decoding the latent variable using a decoder. Thereafter, a difference between the input medical image and the new medical image that was generated can be extracted as an abnormal site.

In addition, the controlling unit 20 may detect an abnormal site using a convolutional auto-encoder (CAE). In the case of using a CAE, the same medical image is learned as input data and a ground truth during learning. Thus, when a medical image in which there is an abnormal site is input to the CAE during estimation, a medical image is output in which there is no abnormal site according to the learning tendency. Thereafter, a difference between the medical image input to the CAE and the medical image output from the CAE can be extracted as an abnormal site.

In these cases, the controlling unit 20 can generate, as information relating to an abnormal site, information relating to a difference between a medical image obtained using a generative adversarial network or an auto-encoder (AE), and a medical image input to the generative adversarial network or auto-encoder. Thus, it can be expected that the controlling unit 20 will quickly and accurately detect an abnormal site. For example, even in a case where it is difficult to collect a large number of medical images including abnormal sites as training data in order to improve the accuracy of detecting abnormal sites, medical images of normal subjects that are relatively easy to collect in a large number can be used as training data. Therefore, for example, learning for accurately detecting abnormal sites can be efficiently performed. Here, examples of the auto-encoder include a VAE and a CAE and the like. Further, at least one part of a generating unit of the generative adversarial network may be composed of a VAE. By this means, for example, a relatively clear image can be generated while reducing the phenomenon of generating similar data. For example, the controlling unit 20 can generate, as information relating to an abnormal site, information relating to a difference between a medical image obtained using a generative adversarial network or an auto-encoder from various medical images, and a medical image input to the generative adversarial network or the auto-encoder. Further, for example, the display controlling unit 28 can cause information relating to a difference between a medical image obtained using a generative adversarial network or an auto-encoder from various medical images, and a medical image input to the generative adversarial network or the auto-encoder to be displayed as information relating to an abnormal site on the display unit 40.

Furthermore, a learned model for diagnosis result generation may be a learned model obtained by learning using training data including input data in which a plurality of medical images of different kinds that are images of a predetermined site of a subject are taken as a set. At such time, for example, data in which an OCTA front image and an en-face image (or tomographic image) of the fundus are taken as a set is conceivable as input data included in the training data. Further, for example, input data in which a tomographic image (B-scan image) of the fundus and a color fundus front image (or fluorescence fundus front image) are taken as a set is conceivable as input data included in the training data. In addition, the plurality of medical images of different kinds may be of any kind as long as the medical images were obtained by different modalities, different optical systems, or different principles or the like.

Further, a learned model for diagnosis result generation may be a learned model obtained by learning using training data including input data in which a plurality of medical images of different sites of a subject are taken as a set. At such time, for example, input data in which a tomographic image (B-scan image) of the fundus and a tomographic image (B-scan image) of the anterior ocular segment are taken as a set is conceivable as input data included in the training data. Further, for example, input data in which a three-dimensional OCT image (three-dimensional tomographic image) of the macula of the fundus and a tomographic image obtained by circular scanning (or raster scanning) of the optic nerve head of the fundus are taken as a set is also conceivable as input data included in the training data.

Note that, the input data included in the training data of a learned model for a diagnosis result generation may be a plurality of medical images of different sites of the subject and of different kinds. At such time, for example, input data in which a tomographic image of the anterior ocular segment and a color fundus front image are taken as a set is conceivable as input data included in the training data. Further, the learned model for a diagnosis result generation may be a learned model obtained by learning using training data including input data in which a plurality of medical images of different imaging angles of view that are images of a predetermined site of the subject are taken as a set. Further, input data included in the training data may be data obtained by joining together a plurality of medical images obtained by time-dividing a predetermined site into multiple regions, such as in the case of a panorama image. At such time, by using a wide-angle image such as a panorama image as training data, the result of processing can be enhanced since there is a probability that a feature value of the image can be obtained with good accuracy for reasons such as the fact that the amount of information is greater than in the case of a narrow-angle image. Further, input data included in the training data may be input data in which a plurality of medical images obtained at different dates and times of a predetermined site of the subject are taken as a set.

Further, a display screen on which at least one result among an analysis result, a diagnosis result, an object recognition result and a segmentation result described above is to be displayed is not limited to the report screen. Such a display screen may be, for example, at least one display screen, which is caused to be displayed on the display unit 40 by the display controlling unit 28, among an imaging confirmation screen, a display screen for follow-up observation, and a preview screen for performing various kinds of adjustments before imaging (a display screen on which various kinds of live moving images are displayed) and the like. For example, by causing the aforementioned at least one result obtained using a learned model described above to be displayed on the imaging confirmation screen, the examiner can check an accurate result even immediately after imaging. Further, for example, a configuration may be adopted so that, when a specific object is recognized, a frame that surrounds the recognized object is displayed in a superimposed manner on a live moving image. At such time, in a case where information (for example, a numerical value indicating a percentage) that indicates the likelihood of the object recognition result exceeds a threshold, for example, the recognized object may be displayed with emphasis such as by the color of the frame surrounding the object being changed. By this means, the examiner can easily distinguish the object on the live moving image. Further, changing the display between a low quality image and a high quality image as described in Modification 11 and the like may be, for example, changing the display between an analysis result for a low quality image and an analysis result for a high quality image.

Note that, a learned model for generating correct answer data which generates correct answer data such as labeling (annotation) may be used to generate correct answer data used for learning by the various kinds of learned models described above. At such time, the learned model for generating correct answer data may be a learned model obtained by performing (sequential) incremental learning of correct answer data obtained when the examiner performed labeling (annotation). In other words, the learned model for generating correct answer data may be a learned model obtained by performing incremental learning of training data in which data before labeling is adopted as input data, and data after labeling is adopted as a ground truth. Further, in the case of a plurality of consecutive frames such as a moving image, a configuration may also be adopted so as to modify a result with respect to a frame for which it is determined that the accuracy of the result is low taking into account the results of object recognition or segmentation of the preceding and following frames. At such time, a configuration may be adopted so as to perform incremental learning of the modified result as correct answer data in accordance with an instruction from the examiner. Further, with regard to a medical image for which the accuracy of the result is low, a configuration may be adopted so as to perform incremental learning in which an image obtained by the examiner labeling (annotating) the relevant medical image while checking a map (heat map) in which feature values that the learned model extracted are visualized is used as input data. For example, in a heat map on a layer immediately before outputting the result in the learned model or the like, if a place to which attention should be paid is different from the intention of the examiner, a medical image in which places which the examiner thinks attention should be paid to were labeled (annotated) may be used for incremental learning. By this means, for example, the learned model can incrementally learn a feature value of a partial region on a medical image which is a partial region that has a relatively large influence on the output result of the learned model, with priority (by weighting) over the other regions.

Here, the various learned models mentioned above such as a learned model for analysis result generation and a learned model for diagnosis result generation can be obtained by machine learning that uses training data. For example, deep learning which is composed of a multi-level neural network is one kind of machine learning. Further, for example, a CNN can be used for at least a part of a multi-level neural network. In addition, technology pertaining to auto-encoders may be used for at least a part of a multi-level neural network. Furthermore, technology pertaining to back-propagation (error back-propagation method) may be used for learning. Further, a technique (dropout) that randomly deactivates respective units (respective neurons or respective nodes) may be used for learning. Further, a technique (batch normalization) that normalizes the data transmitted to each layer of the multi-layer neural network before an activation function (for example, a ReLu function) is applied may be used for learning. However, the machine learning is not limited to deep learning, and any learning may be employed as long as the learning uses a model that is capable of, by itself, extracting (representing) a feature value of training data such as an image by learning. Here, the term "machine learning model" refers to a learning model according to a machine learning algorithm such as deep learning. Further, the term "learned model" refers to a model which, with respect to a machine learning model according to any machine learning algorithm, trained (performed learning) using appropriate training data in advance. However, it is assumed that the learned model is not a model that does not perform further learning, and is a model that can also perform incremental learning. Further, the term "training data" refers to data composed of pairs of input data and a ground truth (correct answer data). Here, training data is also referred to as "teaching data" in some cases, and there are also cases where correct answer data is referred to as "teaching data".

Note that, a GPU can perform efficient arithmetic operations by performing parallel processing of larger amounts of data. Therefore, in a case where learning is performed a plurality of times using a learning model such as deep learning, it is effective to perform processing with a GPU. Thus, in the present modification, a GPU is used in addition to a CPU for processing by the controlling unit 20 that is an example of a learning unit (not illustrated). Specifically, when a learning program including the learning model is executed, learning is performed by the CPU and the GPU cooperating to perform arithmetic operations. Note that, with respect to the processing of the learning unit, arithmetic operations may be performed by only the CPU or the GPU. Further, a processing unit (estimating unit) that executes processing using the various learned models described above may also using a GPU, similarly to the learning unit. The learning unit may also include an error detecting unit and an updating unit (not illustrated). The error detecting unit obtains an error between output data that is output from the output layer of the neural network according to input data that is input to the input layer, and correct answer data. The error detecting unit may be configured to calculate an error between the output data from the neural network and the correct answer data using a loss function. Further, based on an error obtained by the error detecting unit, the updating unit updates combining weighting factors between nodes of the neural network or the like so that the error becomes small. The updating unit updates the combining weighting factors or the like using, for example, the error back-propagation method. The error back-propagation method is a method that adjusts combining weighting factors between the nodes of each neural network or the like so that the aforementioned error becomes small.

Further, a U-Net type machine learning model that has a function of an encoder that is composed of a plurality of levels including a plurality of downsampling layers, and a function of a decoder that is composed of a plurality of levels including a plurality of upsampling layers can be applied as a machine learning model to be used for image quality improving or segmentation or the like. In a U-Net type machine learning model, positional information (spatial information) that has been made ambiguous in a plurality of levels configured as an encoder is configured (for example, using a skip connection) so that the information can be used in levels of the same dimension (levels corresponding to each other) in a plurality of levels configured as a decoder.

In addition, for example, an FCN or a SegNet or the like can also be used as a machine learning model to be used for image quality improving or segmentation or the like. Further, a machine learning model that performs object recognition in region units may be used according to a desired configuration. As a machine learning model that performs object recognition, for example, RCNN, Fast-RCNN, or Faster-RCNN can be used. In addition, YOLO or SSD can also be used as a machine learning model that performs object recognition in region units.

Further, the machine learning model may be, for example, a capsule network (CapsNet). In this case, in a common neural network, by configuring each unit (each neuron or each node) so as to output a scalar value, the neural network is configured so that, for example, spatial information relating to spatial positional relationships (relative positions) between features in an image is reduced. By this means, for example, learning can be performed in which the influence of local distortion or parallel displacement in an image is reduced. On the other hand, in a capsule network, each unit (each capsule) is configured so as to output spatial information as a vector, and for example, is configured so that spatial information is held. By this means, for example, learning can be performed in which spatial positional relationships (relative positions) between features in an image is taken into consideration.

Modification 14

In the embodiment and modifications described above, in a case where various kinds of learned model are performing incremental learning, there is a probability that it will be difficult to output (infer/predict) using a learned model which is performing incremental learning. Therefore, it is good to adopt a configuration so as to prohibit input of a medical image other than training data to a learned model which is performing incremental learning. Further, a learned model that is the same as the learned model before performing incremental learning may be prepared as a separate auxiliary learned model. At such time, it is good to adopt a configuration so that input of a medical image other than training data to the auxiliary learned model can be executed while the incremental learning is being performed. Subsequently, after the incremental learning is completed, the learned model which performed the incremental learning is evaluated, and if there is no problem, it suffices to switch from the auxiliary learned model to the learned model which performed the incremental learning. Further, a configuration may be adopted so that the auxiliary learned model is used if there is a problem.

Note that, as the evaluation of the learned model after performing the incremental learning, for example, a learned model for classification for classifying a high quality image obtained with the learned model for improving image quality separately from other kinds of images may be used. The learned model for classification may be, for example, a learned model obtained by performing learning using training data that adopts a plurality of images including a high quality image obtained with the learned model for improving image quality and a low quality image as input data, and adopts data in which the kinds of these images have been labeled (annotated) as correct answer data. At such time, the kinds of images of the input data at the time of estimation (time of prediction) may be displayed in combination with information (for example, a numerical value indicating a percentage) indicating a likelihood for each kind of image included in the correct answer data during learning. Note that, apart from the aforementioned images, a high quality image for which the contrast was increased or noise was reduced or the like by averaging processing of a plurality of low quality images (for example, averaging processing of a plurality of low quality images that were aligned and obtained) may be included as input data of the learned model for classification. Further, as the evaluation of the learned model after performing incremental learning, for example, a plurality of high quality images obtained from the same image using each of the learned model after performing incremental learning and the learned model prior to performing incremental learning (the auxiliary learned model) may be compared, or the analysis results for each plurality of high quality images may be compared. At such time, for example, whether or not a result of comparing each of the plurality of high quality images (one example of a change caused by incremental learning), or a result of comparing analysis results for each of the plurality of high quality images (one example of a change caused by incremental learning) is within a predetermined range may be determined, and the determination result may be displayed.

Further, a configuration may be adopted so that learned models obtained by learning for respective imaged sites can be selectively utilized. Specifically, a plurality of learned models can be prepared that include a first learned model obtained using training data including a first imaged site (for example, an anterior ocular segment, posterior ocular segment, or the like), and a second learned model obtained using training data including a second imaged site that is different from the first imaged site. Further, the controlling unit 20 may have a selecting unit for selecting any one of this plurality of learned models. At such time, the controlling unit 20 may have a control unit for executing incremental learning with respect to a selected learned model. The control unit can, in accordance with an instruction from the examiner, retrieve data in which an imaged site corresponding to a selected learned model and an image obtained by imaging the relevant imaged site form a pair, and execute learning in which the retrieved and obtained data is adopted as training data, as incremental learning with respect to the selected learned model. Note that, an imaged site corresponding to a selected learned model may be a site obtained based on header information of data, or a site that is manually input by the examiner. Further, retrieval of data may be performed, for example, through a network from a server or the like of an external facility such as a hospital or a laboratory. By this means, incremental learning can be efficiently performed for each imaged site by using an image obtained by imaging an imaged site that corresponds to the learned model.

Note that, the selecting unit and the control unit may be constituted by a software module that is executed by a processor such as an MPU or a CPU of the controlling unit 20. Further, the selecting unit and the control unit may be constituted by a circuit that serves a specific function such as an ASIC or by an independent apparatus or the like.

Further, when obtaining training data for incremental learning through a network from a server or the like of an external facility such as a hospital or a laboratory, it is useful to reduce a decrease in reliability due to falsification or system trouble during incremental learning or the like. Therefore, the correctness of the training data for incremental learning may be detected by confirming the consistency by a digital signature or hashing. By this means the training data for incremental learning can be protected. At such time, in a case where the correctness of the training data for incremental learning could not be detected as the result of confirming the consistency by a digital signature or hashing, a warning to that effect is given and incremental learning is not performed using the training data in question. Note that, the server may be any form of server, such as a cloud server, a FOG server, or an edge server, regardless of the installation location thereof. Note that, in a case where a network within the facility, or within premises in which the facility is included, or within an area in which a plurality of facilities are included or the like is configured to enable wireless communication, for example, the reliability of the network may be improved by configuring the network to use radio waves in a dedicated wavelength band allocated to only the facility, the premises, or the area or the like. Further, the network may be constituted by wireless communication that is capable of high speed, large capacity, low delay, and many simultaneous connections.

Further, protection of data by confirming the consistency as described above is not limited to training data for incremental learning, and is also applicable to data including medical images. In addition, an image management system may be configured so that transactions involving data including medical images between servers of a plurality of facilities are managed by a distributed network. Furthermore, an image management system may be configured so as to connect a plurality of blocks in which a transaction history and a hash value of the previous block are recorded together, in time series. Note that, cryptography (for example, lattice-based cryptography, or quantum cryptography using quantum key distribution) that is difficult to calculate even if a quantum computer based on a quantum gate system or the like is used may be utilized as a technique for confirming the consistency or the like. Here, the image management system may be an apparatus and a system which receive and store images that were imaged by an imaging apparatus and images that were subjected to image processing. Further, the image management system can transmit an image in response to a request from a connected apparatus, perform image processing on a stored image, and request another apparatus to carry out a request for image processing. Examples of the image management system can include a picture archiving and communication system (PACS). Further, the image management system includes a database that is also capable of storing, together with a received image, various kinds of information such as information pertaining to the subject and the imaging time which is associated with the image. Further, the image management system is connected to a network and, in response to a request from another apparatus, can transmit and receive images, convert images, and transmit and receive various kinds of information associated with stored images.

Note that, with regard to the various learned models, when performing incremental learning, processing can be performed at high speed using a GPU. A GPU can perform efficient arithmetic operations by performing parallel processing of larger amounts of data, and therefore in a case where learning is performed a plurality of times using a learning model such as deep learning, it is effective to perform processing with a GPU. Note that, a GPU and a CPU or the like may cooperate to perform processing for incremental learning.

Modification 15

In the embodiments and modifications described above, an instruction from the examiner may be a voice instruction or the like in addition to a manual instruction (for example, an instruction using a user interface or the like). At such time, for example, a machine learning model including a voice recognition model (a voice recognition engine or a learned model for voice recognition) obtained by machine learning may be used. In addition, a manual instruction may be an instruction by character input using a keyboard, a touch panel, or the like. At such time, for example, a machine learning model including a character recognition model (a character recognition engine or a learned model for character recognition) obtained by machine learning may be used. Further, an instruction from the examiner may be an instruction by a gesture or the like. At such time, a machine learning model including a gesture recognition model (a gesture recognition engine or a learned model for gesture recognition) obtained by machine learning may be used.

Further, an instruction from the examiner may be a result of detection of the line of sight of the examiner on a display screen of the display unit 40. The line-of-sight detection result may be, for example, a pupil detection result using a moving image of the examiner obtained by imaging from around the display screen of the display unit 40. At such time, the pupil detection from the moving image may use an object recognition engine as described above. Further, an instruction from the examiner may be an instruction by brain waves, or a faint electric signal flowing through the body or the like.

In such a case, for example, the training data may be training data in which character data or voice data (waveform data) or the like indicating an instruction to display a result obtained by processing of various learned models as described above is adopted as input data, and an execution command for causing a result obtained by processing of various learned models to be actually displayed on a display unit 40 is adopted as correct answer data. Further, the training data may be training data in which, for example, character data or voice data or the like indicating an instruction to display a high quality image obtained with a learned model for improving image quality is adopted as input data, and an execution command for displaying a high quality image and an execution command for changing an image quality improving button to an active state are adopted as correct answer data. Note that, any kind of training data may be used as long as, for example, the instruction content indicated by the character data or voice data or the like and the execution command content correspond with each other. Further, voice data may be converted to character data using an acoustic model or a language model or the like. Further, processing that reduces noise data superimposed on voice data may be performed using waveform data obtained with a plurality of microphones. Further, a configuration may be adopted so that a selection between an instruction issued by characters or voice or the like and an instruction input using a mouse or a touch panel or the like can be made according to an instruction from the examiner. In addition, a configuration may be adopted so that a selection can be made to turn instruction by characters or voice or the like on or off according to an instruction from the examiner.

Here, deep learning that is described above may be used for machine learning with respect to a learned model for voice recognition, a learned model for character recognition, or a learned model for gesture recognition. Further, for example, the aforementioned RNN can be used for at least one part of a multi-layer neural network. Furthermore, the aforementioned LSTM that is one kind of RNN may also be used. Further, a QRNN may be used instead of an LSTM. In addition, the machine learning model is not limited to a neural network, and Boosting or Support Vector Machine or the like may be used. Further, in a case where an instruction from the examiner is input by characters or voice or the like, a technique relating to natural language processing (for example, Sequence to Sequence) may be applied. At such time, as a technique relating to natural language processing, for example, a model output for each input sentence may be applied. Further, the various learned models described above are not limited to the instructions from the examiner, and may be applied to the output to the examiner. Further, a dialogue engine (a dialogue model or a learned model for dialogue) that responds to the examiner with an output such as character or voice may be applied.

Further, as a technique relating to natural language processing, a learned model obtained by pre-learning by unsupervised learning of document data may be used. Further, as a technique relating to natural language processing, a learned model obtained by further subjecting a learned model obtained by pre-learning to transfer learning (or fine-tuning) according to the purpose may be used. Furthermore, for example, BERT (Bidirectional Encoder Representations from Transformers) may be applied as a technique relating to natural language processing. In addition, a model that is capable of, by itself, extracting (representing) the context (feature value) by predicting specific words in a sentence from the bidirectional context may be applied as a technique relating to natural language processing. Furthermore, a model that is capable of determining the relationship (continuity) of two sequences (sentences) in time series data that is input may be applied as a technique relating to natural language processing. Further, a model in which an encoder of a transformer is used in a hidden layer, and into which a vector sequence is input and is output from may be applied as a technique relating to natural language processing.

Here, an instruction from the examiner that can be applied in the present modification may be any instruction as long as the instruction is at least one instruction relating to changing the display of various images or analysis results, selection of a depth range for generating an en-face image, selection of whether or not to use an image as training data for incremental learning, selection of a learned model, and output (display or transmission or the like) or storage of results obtained using various learned models and the like as described in the various embodiments and modifications described above. Further, an instruction from the examiner that can be applied in the present modification is not only an instruction after imaging, and may be an instruction before imaging, and for example, may be an instruction relating to various adjustments, an instruction relating to the setting of various imaging conditions, or an instruction relating to the start of imaging. In addition, an instruction from the examiner that can be applied in the present modification may be an instruction relating to changing of a display screen (screen transition).

Note that, the machine learning model may be a machine learning model that combines a machine learning model relating to images such as a CNN and a machine learning model relating to time series data such as an RNN. With such a machine learning model, for example, the relationship between a feature value relating to an image and a feature value relating to time series data can be learned. In a case where the input layer side of the machine learning model is a CNN and the output layer side is an RNN, for example, learning may be performed using training data in which a medical image is adopted as input data, and sentences relating to the medical image (for example, the presence or absence of a lesion, the type of lesion, a recommendation for the next examination and the like) is adopted as a ground truth. By this means, for example, since medical information relating to a medical image is automatically described in sentences, even an examiner with little medical treatment experience can easily ascertain medical information relating to the medical image. Further, in a case where the input layer side of the machine learning model is an RNN and the output layer side is a CNN, for example, learning may be performed using training data in which sentences relating to medical treatment such as a lesion, findings, and a diagnosis are adopted as input data, and a medical image corresponding to the sentences relating to the medical treatment is adopted as a ground truth. By this means, for example, a medical image relating to a case that an examiner wants to check can be easily searched for.

Further, a machine translation engine (machine translation model, learned model for machine translation) that performs machine translation of sentences of character, voice or the like into an arbitrary language may be used with respect to the instructions from the examiner or the output to the examiner. Note that, a configuration may be adopted so that an arbitrary language can be selected according to an instruction from the examiner. Further, a configuration may be adopted that enables an arbitrary language to be automatically selected by using a learned model that automatically recognizes types of languages. Further, a configuration may be adopted that enables the type of language that was automatically selected to be modified according to an instruction from the examiner. For example, a technique (for example, Sequence to Sequence) relating to the aforementioned natural language processing may be applied to the machine translation engine. For example, a configuration may be adopted so that after a sentence that was input to the machine translation engine has been machine-translated, the machine-translated sentence is input to a character recognition engine or the like. Further, for example, a configuration may be adopted so that sentences which were output from various learned models mentioned above are input to a machine translation engine, and sentences which were output from the machine translation engine are output.

Further, the various learned models mentioned above may be used in combination. For example, a configuration may be adopted so that characters corresponding to an instruction from the examiner are input to a character recognition engine, and voice obtained from the input characters is input to another type of machine learning engine (for example, a machine translation engine). Further, for example, a configuration may be adopted so that characters output from the other type of machine learning engine are input to a character recognition engine, and voice obtained from the input characters is output. Furthermore, for example, a configuration may be adopted so that voice corresponding to an instruction from the examiner is input to a voice recognition engine, and characters obtained from the input voice are input to another type of machine learning engine (for example, a machine translation engine). Further, for example, a configuration may be adopted so that voice that is output from the other type of machine learning engine is input to a voice recognition engine, and characters obtained from the input voice are displayed on the display unit 40. At such time, a configuration may be adopted so that whether an output to the examiner is to be an output by characters or an output by voice can be selected according to an instruction from the examiner. Further, a configuration may be adopted so that whether an instruction from the examiner is to be an input by characters or an input by voice can be selected according to an instruction from the examiner. Furthermore, a configuration may be adopted so that various configurations described above can be adopted depending on a selection made by an instruction from the examiner.

Modification 16

A label image, a high quality image, or the like relating to an image obtained by actual imaging may be stored in the storage 27 according to an instruction from the operator. At such time, for example, after an instruction from the operator to save a high quality image, when registering a file name, a file name that includes information (for example, characters) indicating that the image is an image generated by processing using a learned model for improving image quality (image quality improving processing) at any part of the file name (for example, the first part or the last part) may be displayed as a recommended file name in a state in which the file name can be edited according to an instruction from the operator. Note that, with respect to a label image or the like also, a file name including information indicating that the image is an image generated by processing using a learned model may be displayed in a similar manner.

Further, when causing the display unit 40 to display a high quality image on various display screens such as the report screen, a display indicating that the image being displayed is a high quality image generated by processing using an image quality improving model may be displayed together with the high quality image. In this case, since the operator can easily discern by the relevant display that the displayed high quality image is not the actual image obtained by imaging, misdiagnosis can be reduced and the diagnosis efficiency can be improved. Note that, a display indicating that a high quality image was generated by processing that used an image quality improving model may be of any form as long as it is a display which makes it possible to distinguish between the input image and the high quality image generated by the relevant processing. Further, with regard to processing using various learned models as described above also, and not just processing using an image quality improving model, a display indicating that the result being displayed was generated by processing using the relevant kind of learned model may be displayed together with the relevant result. For example, when displaying an analysis result with respect to segmentation results obtained using a learned model for image segmentation processing also, a display indicating that the analysis result is based on results obtained using a learned model for image segmentation may be displayed together with the analysis result.

At such time, the display screen such as a report screen may be stored in the storage 27 as an image data in accordance with an instruction from the operator. For example, a report screen may be stored in the storage 27 as a single image in which high quality images or the like and a display indicating that these images are images generated by processing using a learned model are displayed side by side.

Further, with respect to the display indicating that a high quality image was generated by processing that used an image quality improving model, a display indicating what kind of training data the image quality improving model used when performing learning may be displayed on the display unit 40. The display in question may include a display of a description of the kinds of input data and correct answer data of the training data, or any display relating to the input data and the correct answer data such as an imaged site included in the correct answer data. Note that, with regard to processing using the various kinds of learned models as described above such as image segmentation processing also, a display indicating what kind of training data the relevant kind of learned model used when performing learning may be displayed on the display unit 40.

A configuration may also be adopted so that information (for example, characters) indicating that an image was generated by processing using a learned model is displayed or stored in a state in which the information is superimposed on the image or the like. At such time, a place at which the information is superimposed on the image may be any place as long as the place is in a region (for example, at an edge of the image) which does not overlap with a region in which the site of interest or the like that is the imaging target is displayed. Further, a non-overlapping region may be determined, and the information may be superimposed in the determined region. Note that, processing may be performed in a similar manner with respect to, for example, an image obtained by processing that used the various kinds of learned models described above such as image segmentation processing, and not just processing that used an image quality improving model.

Further, a configuration may be adopted so that in a case where, as an initial display screen of the report screen, the default setting is set so that the image quality improving button or the like enters an active state (image quality improving processing is set to "on"), a report image corresponding to the report screen that includes a high quality image or the like is transmitted to a server in accordance with an instruction from the examiner. Further, a configuration may be adopted so that in a case where the default setting is set so that the button enters an active state, when an examination ends (for example, in a case where the imaging confirmation screen or the preview screen is changed to the report screen in accordance with an instruction from the examiner), a report image corresponding to the report screen that includes a high quality image or the like is (automatically) transmitted to a server. At such time, a configuration may be adopted so that a report image generated based on various kinds of settings of the default settings (for example, settings relating to at least one of the depth range for generating an en-face image on the initial display screen of the report screen, whether or not to superimpose an analysis map, whether or not the image is a high quality image, and whether or not to show a display screen for follow-up observation and the like) is transmitted to a server. Note that, similar processing may be performed in relation to a case where the button represents switching of image segmentation processing also.

Modification 17

In the embodiments and modifications described above, among the aforementioned various kinds of learned models, an image obtained with a first kind of learned model (for example, a high quality image, an image showing an analysis result such as an analysis map, an image showing a predetermined region recognition result or an image showing a segmentation result) may be input to a second kind of learned model that is different from the first kind. At such time, a configuration may be adopted so that a result (for example, an analysis result, a diagnosis result, a predetermined region recognition result or a segmentation result) is generated by processing of the second kind of learned model.

Further, among the various kinds of learned models described above, an image to be input to a second kind of learned model that is different from a first kind of learned model may be generated from an image input to the first kind of learned model by using a result (for example, an analysis result, a diagnosis result, a predetermined region recognition result or a segmentation result) obtained by processing of the first kind of learned model. At such time, there is a high probability that the generated image is an image that is suitable as an image for processing using the second kind of learned model. Therefore, the accuracy of an image (for example, a high quality image, an image showing an analysis result such as an analysis map, an image showing a predetermined region recognition result or an image showing a segmentation result) obtained when the generated image is input to the second kind of learned model can be enhanced.

Note that, a configuration may be adopted so that, by inputting a common image into the first kind of learned model and the second kind of learned model, the generation (or display) of results of various kinds of processing using these learned models can be performed. At such time, for example, a configuration may be adopted so that, according to an instruction from the examiner, the generation (or display) of respective processing results obtained using these learned models is executed collectively (cooperatively). Further, a configuration may be adopted so that the type of image to be input (for example, a high quality image, an image showing an object recognition result, an image showing a segmentation result, or a similar case image), the type of processing result (for example, a high quality image, a diagnosis result, an analysis result, an object recognition result, a segmentation result, or a similar case image) to be generated (or displayed), and the type of input and the type of output (for example, characters, voice, language) and the like can each be selected according to an instruction from the examiner. Further, a configuration may be adopted so that the type of input can be automatically selected by using a learned model that automatically recognizes the type of an input. Further, a configuration may be adopted so that the type of output can be automatically selected so as to correspond to the type of input (for example, so as to be the same type). In addition, a configuration may be adopted so that a type that was automatically selected can be modified according to an instruction from the examiner. At such time, a configuration may be adopted so that at least one learned model is selected according to the selected type. At such time, in a case where a plurality of learned models are selected, the manner in which to combine the plurality of learned models (for example, the order in which data is input) may be determined according to the selected type. Note that, for example, a configuration may be adopted so that a selection can be made so that the type of image to be input and the type of processing result to be generated (or displayed) differ, and a configuration may be adopted so that in a case where the types are the same, information prompting the examiner to make a selection so that the types differ from each other is output to the examiner. Further, each learned model may be executed at any location. For example, a configuration may be adopted so that some of the plurality of learned models are used by a cloud server, and the other learned models are used by another server such as a fog server or an edge server. Note that, in a case where a network within the facility, or within premises in which the facility is included, or within an area in which a plurality of facilities are included or the like is configured to enable wireless communication, for example, the reliability of the network may be improved by configuring the network to use radio waves in a dedicated wavelength band allocated to only the facility, the premises, or the area or the like. Further, the network may be constituted by wireless communication that is capable of high speed, large capacity, low delay, and many simultaneous connections. By these means, for example, surgery with respect to the vitreous body, a cataract, glaucoma, corneal refraction correction, the external eye or the like, and treatment such as laser photocoagulation can be supported in real time even if the surgery is at a remote location. At such time, for example, a configuration may be adopted so that a fog server or an edge server or the like that received at least one of various medical images obtained by an apparatus relating to these surgeries or treatments by wireless communication transmits, by wireless communication, information obtained using at least one of various learned models to an apparatus relating to surgery or treatment. Further, for example, the information which the apparatus relating to surgery or treatment received by wireless communication may be a movement amount (vector) of an optical system or an optical member as described above, and in such case, a configuration may be adopted so that the apparatus relating to surgery or treatment is automatically controlled. Further, for example, a configuration may be adopted in which, for the purpose of assisting operations by the examiner, automatic control is performed with the permission of the examiner (semi-automatic control).

Further, search of similar case images utilizing an external database that is stored in a server or the like may be performed using, as a search key, an analysis result or a diagnosis result or the like obtained by processing of a learned model that is described above. Further, search of similar case images utilizing an external database that is stored in a server or the like may be performed using, as a search key, an object recognition result or a segmentation result or the like obtained by processing of various learned models as described above. Note that, in a case where a plurality of medical images stored in the database are already being managed in a state in which respective feature values of the plurality of medical images have been attached as supplementary information by machine learning or the like, a similar case image search engine (a similar case image search model, or a learned model for similar case image searching) that utilizes a medical image itself as a search key may be used. For example, the controlling unit 20 can perform a search for a similar case image relating to the relevant medical image from among various medical images by using a learned model for similar case image searching (that is different from the learned model for improving image quality). Further, for example, the display controlling unit 28 can cause a similar case image obtained using the learned model for similar case image searching from among various medical images to be displayed on the display unit 40. At such time, the similar case image is, for example, an image with a feature value that is similar to the feature value of the medical image input to the learned model. Further, in a case where, for example, a partial region such as an abnormal site is included in the medical image input to the learned model, the similar case image is an image with a feature value that is similar to the feature value of the partial region such as an abnormal site. Therefore, for example, not only can learning for accurately searching for a similar case image be efficiently performed, but furthermore, in a case where an abnormal site is included in a medical image, the examiner can efficiently make a diagnosis with respect to the abnormal site. Further, a plurality of similar case images may be retrieved, and the plurality of similar case images may be displayed in a condition in which the order in which the feature values are similar can be distinguished. Further, a configuration may be adopted so that the learned model for similar case image searching is subjected to incremental learning using training data that includes an image selected according to an instruction from the examiner from among a plurality of similar case images, and a feature value of the relevant image.

Further, in the learned models for detecting predetermined region, improving image quality, image segmentation processing, or the like according to the examples and modifications described above, it is conceivable for the magnitude of intensity values of a tomographic image, and the order and slope, positions, distribution, and continuity of bright sections and dark sections and the like of a tomographic image to be extracted as a part of the feature values and used for estimation processing. On the other hand, in the case of the learned models for voice recognition, for character recognition, for gesture recognition and the like, since learning that uses time-series data is performed, it is conceivable to also extract a slope between consecutive time-series data values that are input, as a part of the feature values, and to use the slope for estimation processing. Therefore, it is expected that such learned models can be utilized to perform estimation with excellent accuracy by using influences caused by changes over time in specific numerical values in estimation processing.

Further, the learning data of the various kinds of learned models is not limited to data obtained using the ophthalmic apparatus itself that performs the actual imaging, and according to a desired configuration, the learning data may be data obtained using an ophthalmic apparatus of the same model, or may be data obtained using an ophthalmic apparatus of the same kind.

Note that, the various kinds of learned models according to the above embodiments and modifications can be provided in the controlling unit 20. These learned models, for example, may be constituted by a software module that is executed by a processor such as a CPU, an MPU, a GPU or an FPGA, or may be constituted by a circuit that serves a specific function such as an ASIC. Further, these learned models may be provided in a different apparatus such as a server that is connected to the controlling unit 20. In this case, the controlling unit 20 can use the learned models by connecting to the server or the like that includes the learned models through any network such as the Internet. The server that includes the learned models may be, for example, a cloud server, a FOG server, or an edge server. Note that, in a case where a network within the facility, or within premises in which the facility is included, or within an area in which a plurality of facilities are included or the like is configured to enable wireless communication, for example, the reliability of the network may be improved by configuring the network to use radio waves in a dedicated wavelength band allocated to only the facility, the premises, or the area or the like. Further, the network may be constituted by wireless communication that is capable of high speed, large capacity, low delay, and many simultaneous connections.

Modification 18

Medical images to be processed by the controlling unit 20 according to the various embodiments and modifications described above include images obtained using an arbitrary modality (imaging apparatus or imaging method). The medical images to be processed can include a medical image obtained by any imaging apparatus or the like, and images created by a medical image processing apparatus or a medical image processing method in accordance with the embodiments and modifications described above.

In addition, a medical image to be processed is an image of a predetermined site of a subject (examinee), and the image of the predetermined site includes at least one part of the predetermined site of the subject. The medical image may also include another site of the subject. The medical image may be a still image or a moving image, and may be a black and white image or a color image. In addition, the medical image may be an image representing the structure (form) of the predetermined site or may be an image representing a function of the predetermined site. Images that represent a function include, for example, an image representing hemodynamics (blood flow volume, blood flow velocity or the like) such as an OCTA image, a Doppler OCT image, an fMRI image, and an ultrasound Doppler image. Note that, the predetermined site of the subject may be determined according to the imaging target, and the predetermined site includes any site such as an organ such as the human eye (eye to be examined), brain, lung, intestine, heart, pancreas, kidney, and liver, and the head, chest, legs and arms.

Further, the medical image may be a tomographic image of the subject, or may be a front image. Examples of a front image include a front image of the ocular fundus, a front image of the anterior ocular segment, a fundus image obtained by fluorescence imaging, and an en-face image generated using at least a partial range of data in the depth direction of the imaging target with respect to data obtained by OCT (three-dimensional OCT data). Note that, an en-face image may be an OCTA en-face image (motion contrast front image) generated using at least a partial range of data in the depth direction of the imaging target with respect to three-dimensional OCTA data (three-dimensional motion contrast data). Further, three-dimensional OCT data or three-dimensional motion contrast data is an example of three-dimensional medical image data.

Here, the term "motion contrast data" refers to data showing changes between a plurality of items of volume data obtained by controlling so that measuring light is scanned a plurality of times over the same region (same position) of an eye to be examined. At such time, the volume data is composed of a plurality of tomographic images obtained at different positions. The motion contrast data can then be obtained as volume data by, at respective positions that are different to each other, obtaining data showing changes between a plurality of tomographic images that were obtained at approximately the same position. Note that, in relation to OCT angiography (OCTA) that measures blood flow movement, a motion contrast front image is also referred to as an OCTA front image (OCTA en-face image), and motion contrast data is also referred to as OCTA data. The motion contrast data can be obtained, for example, as a variance value or a decorrelation value between two tomographic images or between interference signals corresponding to the two tomographic images, or as a value obtained by dividing a maximum value by a minimum value (maximum value/minimum value), and may be obtained by any known method. At such time, the two tomographic images can be obtained, for example, by controlling so that measuring light is scanned a plurality of times over the same region (same position) of the eye to be examined. Note that, when controlling the scanning unit so that measuring light is scanned a plurality of times over approximately the same position, a configuration may be adopted so that a time interval between one scan (one B scan) and the next scan (next B scan) is changed (determined). By this means, for example, even if there is a case where blood flow velocities differ due to the state of a blood vessel, the vascular zone can be accurately visualized. At such time, for example, a configuration may be adopted so that the aforementioned time interval can be changed according to an instruction from the examiner. Further, for example, a configuration may be adopted so that any motion contrast image can be selected according to an instruction from the examiner from a plurality of motion contrast images corresponding to a plurality of time intervals that were set in advance. Further, for example, a configuration may be adopted so that a time interval when motion contrast data was obtained and the relevant motion contrast data can be stored in association with each other in the storage 27. Further, for example, the display controlling unit 28 may cause a time interval when motion contrast data was obtained and a motion contrast image corresponding to the relevant motion contrast data to be displayed on the display unit 40. Further, for example, a configuration may be adopted so that the time interval is automatically determined, or at least one candidate for the time interval is determined. At such time, for example, a configuration may be adopted so that the time interval is determined (output) based on a motion contrast image using a machine learning model. Such a machine learning model can be obtained by, for example, performing learning using training data in which a plurality of motion contrast images corresponding to a plurality of time intervals are adopted as input data, and a difference from the plurality of time intervals to a time interval when a desired motion contrast image is obtained is adopted as correct answer data.

Further, an en-face image is, for example, a front image generated by projecting data of a range between two layer boundaries in the X- and Y-directions. At such time, the front image is generated by projecting or integrating data corresponding to a depth range that is at least a partial depth range of volume data (a three-dimensional tomographic image) obtained using light interference and that is defined based on two reference planes onto a two-dimensional plane. The en-face image is a front image generated by, among volume data, projecting data corresponding to a depth range which is determined based on detected retinal layers onto a two-dimensional plane. Note that, as a technique for projecting data corresponding to a depth range defined based on two reference planes onto a two-dimensional plane, for example, a technique can be used in which representative values of data within the relevant depth range are adopted as pixel values on a two-dimensional plane. In this case, the representative values can include values such as an average value, a median value or a maximum value of pixel values within a range in the depth direction of the region surrounded by the two reference planes. Further, the depth range pertaining to the en-face image may be, for example, a range that includes only a range corresponding to a predetermined number of pixels in a deeper direction or a shallower direction with reference to one of the two layer boundaries relating to the detected retinal layers. In addition, the depth range pertaining to the en-face image may be, for example, a range that has been changed (offset) according to an instruction of the operator from a range between the two layer boundaries relating to the detected retinal layers.

In addition, the term "imaging apparatus" refers to an apparatus for performing imaging to obtain an image to be used for diagnosis. Examples of an imaging apparatus include an apparatus that obtains an image of a predetermined site of the subject by irradiating the predetermined site with light, radioactive rays such as X-rays, electromagnetic waves, or ultrasonic waves or the like, and an apparatus that obtains an image of a predetermined site by detecting radioactive rays emitted from the subject. More specifically, examples of an imaging apparatus according to the various examples and modifications described above include at least an X-ray imaging apparatus, a CT apparatus, an MRI apparatus, a PET apparatus, a SPECT apparatus, an SLO apparatus, an OCT apparatus, an OCTA apparatus, a fundus camera and an endoscope.

Note that, a time domain OCT (TD-OCT) apparatus and a Fourier domain OCT (FD-OCT) apparatus may be included as examples of an OCT apparatus. Further, examples of a Fourier domain OCT apparatus may include a spectral domain OCT (SD-OCT) apparatus and a swept source OCT (SS-OCT) apparatus. Further, a Line-OCT apparatus (or an SS-Line-OCT apparatus) that uses line light may be included as an example of the OCT apparatus. Furthermore, a Full Field-OCT apparatus (or an SS-Full Field-OCT apparatus) that uses area light may be included as an example of the OCT apparatus. Further, a Doppler-OCT apparatus may be included as an example of the OCT apparatus. Further, an adaptive optics SLO (AO-SLO) apparatus and an adaptive optics OCT (AO-OCT) apparatus that use an adaptive optics system and the like may be included as examples of an SLO apparatus or an OCT apparatus, respectively. Furthermore, a polarization-sensitive SLO (PS-SLO) apparatus and a polarization-sensitive OCT (PS-OCT) apparatus and the like for visualizing information relating to polarization phase differences or depolarization may be included as examples of an SLO apparatus or an OCT apparatus, respectively. In addition, a pathology microscope SLO apparatus and a pathology microscope OCT apparatus and the like may be included as examples of an SLO apparatus and an OCT apparatus, respectively. Further, a hand-held type SLO apparatus and a hand-held type OCT apparatus and the like may be included as examples of an SLO apparatus and an OCT apparatus, respectively. In addition, a catheter SLO apparatus and a catheter OCT apparatus and the like may be included as examples of an SLO apparatus and an OCT apparatus, respectively. Further, a head-mounted SLO apparatus and a head-mounted OCT apparatus and the like may be included as examples of an SLO apparatus and an OCT apparatus, respectively. Further, a binocular-type SLO apparatus and a binocular-type OCT apparatus may be included as examples of an SLO apparatus and an OCT apparatus, respectively. Further, the SLO apparatus or OCT apparatus may be capable of changing the imaging angle of view by having a configuration capable of optical scaling. Further, the SLO apparatus may be capable of obtaining a color image or a fluorescence image by having a configuration in which light is received by a single light receiving element in a time-division manner or a configuration in which light is simultaneously received by a plurality of light receiving elements, using light sources for each of R, G and B.

According to the various embodiments and modifications described above of the present invention, when performing imaging of an image relating to the fundus of an eye to be examined, the complexity of various kinds of adjustment operations relating to the apparatus such as adjustment of alignment positions can be reduced.

Other Examples

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

At this time, examples of the processor or circuit may include a central processing unit (CPU), a microprocessing unit (MPU), a graphics processing unit (GPU), an application specific integrated circuit (ASIC), or a field programmable gateway (FPGA). Further, examples of the processor or circuit may include a digital signal processor (DSP), a data flow processor (DFP) or a neural processing unit (NPU).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An ophthalmic apparatus comprising:
   a first optical head unit including an optical system arranged to irradiate a first eye to be examined with light and to detect return light from the first eye to be examined;
   an information obtaining unit configured to, using a first image relating to the first eye to be examined that is obtained using the first optical head unit as input data of a learned model, the learned model having been obtained by using (1) a second image relating to a second eye to be examined, the second image having been obtained using a second optical head unit and (2) information of a position relating to at least one of the second eye to be examined and the second optical head unit, obtain, as output data from the learned model, information of a position relating to at least one of the first eye to be examined and the first optical head unit; and
   a drive controlling unit configured to control driving of at least one of a supporter arranged to support a face of a subject and the first optical head unit,
   wherein the drive controlling unit is configured to control the driving of the at least one of the supporter and the first optical head unit based on the obtained information of the position to cause at least one of the first eye to be examined and the first optical head unit to move to the position,
   wherein the first image relating to the first eye to be examined includes a first image relating to a fundus of the first eye to be examined,
   wherein the second image relating to the second eye to be examined includes a second image relating to a fundus of the second eye to be examined,
   wherein the information obtaining unit is configured to, using the first image relating to the fundus of the first eye to be examined that is obtained using the first optical head unit as input data of the learned model, the learning model having been obtained by using (a) the second image relating to the fundus of the second eye to be examined, the second image having been obtained using the second optical head unit, (b) information of a position relating to at least one of the second eye to be examined and the second optical head unit, (c) information of a position relating to a focusing optical system, and (d) information of a position relating to an coherence gate, obtain, as output data from the learned model, information of positions relating to (a) at least one of the first eye to be examined and the first optical head unit, (b) the focusing optical system, and (c) the coherence gate, and
   wherein the drive controlling unit is configured to adjust an arrangement of at least one of the supporter and the first optical head unit, the focusing optical system, and the coherence gate based on the obtained information of the positions relating to (a) at least one of the first eye to be examined and the first optical head unit, (b) the focusing optical system, and (c) the coherence gate.

2. An ophthalmic apparatus according to claim 1, wherein the information obtaining unit is configured so that, after obtaining information of a first position obtained based on the first image relating to the first eye to be examined that is obtained using the first optical head unit, the information obtaining unit is capable of obtaining information of a second position that is obtained using the learned model, and
   wherein the drive controlling unit is configured to:
   (1) control the driving of the at least one of the supporter and the first optical head unit based on the obtained information of the first position to move at least one of the first eye to be examined and the first optical head unit to the first position, and
   (2) control the driving of the at least one of the supporter and the first optical head unit based on the obtained information of the second position to move at least one of the first eye to be examined and the first optical head unit to the second position.

3. An ophthalmic apparatus according to claim 1, wherein the learned model is a machine learning model obtained by using information of a position relating to at least one of the second eye to be examined and the second optical head unit in a case where an optical axis of a light flux from the second optical head unit is shifted from a centroid of a pupil of the second eye to be examined, and
   wherein the information obtaining unit is configured to obtain the information of the position at a time that is at least one of before and after a measurement relating to a fundus of the first eye to be examined.

4. An ophthalmic apparatus according to claim 2, further comprising an evaluating unit configured to evaluate an image relating to a fundus that is obtained using the first optical head unit,
   wherein in a case where an evaluation value for an image relating to a fundus that is obtained at the first position is lower than a threshold, the information obtaining unit is configured to obtain information of the second position.

5. An ophthalmic apparatus according to claim 2, further comprising an evaluating unit configured to evaluate an image relating to a fundus that is obtained using the first optical head unit,
   wherein measurement relating to a fundus of the first eye to be examined is performed at a position at which an image relating to a fundus is obtained that has a higher evaluation value among (1) an evaluation value of an image relating to a fundus that is obtained at the first position and (2) an evaluation value of an image relating to a fundus that is obtained at the second position.

6. An ophthalmic apparatus according to claim 2, wherein in a case where the first eye to be examined is a predetermined diseased eye, the information obtaining unit is configured to obtain the information of the second position without obtaining the information of the first position.

7. An ophthalmic apparatus according to claim 1, wherein the learned model includes a plurality of learned models that performed learning using training data for each of a cataractous eye, an eye in which pupil decentration has occurred, an eye in which miosis has occurred, and a healthy eye, and
wherein the information obtaining unit is configured to obtain the information of the position using, from among the plurality of learned models, a learned model corresponding to a state of the first eye to be examined.

8. An ophthalmic apparatus according to claim 1, wherein the learned model performs incremental learning in which the obtained information of the position that is modified by an operator is used as training data.

9. An ophthalmic apparatus according to claim 1, wherein the learned model is:
(1) a machine learning model that learned using training data in which an image of an anterior ocular segment as the second image relating to the second eye to be examined is adopted as input data, and a movement amount from an alignment position when the image of the anterior ocular segment is obtained to a position of at least one of the second eye to be examined and the second optical head unit in a case where an optical axis of a light flux from the second optical head unit is shifted from a centroid of a pupil of the second eye to be examined is adopted as a ground truth; or
(2) a machine learning model that performed reinforcement learning in which an image of an anterior ocular segment as the second image relating to the second eye to be examined is adopted as input data, with the reinforcement learning being performed so as to maximize a reward relating to image quality of an image relating to a fundus.

10. An ophthalmic apparatus according to claim 1, wherein the learned model is a machine learning model obtained by subjecting a learned model obtained by learning using a model of an eye in advance to additional learning with a human eye.

11. An ophthalmic apparatus according to claim 1, wherein the first image relating to the first eye to be examined and the second image relating to the second eye to be examined are moving images, and
wherein the ophthalmic apparatus is any one of an optical coherence tomography apparatus, a fundus camera, a scanning laser ophthalmoscope, and an eye refractive power measuring apparatus.

12. An ophthalmic apparatus according to claim 1, further comprising a display controlling unit configured to cause a display unit to display the first image relating to the first eye to be examined obtained using the first optical head unit as a live moving image,
wherein the display controlling unit is configured to cause the display unit to display a high-quality image which is generated using a learned model obtained by using training data including a third image relating to a third eye to be examined, and which is a high-quality image obtained by inputting the first image relating to the first eye to be examined obtained using the first optical head unit.

13. An ophthalmic apparatus according to claim 12, wherein the display controlling unit is configured to: (a) cause the display unit to display, as the live moving image, an anterior ocular segment image generated as the high-quality image; (b) cause the display unit to display, as the live moving image, a fundus front image generated as the high-quality image that is a fundus front image on which a line indicating a position of a tomographic image generated as the high-quality image is displayed in a superimposed manner; (c) cause the display unit to display, as the live moving image, the tomographic image corresponding to a position of the line on the fundus front image; and (d) cause the display unit to display information indicating a vascular zone in a tomographic image corresponding to the position of the line that is a tomographic image generated as the high-quality image, in a superimposed manner on the tomographic image corresponding to the position of the line.

14. An ophthalmic apparatus according to claim 1, further comprising a display controlling unit configured to cause a display unit to display the first image relating to the first eye to be examined obtained using the first optical head unit as a live moving image,
wherein the display controlling unit is configured to cause the display unit to display at least one of:
(a) an analysis result generated using a learned model for analysis result generation obtained by using training data including a third image relating to a third eye to be examined, that is an analysis result obtained by inputting the first image relating to the first eye to be examined obtained using the first optical head unit;
(b) a diagnosis result generated using a learned model for diagnosis result generation obtained by using training data including a fourth image relating to a fourth eye to be examined, that is a diagnosis result obtained by inputting the first image relating to the first eye to be examined obtained using the first optical head unit;
(c) information relating to an abnormal site that is information relating to a difference between an image generated using a generative adversarial network or an auto-encoder, that is an image obtained by inputting the first image relating to the first eye to be examined obtained using the first optical head unit, and the first image relating to the first eye to be examined that is input to the generative adversarial network or auto-encoder;
(d) a similar case image searched using a learned model for similar case image searching obtained by using training data including a fifth image relating to a fifth eye to be examined, that is a similar case image obtained by inputting the first image relating to the first eye to be examined obtained using the first optical head unit; and
(e) an object recognition result or a segmentation result generated using a learned model for object recognition or a learned model for segmentation obtained by using training data including a sixth image relating to a sixth eye to be examined, that is an object recognition result or a segmentation result obtained by inputting the first image relating to the first eye to be examined.

15. An ophthalmic apparatus according to claim 1, wherein an instruction of an operator for obtaining the information of the position relating to at least one of the first eye to be examined and the first optical head unit is information obtained using at least one learned model among a learned model for character recognition, a learned model for voice recognition, and a learned model for gesture recognition.

16. An ophthalmic apparatus according to claim 1, wherein the learned model has been obtained by further using (1) a third image relating to the second eye to be examined, the third image having been obtained using the first optical head unit and (2) information of a position relating to at least one of the second eye to be examined and the first optical head unit.

17. A control method for an ophthalmic apparatus comprising a first optical head unit including an optical system arranged to irradiate a first eye to be examined with light and detect return light from the first eye to be examined, the control method including:

obtaining a first image relating to the first eye to be examined using the first optical head unit;

obtaining as output data from a learned model, using the first image relating to the first eye to be examined that is obtained using the first optical head unit as input data of the learned model, the learned model having been obtained by using (1) a second image relating to a second eye to be examined, the second image having been obtained using a second optical head unit and (2) information of a position relating to at least one of the second eye to be examined and the second optical head unit, information of a position relating to at least one of the first eye to be examined and the first optical head unit; and controlling driving of at least one of a supporter arranged to support a face of a subject and the first optical head unit, wherein the controlling includes controlling the driving of the at least one of the supporter and the first optical head unit based on the obtained information of the position to cause at least one of the first eye to be examined and the first optical head unit to move to the position, wherein the first image relating to the first eye to be examined includes a first image relating to a fundus of the first eye to be examined, wherein the second image relating to the second eye to be examined includes a second image relating to a fundus of the second eye to be examined, wherein the obtaining comprises, by using the first image relating to the fundus of the first eye to be examined that is obtained using the first optical head unit as input data of the learned model, the learning model having been obtained by using (a) the second image relating to the fundus of the second eye to be examined, the second image having been obtained using the second optical head unit, (b) information of a position relating to at least one of the second eye to be examined and the second optical head unit, (c) information of a position relating to a focusing optical system, and (d) information of a position relating to an coherence gate, obtaining, as output data from the learned model, information of positions relating to (a) at least one of the first eye to be examined and the first optical head unit, (b) the focusing optical system, and (c) the coherence gate, and wherein in the controlling, an arrangement of at least one of the supporter and the first optical head unit, the focusing optical system, and the coherence gate is adjusted based on the obtained information of the positions relating to (a) at least one of the first eye to be examined and the first optical head unit, (b) the focusing optical system, and (c) the coherence gate.

18. A non-transitory computer-readable storage medium storing a program for causing a computer to execute the method according to claim 17.

* * * * *